(12) United States Patent
Nordkild et al.

(10) Patent No.: US 12,076,368 B2
(45) Date of Patent: Sep. 3, 2024

(54) TREATMENT OF LIVER, BILIARY TRACT AND PANCREATIC DISORDERS

(71) Applicant: Novozymes A/S, Bagsvaer (DK)

(72) Inventors: Peter Nordkild, Gentofte (DK); Soren Kjaerulff, Holte (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 16/097,072

(22) PCT Filed: Apr. 28, 2017

(86) PCT No.: PCT/DK2017/050132
§ 371 (c)(1),
(2) Date: Oct. 26, 2018

(87) PCT Pub. No.: WO2017/186250
PCT Pub. Date: Nov. 2, 2017

(65) Prior Publication Data
US 2019/0192626 A1    Jun. 27, 2019

(30) Foreign Application Priority Data

Apr. 29, 2016 (DK) .......................... PA 2016 70276
Jul. 1, 2016  (DK) .......................... PA 2016 70484

(51) Int. Cl.
| | |
|---|---|
| *A61K 38/17* | (2006.01) |
| *A61K 9/00* | (2006.01) |
| *A61K 38/04* | (2006.01) |
| *A61K 38/26* | (2006.01) |
| *A61P 1/16* | (2006.01) |
| *A61P 1/18* | (2006.01) |
| *A61P 3/00* | (2006.01) |
| *A61K 45/06* | (2006.01) |

(52) U.S. Cl.
CPC ........ *A61K 38/1729* (2013.01); *A61K 9/0053* (2013.01); *A61K 38/04* (2013.01); *A61K 38/26* (2013.01); *A61P 1/16* (2018.01); *A61P 1/18* (2018.01); *A61P 3/00* (2018.01); *A61K 45/06* (2013.01)

(58) Field of Classification Search
None
See application file for complete search history.

(56) References Cited

U.S. PATENT DOCUMENTS

| | | |
|---|---|---|
| 5,223,409 A | 6/1993 | Ladner et al. |
| 7,855,177 B1 | 12/2010 | Wahren et al. |
| 9,279,010 B2 * | 3/2016 | Kjaer ................ C07K 14/4723 |
| 2004/0091498 A1 | 5/2004 | Zhang et al. |
| 2008/0051333 A1 | 4/2008 | Shi |
| 2011/0311601 A1 | 12/2011 | Kleine et al. |
| 2013/0052213 A1 | 2/2013 | Kjaer et al. |
| 2013/0336950 A1 | 12/2013 | Wehkamp et al. |
| 2014/0073563 A1 | 3/2014 | Boscheinen et al. |
| 2014/0213521 A1 * | 7/2014 | Rosenkilde Kjær ................ A61K 38/1729 514/13.5 |

FOREIGN PATENT DOCUMENTS

| | | | |
|---|---|---|---|
| CN | 104971343 A | | 10/2015 |
| CN | 105504063 | * | 4/2016 |
| CN | 105504063 A | | 4/2016 |
| WO | 9206204 A1 | | 4/1992 |
| WO | 9517413 A1 | | 6/1995 |
| WO | 9522625 A1 | | 8/1995 |
| WO | 2007081486 A2 | | 7/2007 |
| WO | 2007133373 A2 | | 11/2007 |
| WO | 2007/148078 A1 | | 12/2007 |
| WO | 2008115390 A2 | | 9/2008 |
| WO | 2010/007165 A2 | | 1/2010 |
| WO | 2010007166 A2 | | 1/2010 |
| WO | 2012/177929 A2 | | 12/2012 |
| WO | 2013/007596 A2 | | 1/2013 |
| WO | 2013006692 A2 | | 1/2013 |
| WO | 2017/129195 A1 | | 8/2017 |

OTHER PUBLICATIONS

Translation of CN 104971343 (Oct. 14, 2015) retrieved from https://patents.google.com/patent/CN104971343B/en?oq=cn104971343 on Nov. 12, 2019, 14 pages (Year: 2019).*
Translation of CN 105504063 (Apr. 20, 2016) retrieved from https://patents.google.com/patent/CN105504063A/en on Jun. 12, 2019, 13 pages (Year: 2019).*
Younossi et al. ('Association of nonalcoholic fatty liver disease (NAFLD) with hepatocellular carcinoma (HCC) in the United States from 2004 to 2009' Hepatology Dec. 2015 pp. 1723-1730) (Year: 2015).*
Mayo Clinic entry for liver failure (retrieved from https://www.mayoclinic.org/diseases-conditions/acute-liver-failure/symptoms-causes/syc-20352863 on Jul. 22, 2022, 6 pages) (Year: 2022).*
Tang et al., Animal Science Journal, 2015; vol. 87; No. 10; pp. 1258-1266.
Baffy et al., Journal of Hepatology, 2012; 56; pp. 1384-1391.
Harada et al., Hepatology, 2004; vol. 40; No. 4; pp. 925-932.
Ner, et al., DNA, 1988; vol. 7; No. 2; pp. 127-134.
Ridaura, et al, Science 341, 2013; DOI:10.1126/science.1241214.
Shechter et al., Bioconjugate Chem. 2005; vol. 16; pp. 913-920.
Shechter et al., International Journal of Peptide Research and Therapeutics, 2006; vol. 13; Nos. 1-2, pp. 105-117.
Wertenbruch et al., Digestion, 2015; vol. 91; pp. 307-317.
Everard, A. and Cani, P.D., Best Practice & Research Clinical Gastroenterology, 2013; vol. 27; pp. 73-83.
Everard et al., PNAS, 2013; vol. 110; No. 22; pp. 9066-9071.
Vrieze et al., Gastroenterology, 2012; vol. 143; No. 4; pp. 913-916.
Armogida et al., Allergy Asthma Proc. 2004; vol. 25; No. 5; pp. 297-304.

(Continued)

*Primary Examiner* — Ronald T Niebauer
(74) *Attorney, Agent, or Firm* — Weston R. Gould; Dinsmore & Shohl LLP

(57) ABSTRACT

The present invention relates to methods for treatment or prevention of liver, biliary tract, and pancreatic disorders by administering one or more defensins. Included within the scope of the disclosure is also treatment of certain metabolic disorders.

20 Claims, 51 Drawing Sheets

Specification includes a Sequence Listing.

(56) References Cited

OTHER PUBLICATIONS

Chassaing et al., Nature, 2015; vol. 519 No. 7541; pp. 92-96.
Cunningham, B.C. and Wells, J.A., Science, 1989; vol. 244; pp. 1081-1085.
Derbyshire et al., Gene, 1986; vol. 46; pp. 145-152.
Hilton et al., Journal of Biological Chemistry, 1996; vol. 271; No. 9; pp. 4699-4708.
Angelakis, E. and Raoult, D., PLoS One, 2010; vol. 5; Iss. 5; e10463.
Angelakis et al., Microbial Pathogenisis, 2012; vol. 52; Iss.1; pp. 61-68.
Backhed et al., PNAS, 2007; vol. 104; No. 3; pp. 979-984.
Faulds, M.H. and Dahlman-Wright, K., Current Opinion Oncology, 2012; vol. 24; No. 1; pp. 58-61.
Favre-Godal et al., Phytochemistry, 2014; vol. 105; pp. 68-78.
Feng et al., Nature Communications, 2015; vol. 6.; No. 6528; DOI: 10.31038/ncomms7528.
Giannouli et al., BMC Microbiology, 2014; vol. 14; No. 228.
Liu et al., The Journal of Biological Chemistry, 2008; vol. 283; No. 18; pp. 12056-12063.
Walter, J., Cell Host Microbe, 2015; vol. 17; No. 1; pp. 3-5.
Wehkamp et al., Nature Clinical Practice: Gastroenterology & Hepatology, 2005; vol. 2; No. 9; pp. 406-415.
Bowie, J.D. and Sauer, R.T., Proc. Natl. Acad. Science USA, 1989; vol. 86; pp. 2152-2156.
Khan et al., British Poultry Science, 2007; vol. 48; No. 6; pp. 732-735.
Nakamura et al., Bioscience of Microbiota, Food and Health, 2015; vol. 35; No. 2; pp. 57-67.
Krentz et al., Drugs, 2008; vol. 68; No. 15; pp. 2131-2162.
Trasande et al., International Journal of Obesity (Lond), 2012; vol. 37; No. 1.
Le Chatelier et al., Nature, 2013; vol. 500; No. 7464; pp. 541-546.
Leviten, M., Biocentury Innovations, 2016.
Neff et al., Diabetes, Metabolic Syndrome and Obesity: Targets and Therapy, 2010; vol. 3; pp. 263-273.
Lowman et al., Biochemistry, 1991; vol. 30; pp. 10832-10838.
Mowat, A.M. and Agace, W. W., Nature Reviews: Immunology, 2014; vol. 14; pp. 667-685.
Needleman, S.B. and Wunsch, C.D., Journal of Molecular Biology, 1970; vol. 48; pp. 443-453.
Salzman, N.H., Gut Microbes, 2010; vol. 1; No. 6; pp. 401-406.
Koren et al., Cell, 2012; vol. 150; No. 3; pp. 470-480.
Turnbaugh et al., Cell Host Microbe, 2008; vol. 3; No. 4; pp. 213-223.
Qin et al., Nature, 2012; vol. 490; No. 7418; pp. 55-60.
Reidhaar-Olson, J.F. and Sauer, R.T., Science, 1988; vol. 241; pp. 53-57.
Rice et al., Trends in Genetics, 2000; vol. 16; No. 6; pp. 276-277.
Salzman et al.,Seminars in Immunology, 2007; vol. 19; pp. 70-83.
Suez et al., Nature, 2014; vol. 514; pp. 181-186.
Ajslev et al., PLoS One, 2014; vol. 9; Iss. 10; e109932.
Turnbaugh et al., Nature, 2006; vol. 444; pp. 1027-1031.
Ridaura et al., Science, 2013; vol. 341; No. 6150; pp. 1-22.
Belkaid, Y. and Hand, T., Cell, 2014; vol. 157; No. 1; pp. 121-141.
Wehkamp et al.,Digestive Diseades and Sciences, 2002; vol. 47; No. 6; pp. 1349-1655.
Zhang et al., Nature Medicine, 2015; vol. 21; No. 8; pp. 895-906.
Carding, S. et al., Dysbiosis of the gut microbiota in disease, Microbial Ecology in Health & Disease, 26:26191, 9 pages, Feb. 2, 2015.
Allin et al., Gut microbiota in patients with type 2 diabetes mellitus, European Society of Endocrinology, vol. 172(4): 167-177 (Feb. 2015) (Year: 2015).
Belizario et al., Human microbiomes and their roles in dysbiosis, common diseases, and novel therapeutic approaches, Front Microbial., vol. 6:1050 (Published online Oct. 6, 2015.) doi: 10.3389/fmicb.2015.01050 (Year: 2015).
Hansen et. al., The gut microbiome in cardio-metabolic health, Genome Med., vol. 7(1):33, 16 pages (online Mar. 31, 2015) (Year: 2015).
Larsen et al., Gut microbiota in human adults with type 2 diabetes differs from non-diabetic adults, PLoS One, vol. 5 (2):e9085 (Feb. 5, 2010) (Year: 2010).
Moreno-Indias et al., Impact of the gut microbiota on the development of obesity and type 2 diabetes mellitus, Front. Microbial., vol. 5:190 (2014) (Year: 2014).
Portela-Cidade et al., Systematic Review of the Relation Between Intestinal Microbiota and Toll-Like Receptors in the Metabolic Syndrome: What Do We Know So Far?, GE PortJ. Gastroenterol., vol. 22(6):240-258 (Aug. 2015) (Year: 2015).
Tilg et al., Gut Microbiome, obesity, and metabolic dysfunction, J Clin Invest., vol. 121 (6): 2126-2132 (Jun. 1, 2011 ); (Year: 2011).
Fonseca, et al., Clinical Cornerstone, vol. 7(2/3):61-72; Year 2005.
Incani, et al., Journal of Diabetes Investigation, vol. 6(1):44-50; Year 2014.
Lehrer et al, Interaction of human defensins with *Eschericia coli*. Mechanism of bactericidal activity, J. Clin. Invest., 84(2): 553-561, 1989.
Han, Y. et al., Vitamin D through Induction of Paneth Cell Defensin Attenuates Gut Dysbiosis and Improves Metabolic Disorders in Animal Models, Hepatology, 62(1) (Suppl), 655A-656A(904), Oct. 2015.
Mattar, E. et al., Virucidal activity of human alpha- and beta-defensins against hepatitis C virus genotype 4, Molecular Biosystems, 12: 2785-2797, 2016, XP 055395471.
Su, D. et al., Vitamin D signaling through induction of paneth cell defensins maintains gut microbiota and improves metabolic disorders and hepatic steatosis in animal models; Frontiers in Physiology, 7(498): pp. 1-12, Nov. 2016, XP 055360163.
Ladevaia, M. et al., Rifaximin in the treatment of hepatic encephalopathy, Hepatic Medicine: Evidence and Research, 3: 109-117, 2011.
Tabibian, J. et al., Prospective clinical trial of rifaximin therapy for patients with primary sclerosing cholangitis with primary endpoint serum alkaline phosphatase, Am J Ther, 24(1): e56-e63; 2017.
Festi, D. et al., Gut microbiota and metabolic syndrome, World Journal of Gastroenterology, 20(43): 16079-1069, Nov. 21, 2014, doi:10.3748/wjg.v20.i43.16079.
Hanaoka, Y., et al., In Vitro and In Vivo Anticancer Activity of Human β-Defensin-3 and Its Mouse Homolog, Anticancer Research, 36: 5999-6004, 2016.
Budikhina, A., Defensins—multifunctional cations peptides of human, Immunopathology, allergology, infectology, 2: 31-40, 2008.
English translation of Budikhina 2008, paragraphs 3-9 on p. 39.
Sankaran-Walters, et al., Guardians of the Gut: Enteric Defensins, Frontiers in Microbiology, 8(647): pp. 1-8, Apr. 19, 2017.
Trend, S. et al., Antimicrobial Protein and Peptide Concentrations and Activity in Human Breast Milk Consumed by Preterm Infants at Risk of Late-Onset Neonatal Sepsis, PLOS One, 10(2): e0117038, Feb. 2, 2015.

\* cited by examiner

Fig. 3

```
HBD1      ------DHYNCVSSGGQCLYSACPIFTKIQGTCYRGKAKCCK---  (SEQ ID NO: 4)
HBD2      ---GIGDPVTCLKSGAICHPVFCPRRYKQIGTCGLPGTKCCKKP-  (SEQ ID NO: 5)
HBD3      GIINTLQKYYCRVRGGRCAVLSCLPKEEQIGKCSTRGRKCCRRKK  (SEQ ID NO: 6)
HBD4      -----ELDRICGYGTARCR-KKCRSQEYRIGRCPN-TYACCLRK-  (SEQ ID NO: 7)
                  *  . *      *       * *      **
```

Fig. 4

```
HD5       -ATCYCRTGRCATRESLSGVCEISGRLYRLCCR  (SEQ ID NO: 8)
HD6       AFTCHCRR-SCYSTEYSYGTCTVMGINHRFCCL  (SEQ ID NO: 9)
           **:**    *  :  *    *.*  :  *    :*:**
```

Fig. 5

```
HNP2      -CYCRIPACIAGERRYGTCIYQGRLWAFCC  (SEQ ID NO: 18)
HNP3      DCYCRIPACIAGERRYGTCIYQGRLWAFCC  (SEQ ID NO: 19)
HNP1      ACYCRIPACIAGERRYGTCIYQGRLWAFCC  (SEQ ID NO: 20)
           *****************************
```

Fig. 6

```
hBD2         ---GIGDPVTCLKSGAICHPVFCPRRYKQIGTCGLPGTKCCKKP  (SEQ ID NO: 5)
Chimpanzee   ---GISDPVTCLKSGAICHPVFCPRRYKQIGTCGLPGTKCCKKP  (SEQ ID NO: 10)
Macaque      ---GIGDPVTCLKNGAICHPVFCPRRYKQIGTCGLPGTKCCKKP  (SEQ ID NO: 11)
Orangutan    VFGDISNPVTCLRSGAICHPGFCPRRYKHIGTCGLSVIKCCKKP  (SEQ ID NO: 3)
Goat         ---GIINHRSCYRNKGVCAPARCPRNMRQIGTCHGPPVKCCR-  (SEQ ID NO: 15)
Bovine       ---GVGNPVSCVRNKGICVPIRCPGSMKQIGTCVGRAVKCCR-  (SEQ ID NO: 1)
Horse        ---GIGNPISCARNRGVCIPIGCLPGMKQIGTCGLPGTKCCRK-  (SEQ ID NO: 13)
Porcine      ---NIGNSVSCLRNKGVCMPGKCAPKMKQIGTCGMPQVKCCKR-  (SEQ ID NO: 14)
Mouse        ---KINNPVSCLRKGGRCWN-RCIGNTRQIGSCGVPFLKCCKRK  (SEQ ID NO: 12)
                 : :  :* :. . *     *     ::**:*      ***::
```

Fig. 16A
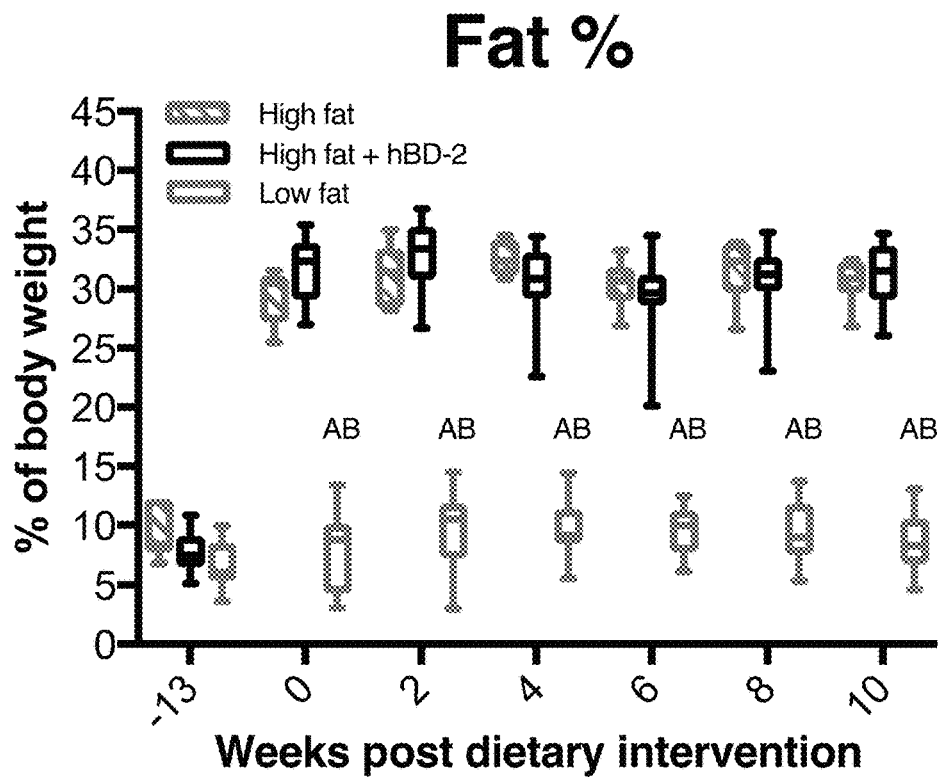
Fig. 16B
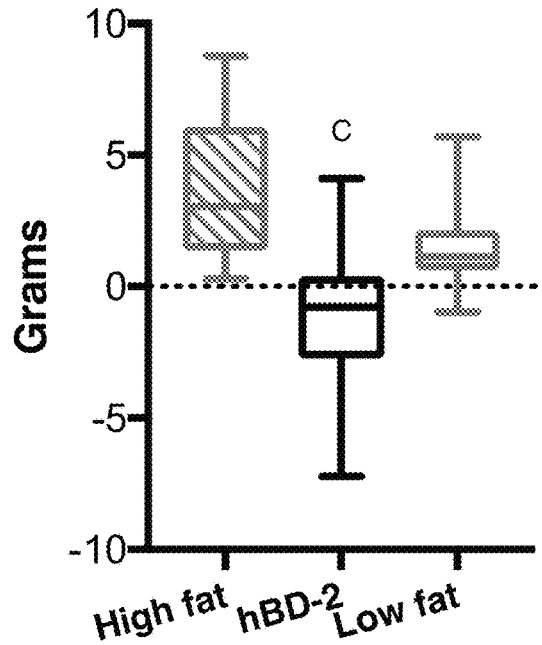

TREATMENT OF LIVER, BILIARY TRACT AND PANCREATIC DISORDERS

This application is a U.S. national stage of PCT/DK2017/050132 filed Apr. 28, 2017, which claims priority to Denmark Application No: PA 2016 70276 filed Apr. 29, 2016 and Denmark Application No: PA 2016 70484 filed Jul. 1, 2016, the contents of each of which are incorporated herein by reference.

This application incorporates by reference a Sequence Listing with this application as an ASCII text file entitled "Sequence_Listing_corrected_ST25" created on Mar. 2, 2020 having a size of 8,109 bytes.

TECHNICAL FIELD

The present invention relates to methods for treatment or prevention of liver, biliary tract, and pancreatic disorders by administering one or more defensins. Included within the scope of the disclosure is also treatment of certain metabolic disorders.

BACKGROUND

Intestinal Microbiota

The increasing prevalence of common disorders like obesity and obesity related diseases is tightly associated with our westernized lifestyle and diet. The most prominent obesity-related ailments are insulin resistance, overt type 2 diabetes (T2D) and certain cancers (Faulds & Dahlman-Wright, 2012). While the aetiology of these diseases is complex, many of them are characterized by a general state of low-grade inflammation, which may originate from a dysregulated intestinal microbiota and metabolome (Everard & Cani, 2013; Belkaid & Hand, 2014). Even though the challenges associated with modern human lifestyles and animal meat production may seem far apart, it is envisaged that impaired intestinal health is a common denominator. Dysregulated intestinal health is indeed associated with an array of diverse diseases like obesity (Ridaura et al, 2013), T2D (Qin et al, 2012), rheumatoid arthritis (Zhang et al, 2015) and colorectal cancer (Feng et al, 2015). Recently, a connection between intestinal microbiota, and in particular the presence of certain lipopolysaccharides from *Bacteroides*, and the higher rate of occurrence of type 1 diabetes in Finland in comparison to neighbouring areas has been reported (Leviten 2016).

Obesity and its concomitant low-grade inflammation form a potent driver of dysregulated metabolic homeostasis. Turnbaugh et al. (2006) found that obesity-associated microbiota had an increased capacity for energy harvest, and 2 weeks after transplantation of microbiota from obese mice, germ-free mice showed significantly greater increase in fat mass than similar transplantation from lean mice. Turnbaugh et al. (2008) further and significantly discovered that changes in intestinal microbial composition were completely reversed after a shift back to the original diet in mice temporarily fed a high fat/sugar "Western" diet. These findings were confirmed in man by Vrieze et al. (2012), who demonstrated that transfer of intestinal microbiota from lean human donors increased insulin sensitivity in individuals with metabolic syndrome.

Manipulation of intestinal microbiota to increase weight and weight-gain rates has been employed for many years in agricultural live-stock through the use of low-dose antibiotics and probiotics such as *Lactobacillus ingluviei*. Intestinal microbiota manipulation for weight gain has been demonstrated in chickens (Khan et al, 2007), in ducks (Angelakis & Raoult, 2010), and in mice (Angelakis et al, 2012). In humans, infants receiving antibiotics have also been found to be larger than their controls (Trasande et al, 2012), while early exposure to oral antibiotics is associated with overweight in children (Ajslev et al, 2014). In pregnant women, the physiological increase in adiposity and potential development of gestational diabetes in the third trimester also appears to be associated with a profound change in intestinal microbiota (Koren et al, 2012).

The intestinal mucosa is by far the largest body surface (approximately 200 m$^2$) exposed to the external environment. As such, the intestinal surface is in intimate contact with foreign material, metabolites (metabolome) derived from our diet, and the estimated 10$^{14}$ bacteria—the intestinal microbiota—that inhabit our intestine. Thus the intestinal barrier is under constant and intense immune surveillance, requiring a dynamic crosstalk among the immune system, dietary components, and the intestinal microbiota. Diet interventions have tremendous impact on immune regulation (Mowat & Agace, 2014) and intestinal microbiota composition (Walter, 2015), both of which independently and synergistically influence metabolic homeostasis. In this regard, two very recent papers emphasize the (adverse) potential of food additives in microbiota-modulated changes to metabolic homeostasis. A recent paper (Chassaing et al, 2015) illustrated how dietary emulsifiers impair glucose tolerance, thus increasing weight gain as well as colitis susceptibility by induction of a dysregulated intestinal microbiota. The observations could not be replicated in germ-free (GF) mice, suggesting a pivotal role for the intestinal microbiota. Similarly, Suez et al. (2014) recently showed how non-caloric artificial sweeteners induced metabolic dysfunction through alterations of the intestinal microbiota. The authors validated their findings by faecal transfer to GF mice, after which the GF mice rapidly developed glucose intolerance. These observations mirror a pioneering study in GF mice (Bäckhed et al, 2007), elucidating the role of intestinal microbes in the maintenance of metabolic health. This study showed that in the absence of commensal microbes, thereby causing an imbalanced mucosal immune homeostasis, the adipose tissues decreased in size and function in response to a high fat diet. Despite lack of weight gain, which normally would appear as a healthy phenotype, ectopic lipid accumulation (hepatic steatosis & increased levels of serum triglycerides) resulted in severe metabolic disorders. In man, it has been shown that gene richness of the microbiota is associated with a healthy phenotype, whereas gene poverty (low gene counts) correlates with increased risk of metabolic disorders (Le Chatelier et al, 2013).

Wertenbruch et al 2015 demonstrated that the levels of the anti-microbial peptide LL-37/CRAMP (cathelicidin), human beta defensin 2 and complement factor C5a are elevated in blood serum from patients with liver diseases compared to healthy controls. Serum levels for all three markers are relatively narrow for healthy controls but there is a wide variation in the levels for liver patients. The authors speculate that the elevated levels of hBD-2 might reflect an increased remodelling of biliary epithelia.

Harada et al 2004 have studied levels of hBD1 and hBD-2 in intrahepatic biliary epithelial cells, in cell lines and in bile. hBD-2 expression was found in bile ducts during active inflammation. The bile levels were found to correlate with the serum levels of CRP. The authors conclude that hBD-2 is expressed in response to local infection or active inflammation and that hBD1 may be a pre-existing component of the biliary antimicrobial defense system.

Defensins

Defensins represent one of the dominant innate host defenses that serve to maintain a healthy microbiome and ward off potential pathogens (Wehkamp et al, 2002 and Salzman et al, 2007). Defensins are peptides possessing antimicrobial activity against Gram positive and negative bacteria, fungi and archaea as well as anti-inflammatory activity increasing anti-inflammatory cytokines and decreasing inflammatory cytokines.

The human defensins are small cationic peptides that can be divided into α- and β-defensins based on the topology of their three intramolecular cysteine disulphide bonds. The human α-defensins can be further subdivided into those that were first isolated from neutrophil granules (HNP1-4) and intestinal defensins that are expressed by Paneth cells in the crypts of the small intestine (HD5 and HD6 or DEFA5 and DEFA6). The β-defensins (DEFBn) are mainly produced by epithelial cells in various tissues and organs including the skin, eye, middle ear, mouth, trachea, lungs, gastrointestinal tract, liver, urogenital system, kidneys, vagina, pancreas and mammary glands. The best characterized members of the human β-defensin family are hBD1-4. Some of the human defensins are produced constitutively, whereas others are induced by pro-inflammatory cytokines or exogenous microbial products. Some of the human defensins are already expressed in the amniotic fluid at increasing levels with gestational age, protecting the fetus in the womb. Breast milk and in particular the first milk, colostrum, contains both α- and β-defensins and cathelicidin, but only a few of them are found in significant concentrations in maternal milk (Armogida et al, 2004).

Liu et al. (2008) found that HNP-1 and HNP-2, both produced by leucocytes and belonging to a subgroup of α-defensins in the blood, were able to inhibit glycogenolysis and gluconeogenesis in isolated hepatocytes through an intracellular mechanism distinctly different from the classical insulin signalling pathway.

CN104971343 discloses that mice fed on a high fat diet and a vitamin D deficiency diet suffer from metabolic syndrome. Expression of defensins after a long period of such a vitamin D-deficient diet is down-regulated and thus leads to defensin deficiency. Administration of defensin HD5 four times over 25 days partly resulted in decrease of plasma glucose levels, but no data are presented relating to insulin resistance or homeostasis model assessment. CN104971343 does not disclose that administration of defensin HD5 to mice on a high fat diet with normal vitamin D levels can treat disorders of the liver, pancreas or biliary tract.

While the prior art discloses a correlation of cathelicidin, complement and beta-defensins with increased biliary inflammation or infection, there is no teaching or suggestion that defensins can be used to treat disorders of the liver, pancreas or biliary tract.

SUMMARY OF INVENTION

The present disclosure demonstrates that mammalian, intestinal α- and β-defensins, orally administered, have the ability of preventing or treating weight gain including central (abdominal or visceral) weight gain and lipid accumulation. The data indicate that administration of mammalian α- and/or β-defensins results in treatment of diseases or disorders of the liver, including liver cancer and hepatic encephalopathy, biliary tract, and pancreas as well as certain metabolic disorders.

Administration of alpha or beta defensin to mice fed on high fat diet affected liver and visceral fat, expression of a steatosis marker and of a marker of liver lipid metabolism, showing that they reduce liver fat and steatosis. Feed intake, feed efficiency, fat uptake and excretion were not affected, showing that administration of defensin did not alter appetite.

According to example 1, a dosage of human beta-defensin 2 (hBD-2) was sufficient to reduce weight gain in mice on a high fat diet. The intake of hBD-2 primarily reduced the fat mass gain. The inventors originally hypothesised that it was predominantly the abdominal i.e. liver and visceral fat mass gain that was reduced; example 2 shows visceral fat mass was indeed significantly reduced after intake of hBD-2 in a high fat diet, while a tendency of reduced liver mass was observed. The glucose tolerance and the glucose stimulated insulin response during glucose challenge were both improved upon administration of hBD-2. Expression of a marker known to correlate with fat accumulation, was significantly reduced. Importantly, the food intake was not significantly affected by the type of diet. Administration of the alpha defensin HD5 to mice fed on a high fat diet resulted in increased fatty acid metabolism.

As shown in example 4, administration of hBD-2 to obese mice tended to reduce weight gain following administration compared to obese mice which did not receive hBD-2, for a similar food intake. Administration of hBD-2 reduced the fat percentage of total body weight and rapidly improved glucose tolerance and insulin tolerance. Similar results were observed upon administration of HD5.

Administration of a glucagon like peptide-1 (GLP-1) analog had a weight lowering effect in mice fed on a high fat diet, and resulted in reduced fat accumulation in the liver and lower plasma cholesterol levels.

All in all, the data presented herein show that alpha defensins, beta defensins, GLP-1 and GLP-1 analogs can be used to treat liver, biliary tract, or pancreatic diseases or disorders.

In one aspect, the present disclosure relates to a method for treatment or prevention of a liver, biliary tract, pancreatic or metabolic disease or disorder, said method comprising administration of an effective amount of a mammalian α-defensin and/or β-defensin and/or a cathelicidin and/or a GLP-1 analog to a subject in need thereof.

In another aspect, the present disclosure relates to a method for treatment of liver cancer, cholangiocarcinoma or pancreatic cancer, said method comprising administration of an effective amount of a mammalian α-defensin and/or β-defensin and/or a cathelicidin and/or a GLP-1 analog alone or in combination with radio-, chemo- or immunotherapy to a subject in need thereof.

In yet another aspect, the present disclosure relates to a mammalian α-defensin and/or β-defensin and/or a cathelicidin and/or a GLP-1 analog for use in the methods described herein.

In yet another aspect, the present disclosure relates to the use of a mammalian α-defensin and/or β-defensin and/or a cathelicidin and/or a GLP-1 analog for the preparation of a medicament for the treatment according to any one of the preceding claims.

DESCRIPTION OF DRAWINGS

FIG. 3. Clustal W (2.1) multiple sequence alignment of human beta defensin 1-4.

FIG. 4. Clustal W (2.1) multiple sequence alignment of human alpha defensin 5 and 6.

FIG. 5: Clustal W (2.1) multiple sequence alignment of human neutrophil peptide 1-3.

FIG. 6: Clustal W (2.1) multiple sequence alignment of human, Rhesus macaque, chimpanzee, orangutan, goat, sheep, bovine, horse, porcine and mouse beta defensin 2.

In the Clustal W alignments:
* indicates positions which have a single, fully conserved residue.
: indicates that one of the following 'strong' groups is fully conserved:
   S,T,A; N,E,Q,K; N,H,Q,K; N,D,E,Q; Q,H,R,K; M,I,L,V; M,I,L,F; H,Y; F,Y,W.
. indicates that one of the following 'weaker' groups is fully conserved:
   C,S,A; A,T,V; S,A,G; S,T,N,K; S,T,P,A; S,G,N,D; S,N,D,E,Q,K; N,D,E,Q,H,K; N,E,Q,H,R,K; V,L,I,M; H,F,Y.

Figure 1:
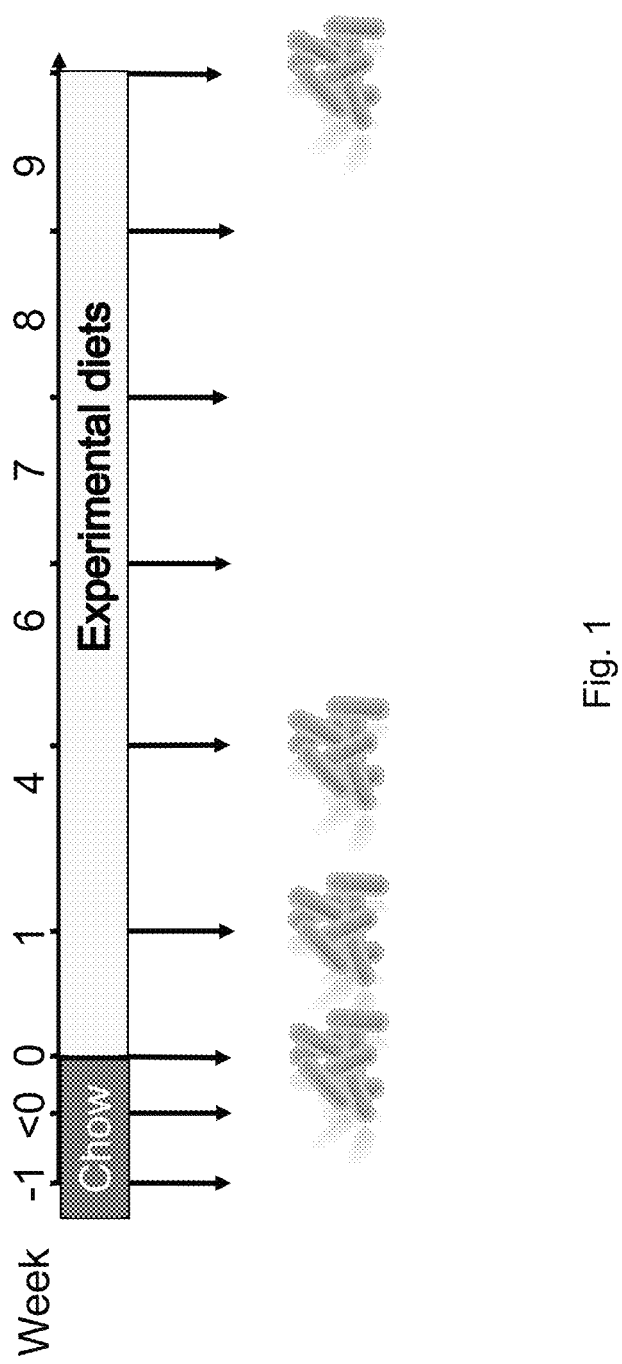
FIG. 1. Schematic outline of the experimental set up for investigating the effects of mammalian alpha and/or beta defensins on mice metabolism. At week −1, the mice were divided in groups and cages, so that there were 3 mice per cage and 4 cages per group. Between week −1 and 0, the mice were clinically examined by magnetic resonance scan to estimate fat distribution. At week 0, 1 and 4, the microbiome of the faeces was analysed. At week 4, in addition to analysis of the microbiota, the mice were scanned and blood glucose and insulin levels were measured. At week 6, the energy consumption was assessed by analysing nitrogen and lipid content of the faeces. At week 7, insulin tolerance test (ITT) was conducted. At week 8, oral glucose tolerance test (OGTT) and glucose-stimulated insulin secretion (GSIS) were conducted. At week 9 (termination), several analyses were conducted, in particular the mice are weighed and scanned, and plasma composition and microbiota composition of colon, cecum and small intestine were assessed. In addition, protein/RNA analysis were performed on muscular tissue (quadriceps), iWAT, eWAT, iBAT, liver, colon, jejunum, ileum and duodenum. Histological analysis is performed on muscular tissue (quadriceps), iWAT, eWAT, iBAT, liver, colon, jejunum, ileum and duodenum.
Figure 2:
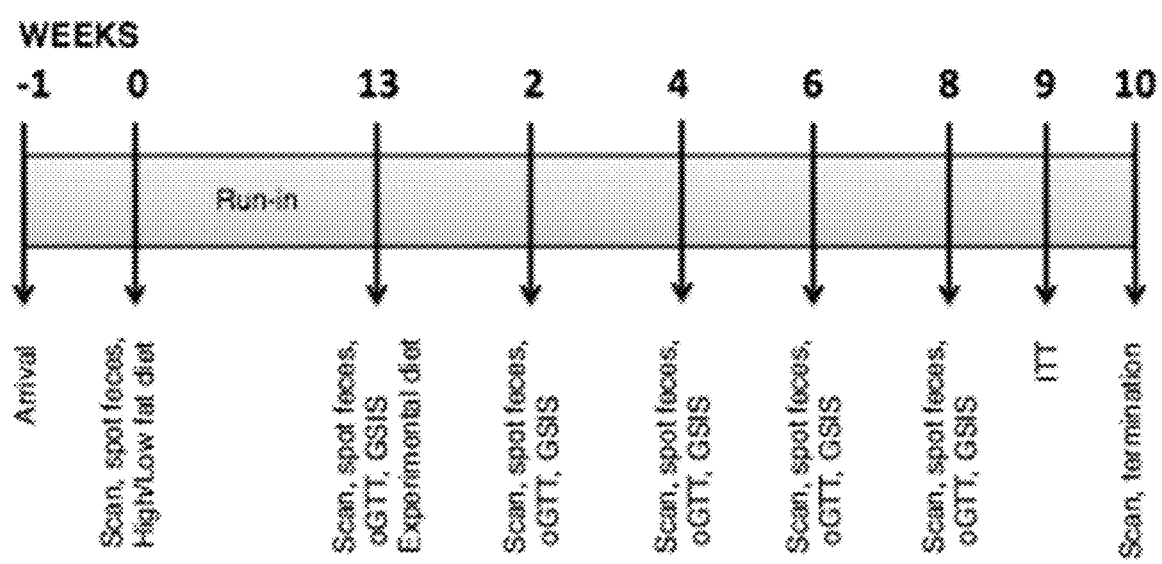
FIG. 2. Schematic outline of the experimental set up for investigating the effects of mammalian alpha and/or beta defensins on mice metabolism. At week −1, the C57/BL/6J mice arrived. At week 0 feces was collected. During run-in between week 0 and week 12 the mice were fed a high fat diet. At week 12 the mice were clinically examined by magnetic resonance scan to estimate fat distribution, feces was collected and oral glucose tolerance test (OGTT) and glucose-stimulated insulin secretion (GSIS) performed. At week 13-0 the mice were divided in groups and cages with 4 mice per cage and 3 cages per group. At week 0, 12 and 13-10, the microbiome of the faeces was analysed. At week 13-2, 13-4, 13-6, 13-8 and 13-10 the mice were scanned and blood glucose and insulin levels were measured. At week 13-9, insulin tolerance test (ITT) was conducted. At week 13-10 (termination), several analyses were conducted, in particular the mice were weighed and scanned, and plasma composition and microbiota composition of colon, cecum and small intestine were assessed. In addition, iWAT, eWAT and liver weight were measured.
Figure 7:
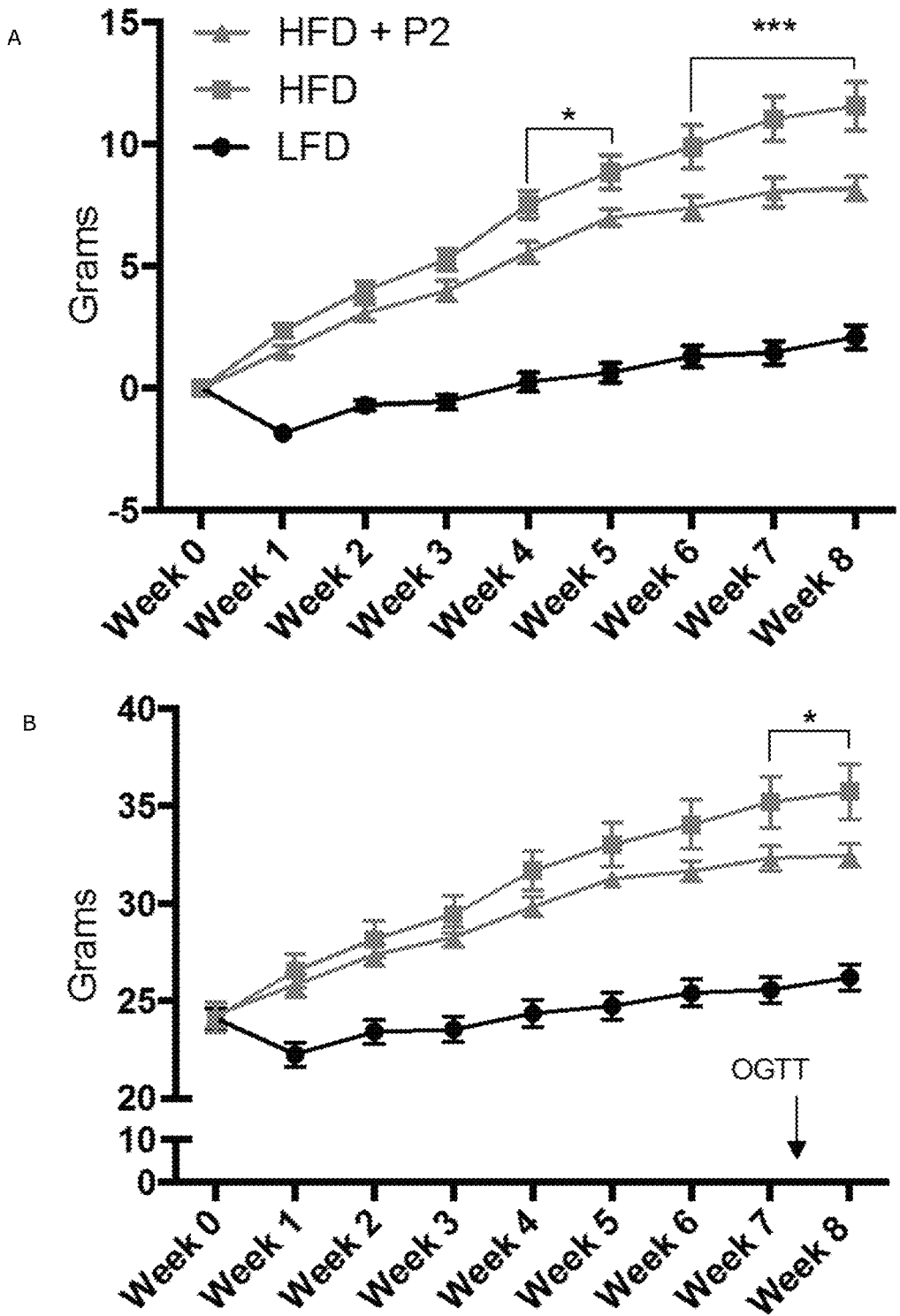
Figure 7:
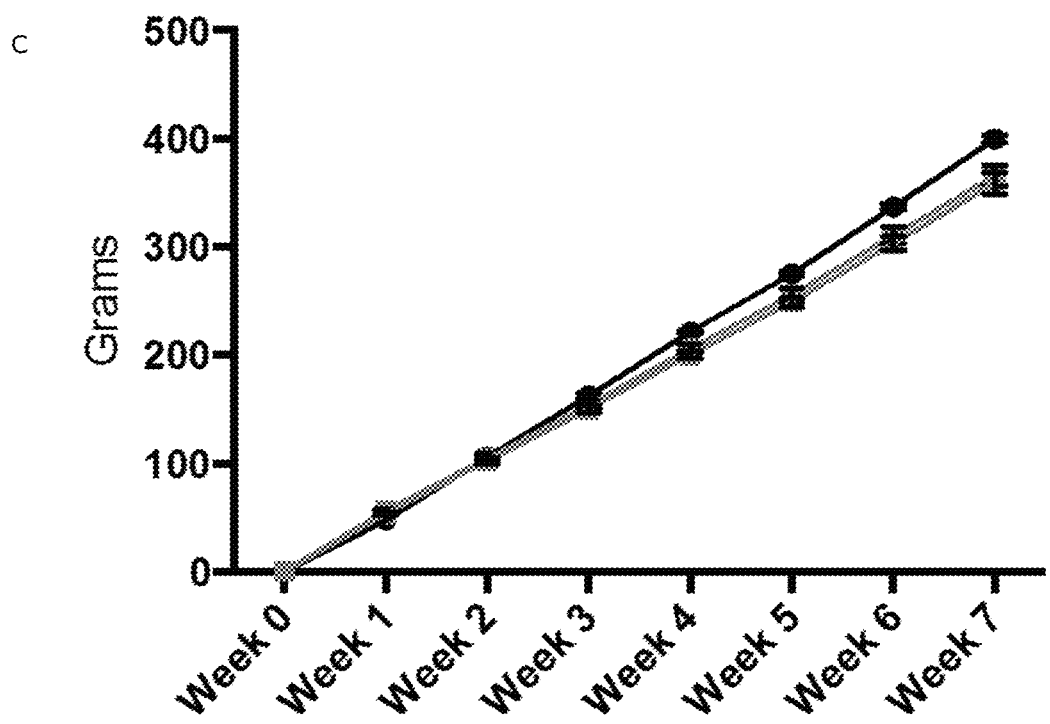

FIG. 7: Weight change (a) and weight development (b) and cumulative feed intake (c) over 7 weeks treatment of mice with low fat diet (LFD), high fat diet (HFD) or HFD and defensin hBD-2 (HFD+P2).

Figure 8A:
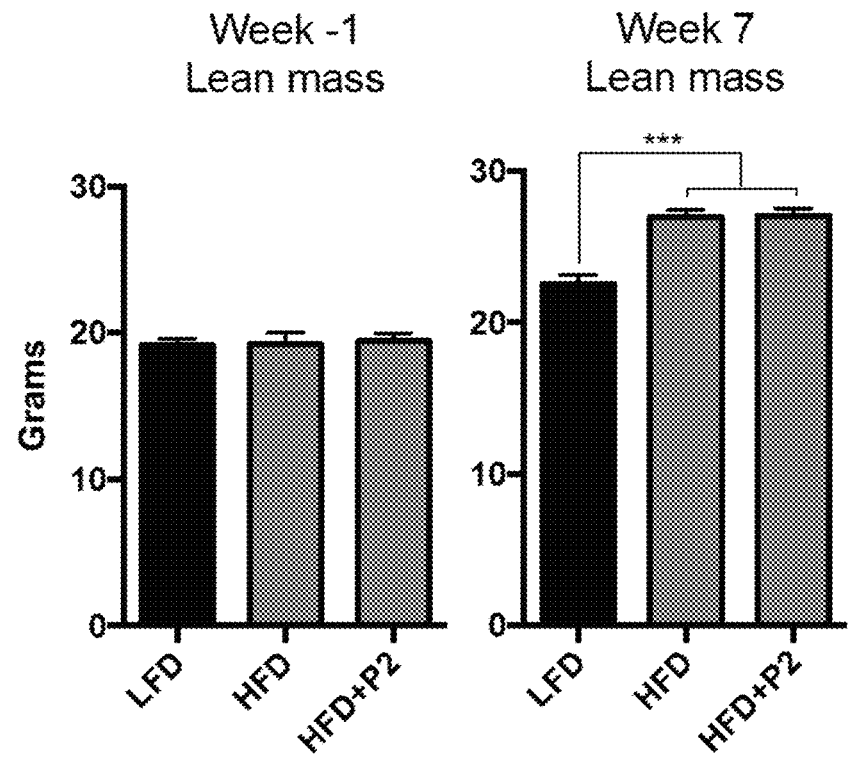
Figure 8B:
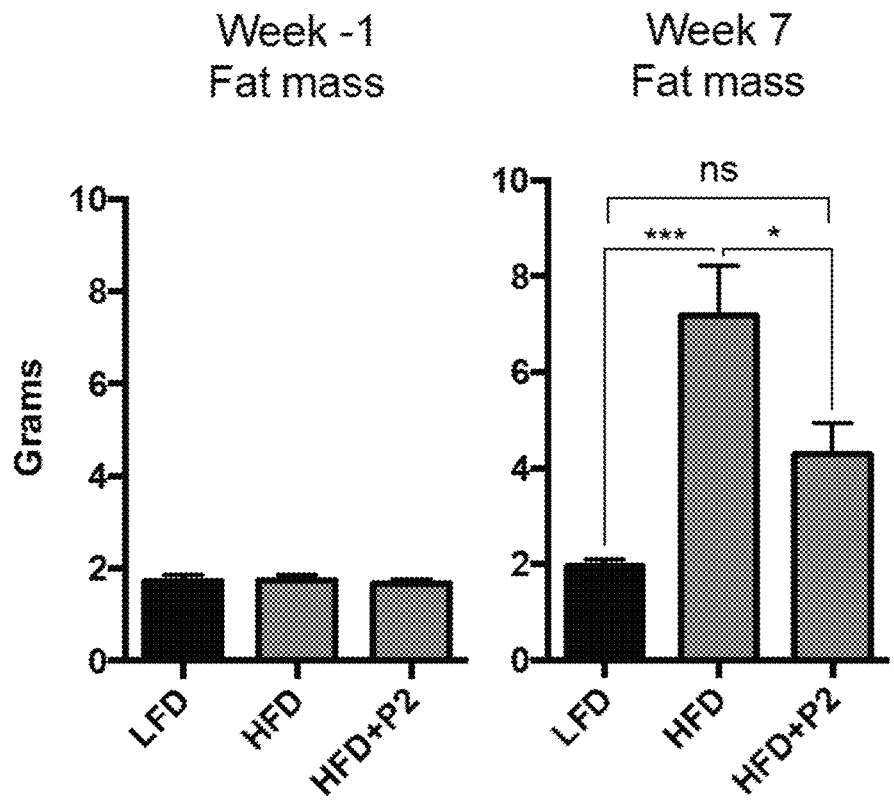

FIG. 8: Lean/fat mass development over 7 weeks treatment of mice with low fat diet (LFD), high fat diet (HFD) or HFD and defensin hBD-2 (HFD+P2). (a) Lean mass development at week 1 and at week 7. (b) Fat mass development at week 1 and at week 7.

FIG. 9: Glucose homeostasis in mice treated for 7 weeks with low fat diet (LFD), high fat diet (HFD) or HFD and defensin hBD-2 (HFD+P2). (a) Insulin tolerance test (ITT). (b) Oral glucose tolerance test. (c) Glucose stimulated insulin secretion (GSIS). (d) 5-hour fasting insulin test.

Figure 10A:
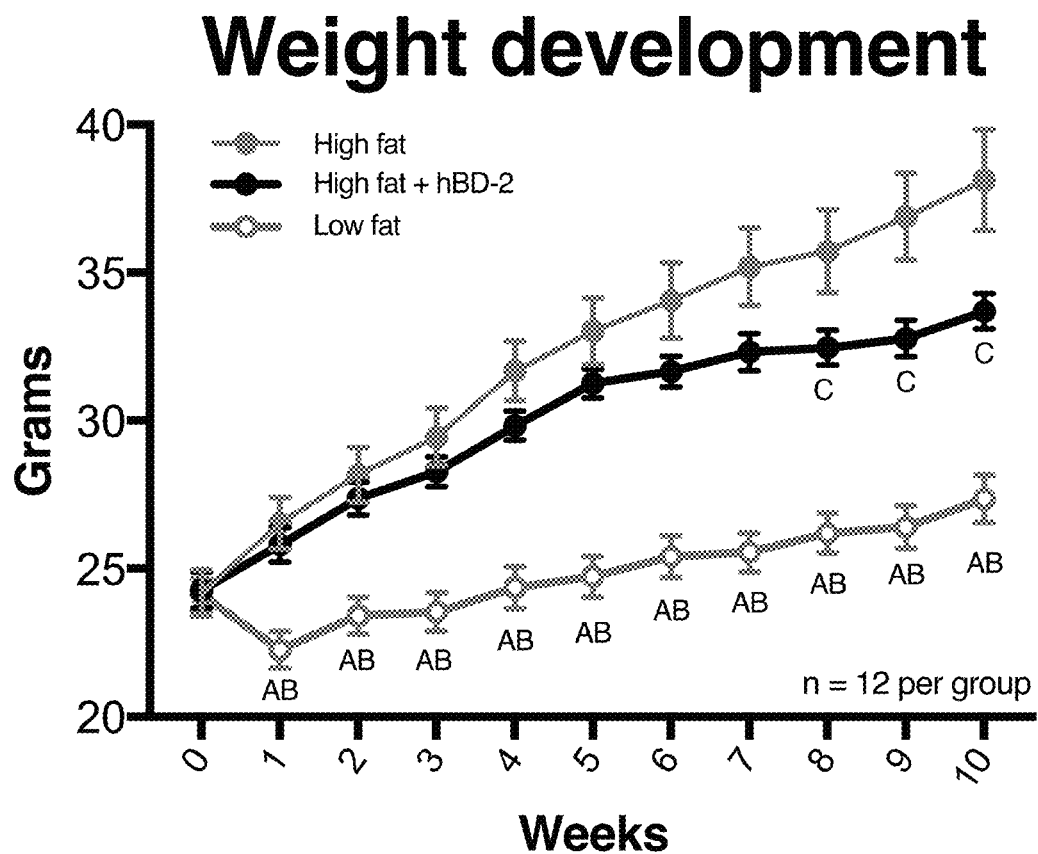
Figure 10B:
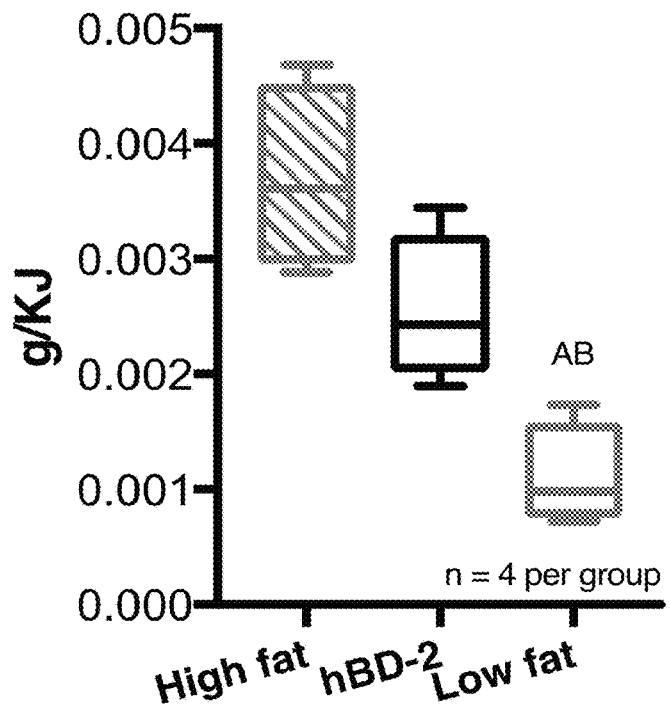
Figure 10C:
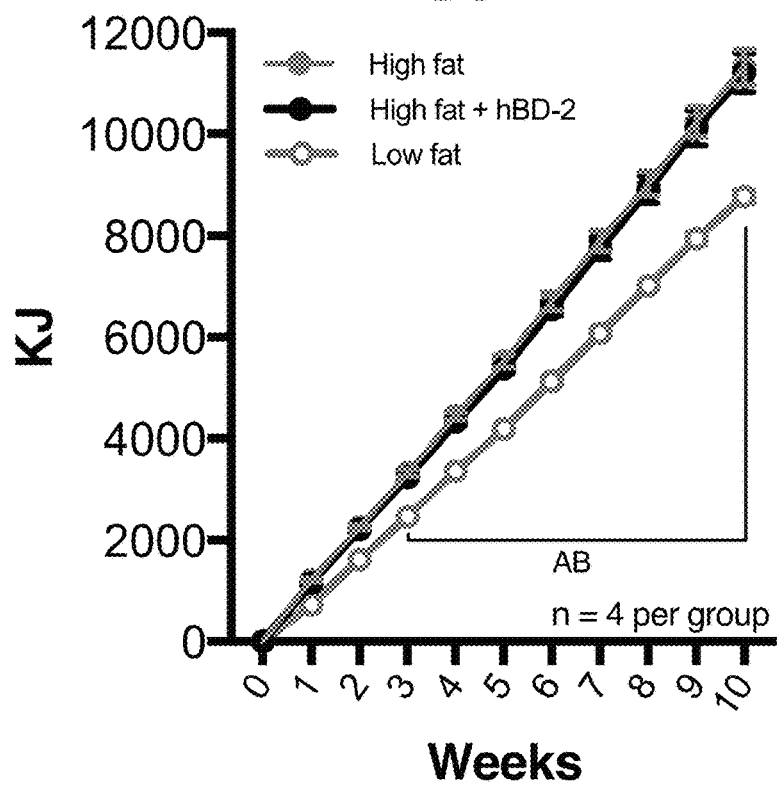

FIG. 10: Weight development (A) feed efficiency (B) and energy intake (C) over 10 weeks treatment of mice with low fat diet (low fat), high fat diet (high fat) or high fat diet and preventive treatment with defensin hBD-2 (high fat+hBD-2).

Significance: Low fat vs. High fat=A; Low fat vs. High fat+hBD-2=B;

High fat vs. High fat+hBD-2=C. (A). Weight development. Two-way ANOVA with Tukey correction (matched values stacked). (B) Feed efficiency (gram of gained weight adjusted for average food intake in the cage). One-way ANOVA with Tukey correction correction NB! n=4 due to co-caging. (C) Energy intake. Two-way ANOVA with Tukey correction (matched values stacked)

Figure 11A:
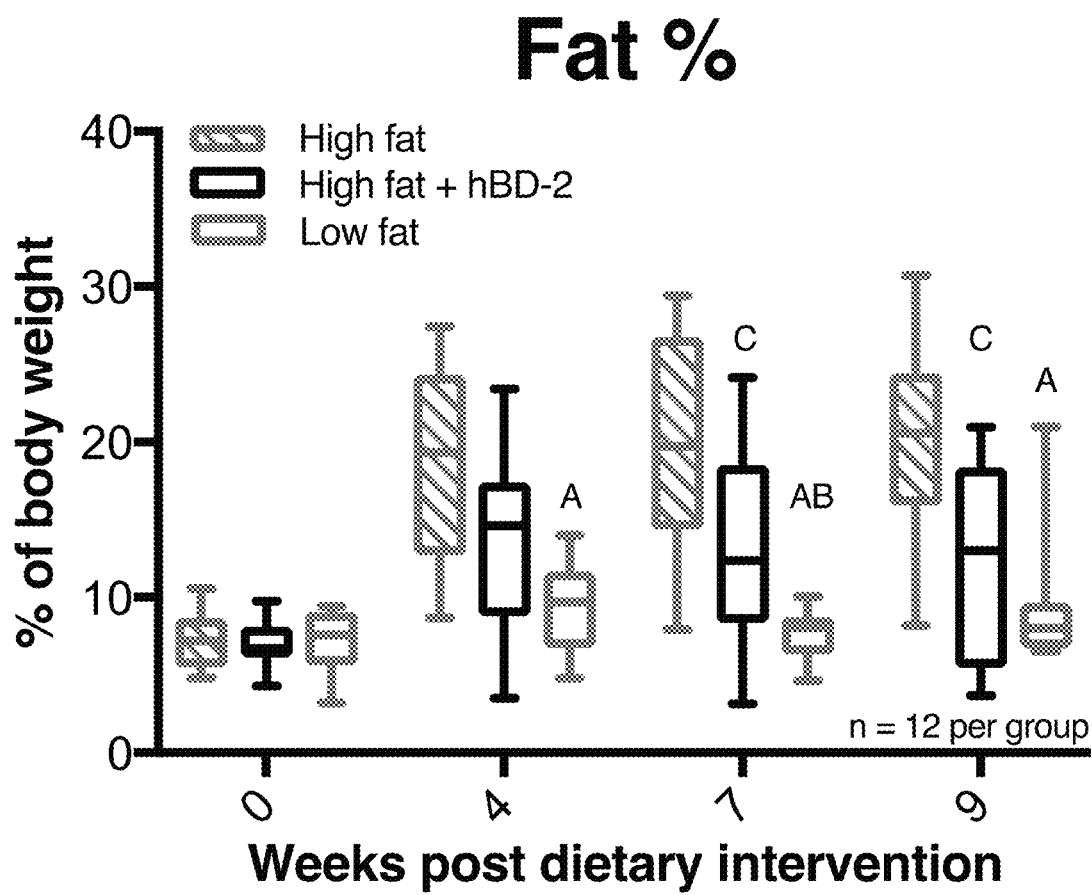
Figure 11B:
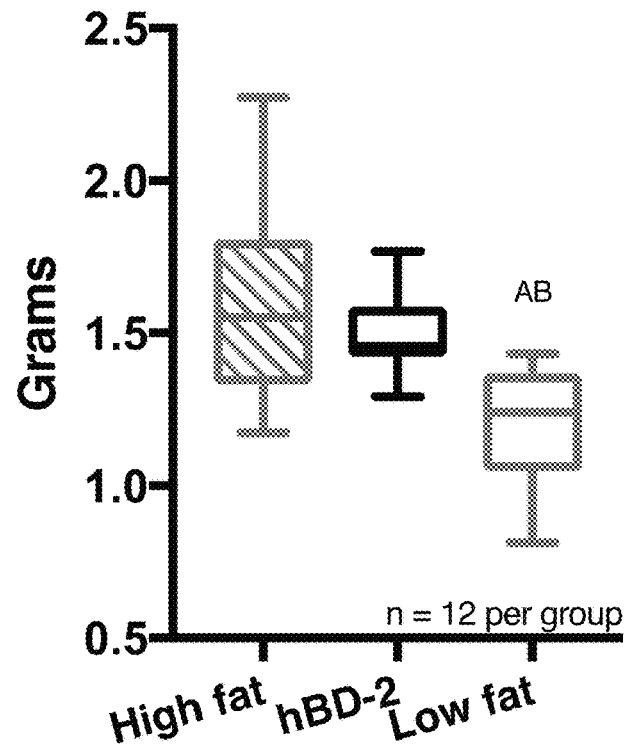
Figure 11C:
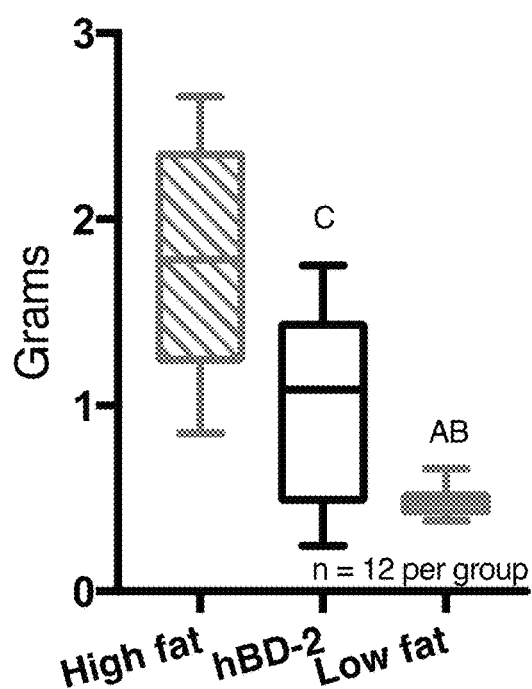

FIG. 11: Fat as a percent of total body weight (A), liver weight in gram (B) and weight of epididymal fat (eWAT) in gram (C) over 10 weeks treatment of mice with low fat diet (low fat), high fat diet (high fat) or high fat diet and preventive treatment with defensin hBD-2 (hBD-2). Significance: Low fat vs. High fat=A; Low fat vs. High fat+hBD-2=B; High fat vs. High fat+hBD-2=C. (A) Fat percentage of total body weight in different weeks. Two-way ANOVA with Tukey correction (matched values stacked). (B) Weight of epididymal adipose tissue (visceral AT) at termination. One-way ANOVA with Tukey correction. (C) Weight at termination. One-way ANOVA with Tukey correction.

FIG. 12: Glucose homeostasis in mice treated for 10 weeks with low fat diet (low fat), high fat diet (high fat) or high fat diet and preventive treatment with defensin hBD-2 (high fat+hBD-2). (A) Oral glucose tolerance test. (B) Glucose stimulated insulin secretion (GSIS). Significance: Low fat vs. High fat=A; Low fat vs. High fat+hBD-2=B; High fat vs. High fat+hBD-2=C. (A) Oral glucose tolerance test of week 7. Two-way ANOVA with Tukey correction (matched values stacked). (B) Glucose-stimulated insulin secretion of week 7 taken during oGTT. Two-way ANOVA with Tukey correction (matched values stacked).

FIG. 13: Glucose homeostasis in mice treated for 10 weeks with low fat diet (low fat), high fat diet (high fat) or high fat diet and preventive treatment with defensin hBD-2 (high fat+hBD-2). (A) Insulin tolerance test (ITT). (B) HOMA-IR.

Significance: Low fat vs. High fat=A; Low fat vs. High fat+hBD-2=B;

High fat vs. High fat+hBD-2=C. (A) Insulin tolerance test of week 8. Two-way ANOVA with Tukey correction (matched values stacked). (B) Homeostasis Model Assessment (HOMA) of week 9. One-way ANOVA with Tukey correction.

Figure 14A:
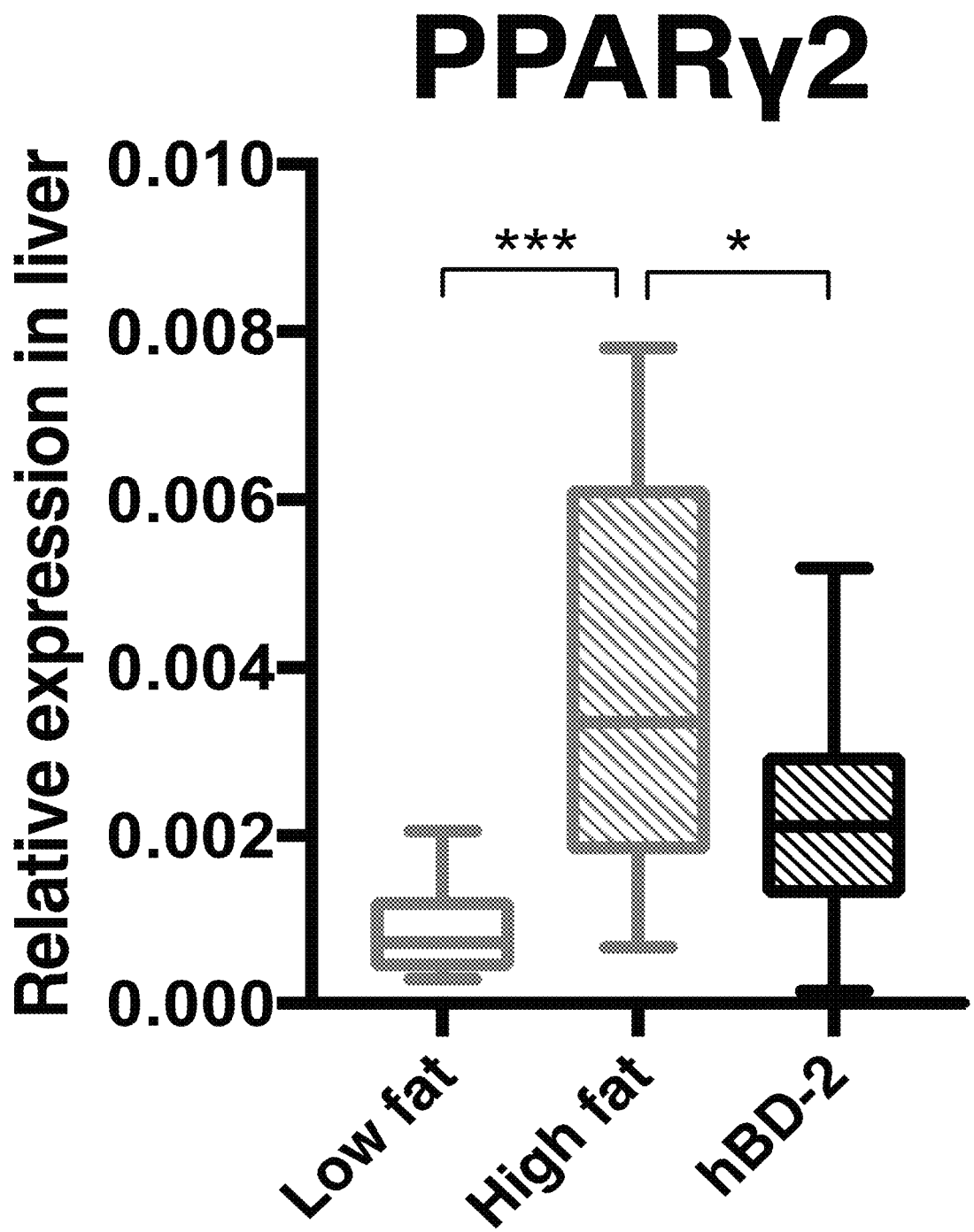
Figure 14B:
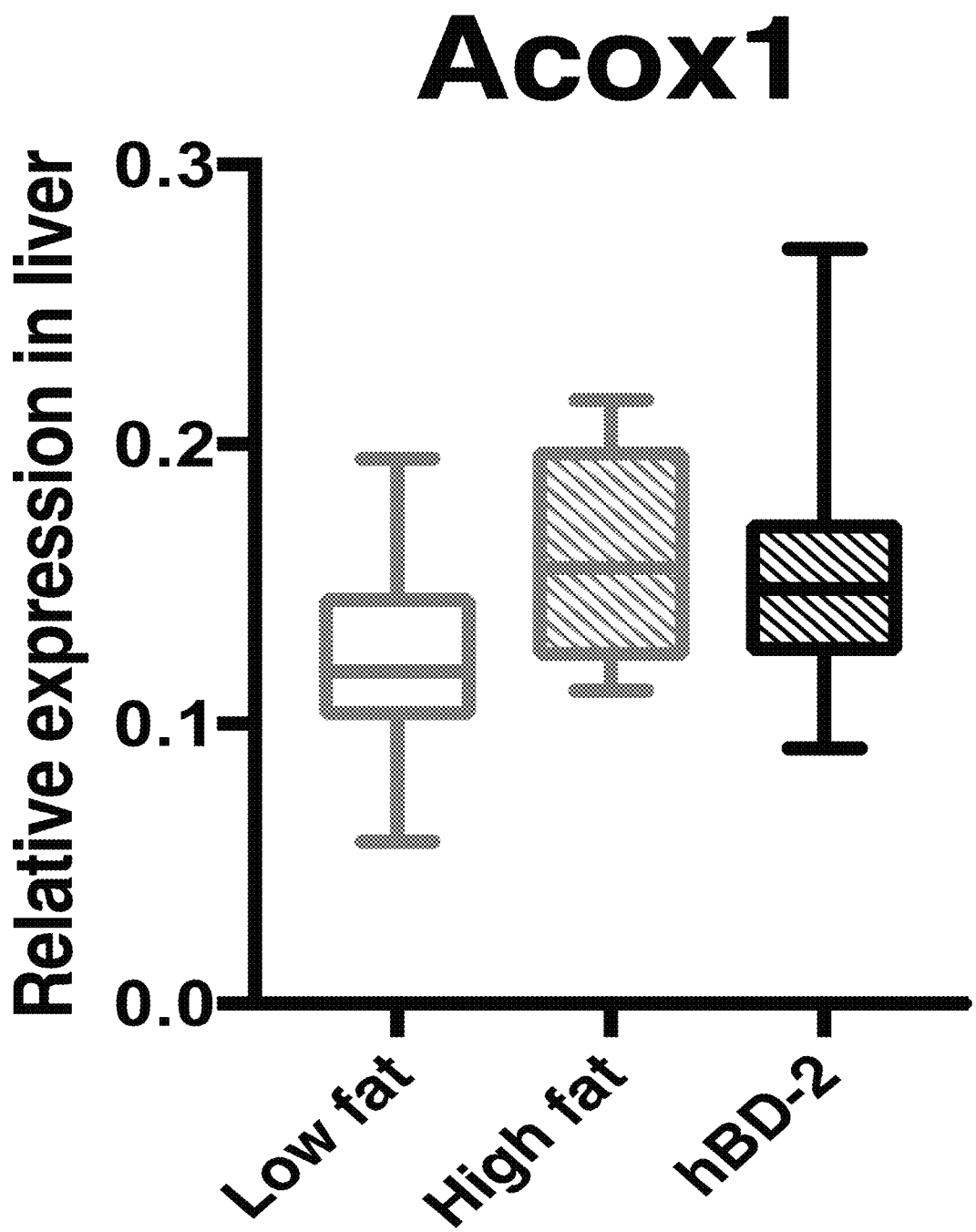

FIG. 14: Peroxisome proliferator activated receptor gamma (PPARγ2) expression (a) and Peroxisomal co-enzym A oxidase 1 (Acox1) expression (b) in the liver of mice treated for 10 weeks with low fat diet (low fat), high fat diet (high fat) or high fat diet and preventive treatment with defensin hBD-2 (high fat+hBD-2).

FIG. 15: Weight development (A) and weight change (B) over 10 week's treatment of mice with low fat diet (low fat), high fat diet (high fat) or high fat diet and intervention treatment with defensin hBD-2 (high fat+hBD-2). Significance: Low fat vs. High fat=A; Low fat vs. High fat+hBD-2=B; High fat vs. High fat+hBD-2=C. (A) Weight development. Two-way ANOVA with Tukey correction (matched values stacked). (B) Weight change from week 13 at the end of the run-in period and the following 10 weeks on experimental diets. Two-way ANOVA with Tukey correction (matched values stacked).

FIG. 16: Fat as a percent of total body weight (A) and change in fat % from week 0-4 in gram (B) over 10 weeks treatment of mice with low fat diet (low fat), high fat diet (high fat) or high fat diet and intervention treatment with defensin hBD-2 (hBD-2). Significance: Low fat vs. High fat=A; Low fat vs. High fat+hBD-2=B; High fat vs. High fat+hBD-2=C. (A) Fat percentage of total body weight in different weeks. Two-way ANOVA with Tukey correction (matched values stacked). (B) Change of fat percentage from end of the run-in and 4 weeks on experimental diets. One-way ANOVA with Tukey correction.

FIG. 17: Liver weight in gram (A) and weight of epididymal fat (eWAT) in gram (B) over 10 week's treatment of mice with low fat diet (low fat), high fat diet (high fat) or high fat diet and intervention treatment with defensin hBD-2 (hBD-2). Significance: Low fat vs. High fat=A; Low fat vs. High fat+hBD-2=B; High fat vs. High fat+hBD-2=C. (A) Weight of liver at termination. One-way ANOVA with Tukey correction. (B) Weight of epididymal adipose tissue (visceral fat) at termination. One-way ANOVA with Tukey correction.

FIG. 18: Glucose homeostasis in mice treated for 10 weeks with low fat diet (low fat), high fat diet (high fat) or high fat diet and intervention treatment with defensin hBD-2 (high fat+hBD-2). (A) Oral glucose tolerance test from cage 1 (B) Oral glucose tolerance test from mouse D1. (C) Insulin tolerance test (ITT). Significance: Low fat vs. High fat=A; Low fat vs. High fat+hBD-2=B; High fat vs. High fat+hBD-2=C. (A) Oral glucose tolerance tests repeated biweekly from end of run-in period (Week 13-0) showing the first cage of High fat+hBD-2 group. (B) Oral glucose tolerance tests repeated biweekly from end of run-in period (Week 13-0) showing ONLY mouse D1 of the High fat+hBD-2 group. (C) Insulin tolerance test of week 9. Two-way ANOVA with Tukey correction (matched values stacked).

Figure 19A:
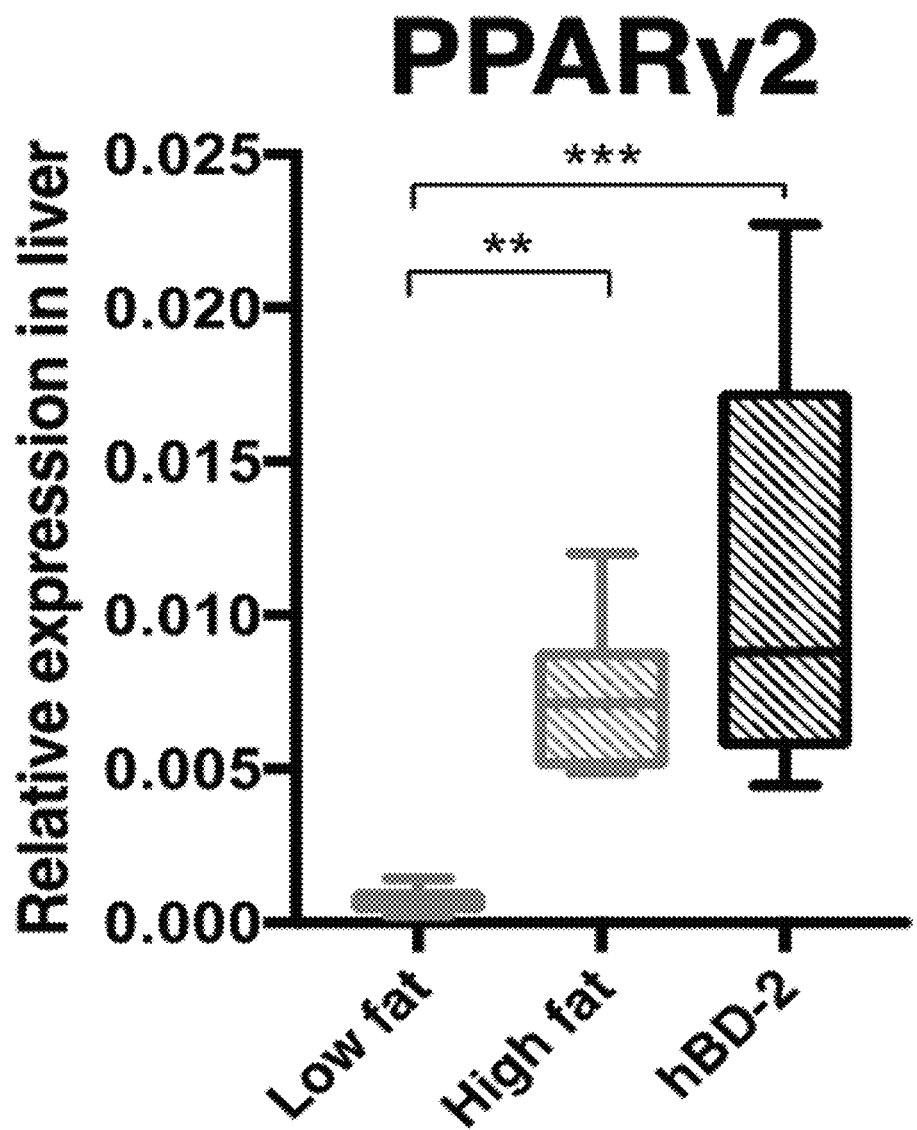
Figure 19B:
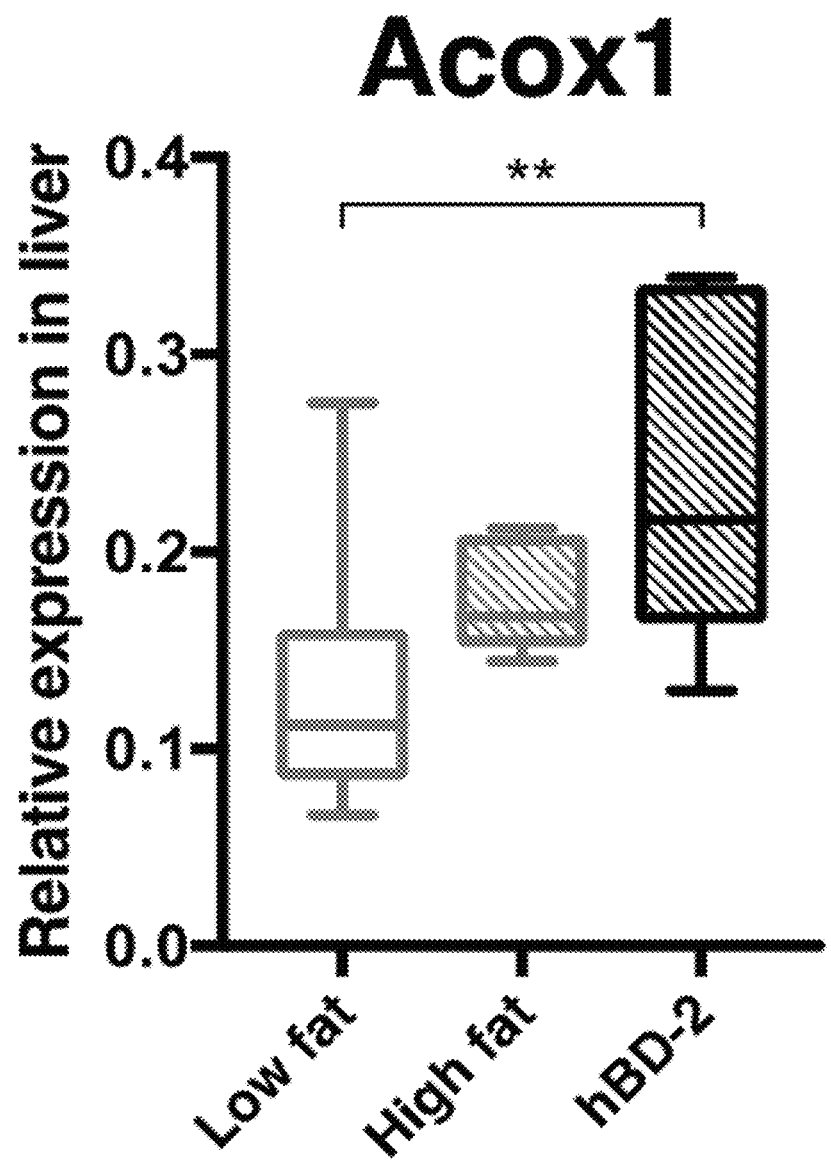

FIG. 19: Peroxisome proliferator activated receptor gamma (PPARγ2) expression (A) and Peroxisomal co-enzym A oxidase 1 (Acox1) expression (B) in the liver of mice treated over 10 week's treatment of mice with low fat diet (low fat), high fat diet (high fat) or high fat diet and intervention treatment with defensin hBD-2 (hBD-2).

Figure 20A:
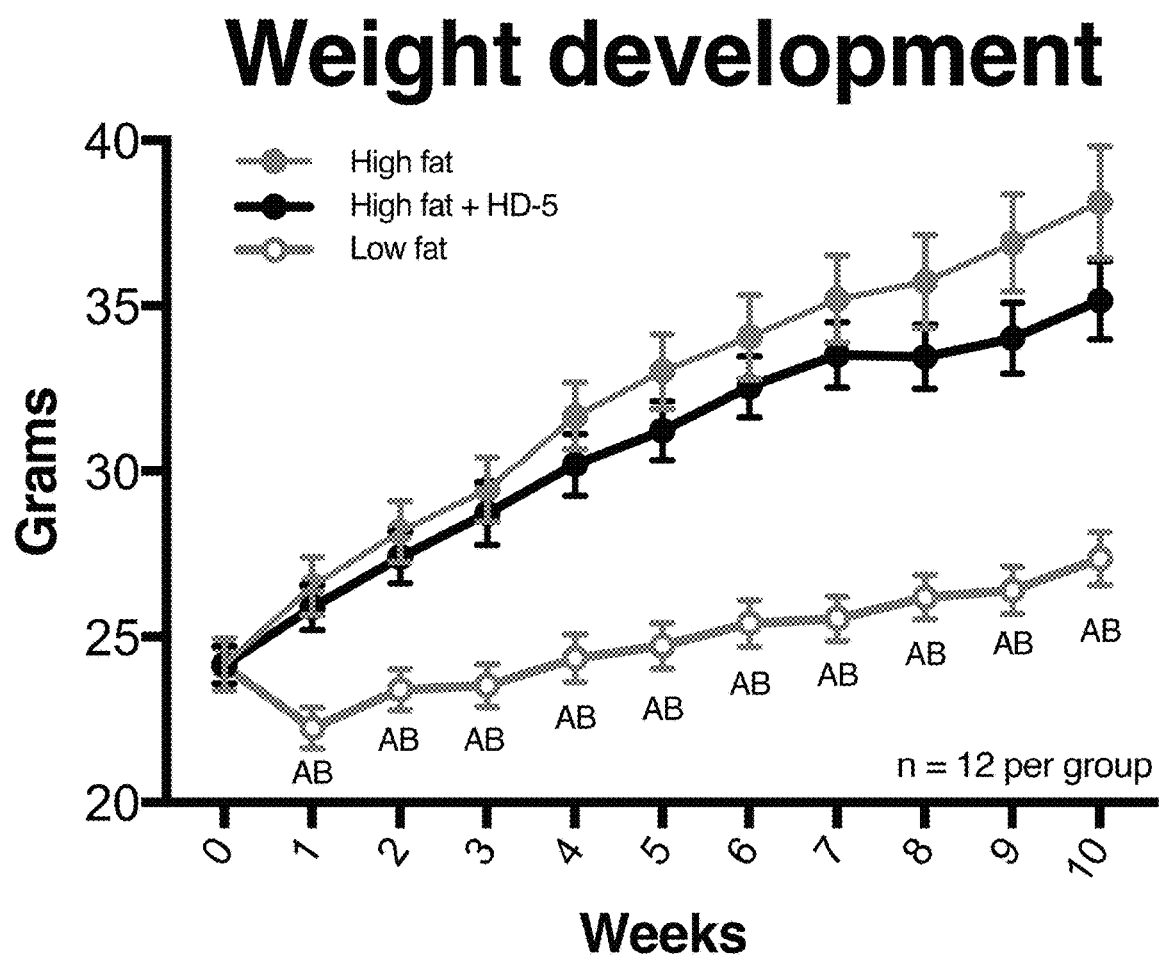
Figure 20B:
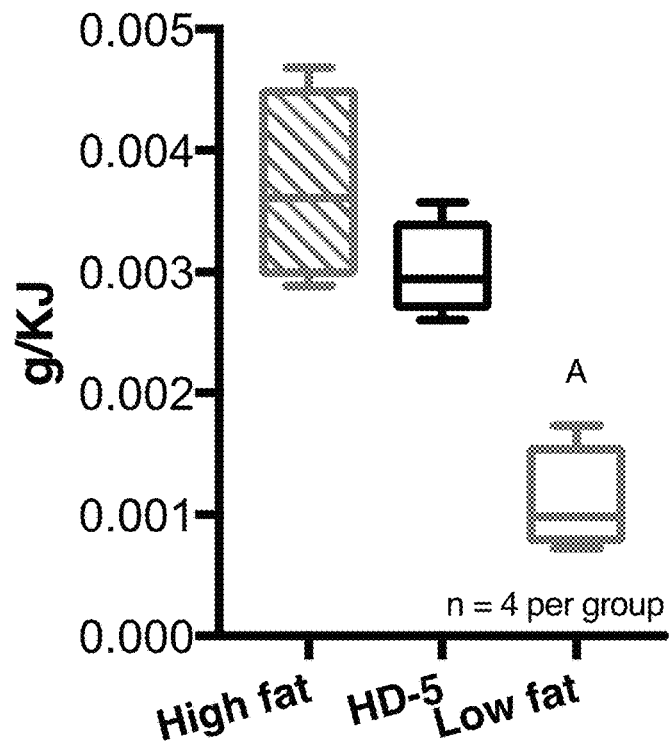
Figure 20C:
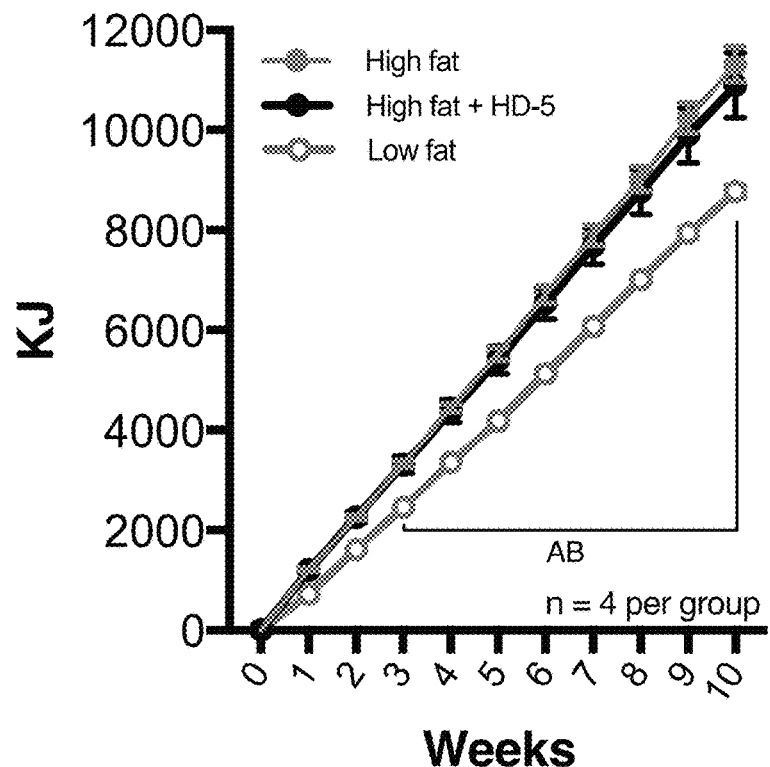

FIG. 20: Weight development (A) feed efficiency (B) and energy intake (C) over 10 week's treatment of mice with low fat diet (low fat), high fat diet (high fat) or high fat diet and preventive treatment with defensin HD5 (high fat+HD5). Significance: Low fat vs. High fat=A; Low fat vs. High fat+HD-5=B; High fat vs. High fat+HD-5=C. (A) Weight development. Two-way ANOVA with Tukey correction (matched values stacked). (B) Feed efficiency (gram of gained weight adjusted for average food intake in the cage). One-way ANOVA Tukey correction NB! n=4 due to co-caging. (C) Energy intake. Two-way ANOVA with Tukey correction (matched values stacked).

Figure 21A:
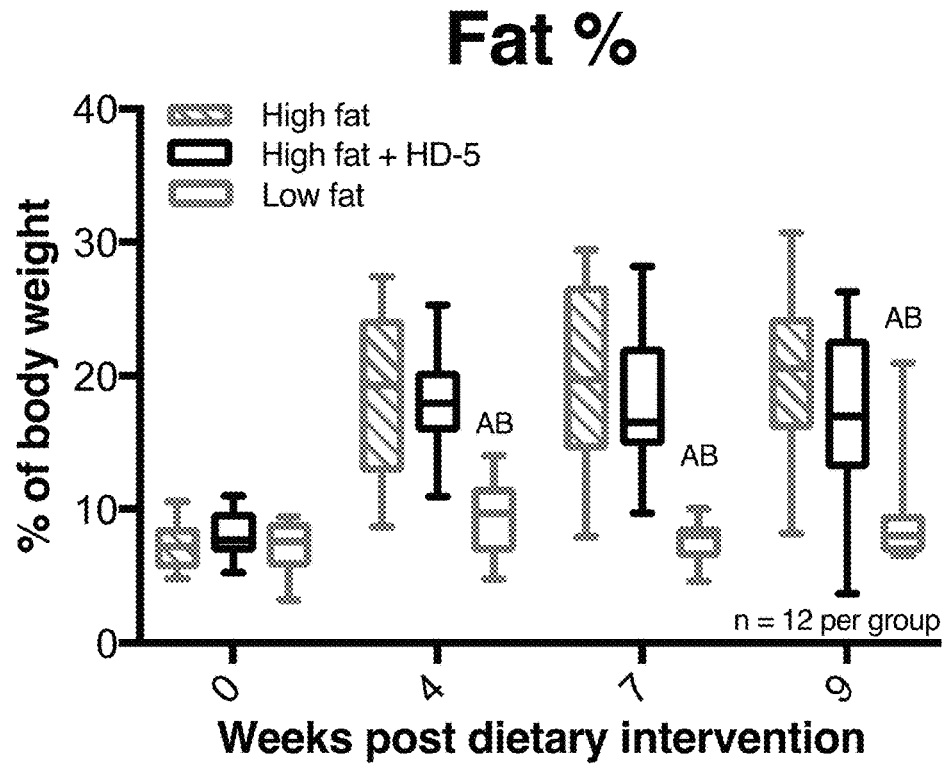
Figure 21B:
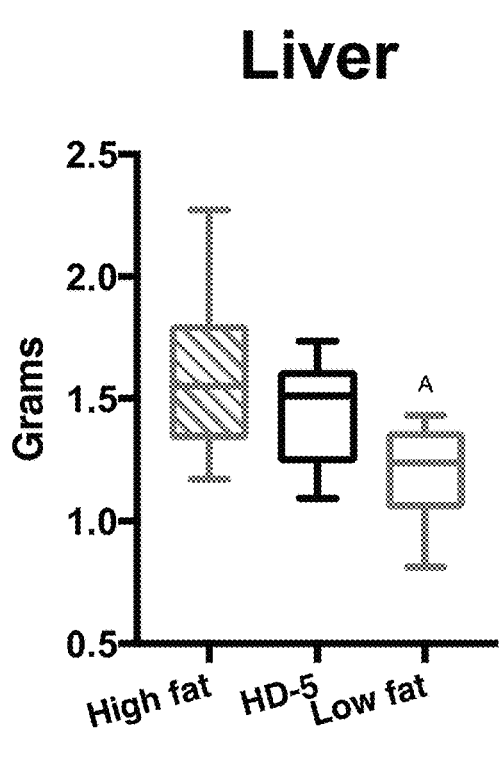
Figure 21C:
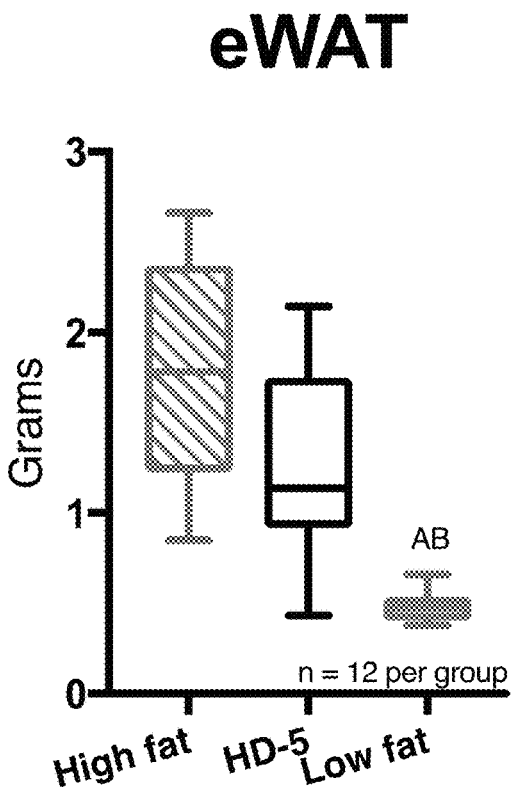

FIG. 21: Fat as a percent of total body weight (A), liver weight in gram (B) and weight of epididymal fat (eWAT) in gram (C) over 10 week's treatment of mice with low fat diet (low fat), high fat diet (high fat) or high fat diet and preventive treatment with defensin HD5 (HD5). Significance: Low fat vs. High fat=A; Low fat vs. High fat+HD-5=B; High fat vs. High fat+HD-5=C. (A) Fat percentage of total body weight in different weeks. Two-way ANOVA with Tukey correction (matched values stacked). (B) Weight of the liver at termination. One-way ANOVA Tukey correction. (C) Weight of epididymal adipose tissue (visceral AT) at termination. One-way ANOVA with Tukey correction.

FIG. 22: Glucose homeostasis in mice treated for 10 weeks with low fat diet (low fat), high fat diet (high fat) or high fat diet and preventive treatment with defensin HD5 (high fat+HD5). (A) Oral glucose tolerance test. (B) Glucose stimulated insulin secretion (GSIS). Significance: Low fat vs. High fat=A; Low fat vs. High fat+HD-5=B; High fat vs. High fat+HD-5=C. (A) Oral glucose tolerance test of week 7. Two-way ANOVA with Tukey correction (matched values stacked). (B) Glucose-stimulated insulin secretion of week 7 taken during oGTT. Two-way ANOVA with Tukey correction (matched values stacked).

FIG. 23: Glucose homeostasis in mice treated for 10 weeks with low fat diet (low fat), high fat diet (high fat) or high fat diet and preventive treatment with defensin HD5 (high fat+HD5). (A) Insulin tolerance test (ITT). (B) HOMA-IR. Significance: Low fat vs. High fat=A; Low fat vs. High fat+HD-5=B; High fat vs. High fat+HD-5=C. (A) Insulin tolerance test of week 8. Two-way ANOVA with Tukey correction (matched values stacked). (B) Homeostasis Model Assessment (HOMA) of week 9. One-way ANOVA with Tukey correction.

FIG. 24: Peroxisome proliferator activated receptor gamma (PPARγ2) expression (A) and Peroxisomal co-enzym A oxidase 1 (Acox1) expression (B) in the liver of mice treated for 10 weeks with low fat diet (low fat), high fat diet (high fat) or high fat diet and preventive treatment with defensin HD5 (high fat+HD5).

FIG. 25: Weight development (A) and weight change (B) over 10 week's treatment of mice with low fat diet (low fat), high fat diet (high fat) or high fat diet and intervention treatment with defensin HD5 (high fat+HD5). Significance: Low fat vs. High fat=A; Low fat vs. High fat+HD-5=B; High fat vs. High fat+HD-5=C. (A) Weight development. Two-way ANOVA with Tukey correction (matched values stacked). (B) Weight change from week 13 at the end of the run-in period and the following 10 weeks on experimental diets. Two-way ANOVA with Tukey correction (matched values stacked).

FIG. 26: Fat as a percent of total body weight (A) and change in fat % from week 0-4 in gram (B) over 10 week's treatment of mice with low fat diet (low fat), high fat diet (high fat) or high fat diet and intervention treatment with defensin HD5 (HD-5). Significance: Low fat vs. High fat=A; Low fat vs. High fat+HD-5=B; High fat vs. High fat+HD-5=C. (A) Fat percentage of total body weight in different weeks. Two-way ANOVA with Tukey correction (matched values stacked). (B) Change of fat percentage from end of the run-in and to week 4 on experimental diets. One-way ANOVA with Tukey correction.

FIG. 27: Liver weight in gram (A) and weight of epididymal fat (eWAT) in gram (B) over 10 week's treatment of mice with low fat diet (low fat), high fat diet (high fat) or high fat diet and intervention treatment with defensin HD5 (HD-5). Significance: Low fat vs. High fat=A; Low fat vs. High fat+HD-5=B; High fat vs. High fat+HD-5=C. (A) Weight of liver at termination. One-way ANOVA with Tukey correction. (B) Weight of epididymal adipose tissue (visceral AT) at termination. One-way ANOVA with Tukey correction.

FIG. 28: Glucose homeostasis in mice treated for 10 weeks with low fat diet (low fat), high fat diet (high fat) or high fat diet and intervention treatment with defensin HD5 (high fat+HD5). (A) Oral glucose tolerance test from cage 2 (B) Insulin tolerance test (ITT). Significance: Low fat vs. High fat=A; Low fat vs. High fat+HD-5=B; High fat vs. High fat+HD-5=C. (A) Oral glucose tolerance tests repeated biweekly from end of run-in period (Week 13-0) showing the second cage of High fat+HD-5 group. (B) Insulin tolerance test of week 9. Two-way ANOVA with Tukey correction (matched values stacked).

FIG. 29: Peroxisome proliferator activated receptor gamma (PPARγ2) expression (a) and Peroxisomal co-enzym A oxidase 1 (Acox1) expression (b) in the liver of mice over 10 week's treatment of mice with low fat diet (low fat), high fat diet (high fat) or high fat diet and intervention treatment with defensin HD5 (HD-5).

Figure 30A:
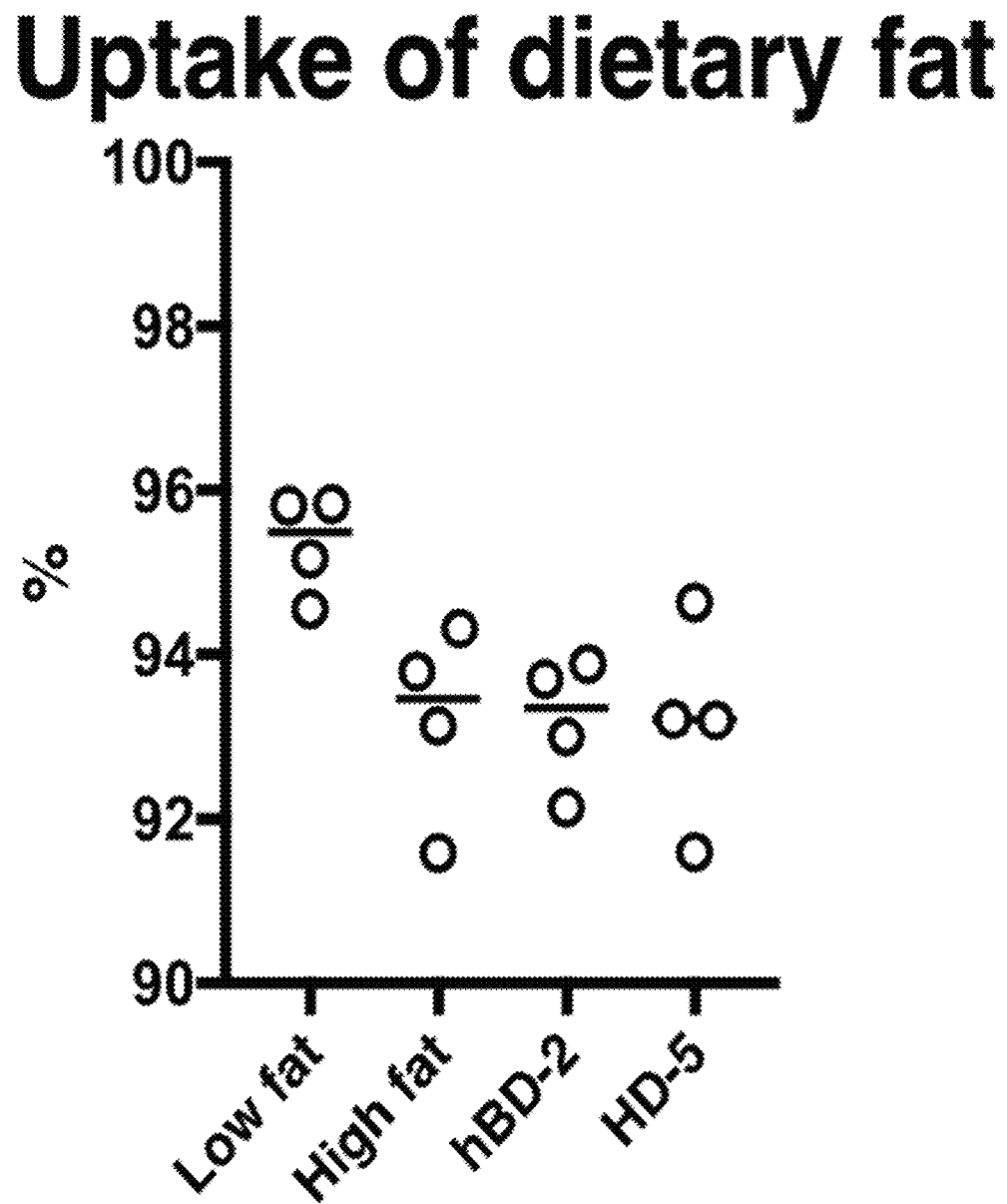

FIG. 30: Uptake of dietary fat (A) and fecal fat content (B) in mice treated for 10 weeks with low fat diet (low fat), high fat diet (high fat), high fat diet and preventive treatment with defensin hBD-2 (high fat+hBD-2) or preventive treatment with defensin HD5 (high fat+HD5).

Figure 31:
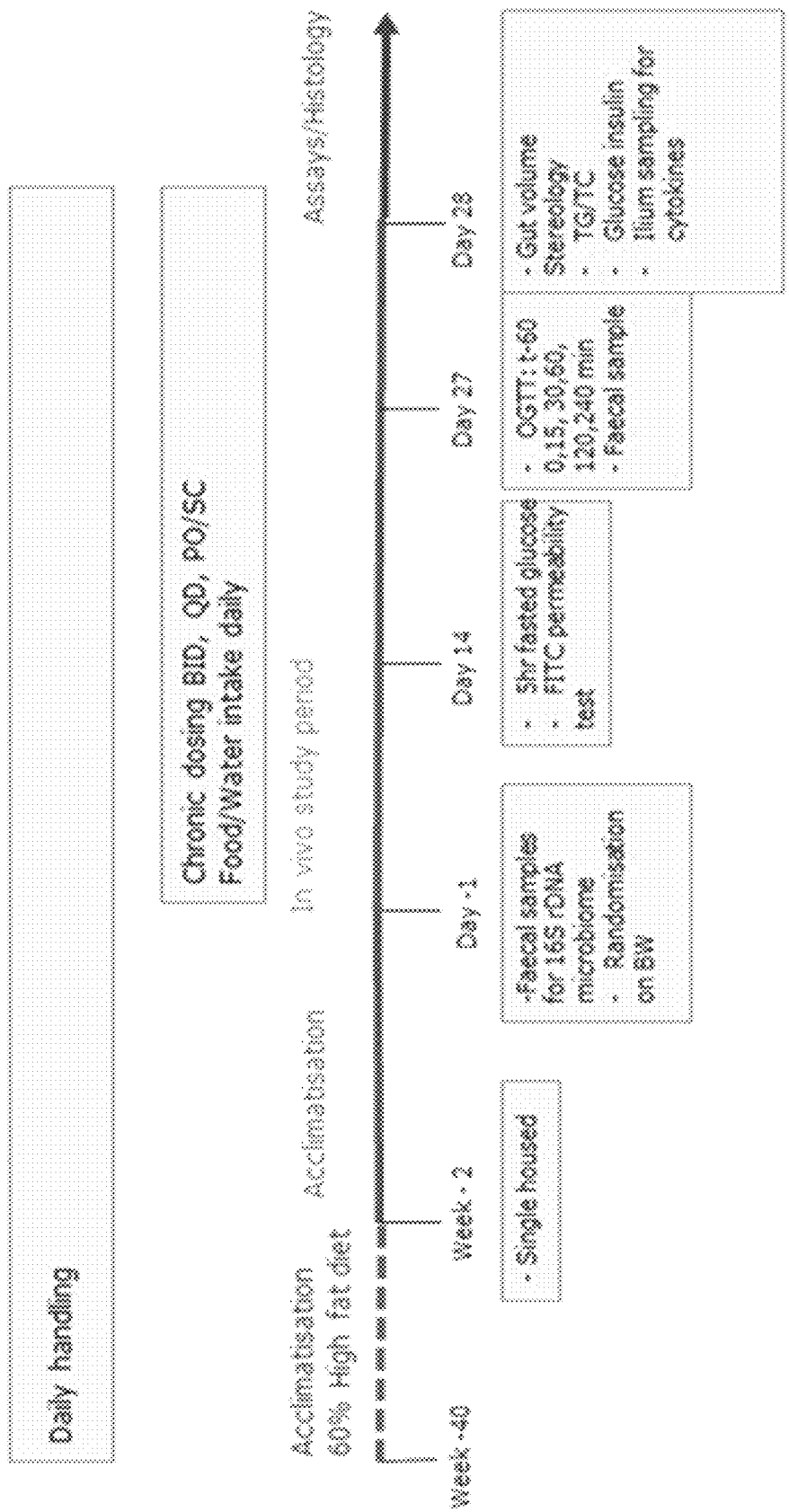

FIG. 31: Schematic outline of the experimental set up for investigating the effects of a GLP-1 analog (Liraglutid) on mouse gut inflammation and microbiota. At week −40, the C57/Bl/6J DIO mice arrived. The mice were fed a high fat diet 60% fat, SSNIFF (Diet #D12492) or purina chow for 38 weeks to achieve an average body weight of 55 gram. From week −2 the mice were single housed. Faecal samples were collected on day −1 and 27 for 16S RNA analysis. Samples from ilium were collected 2 cm from caecum at day 28.

Figure 32A:
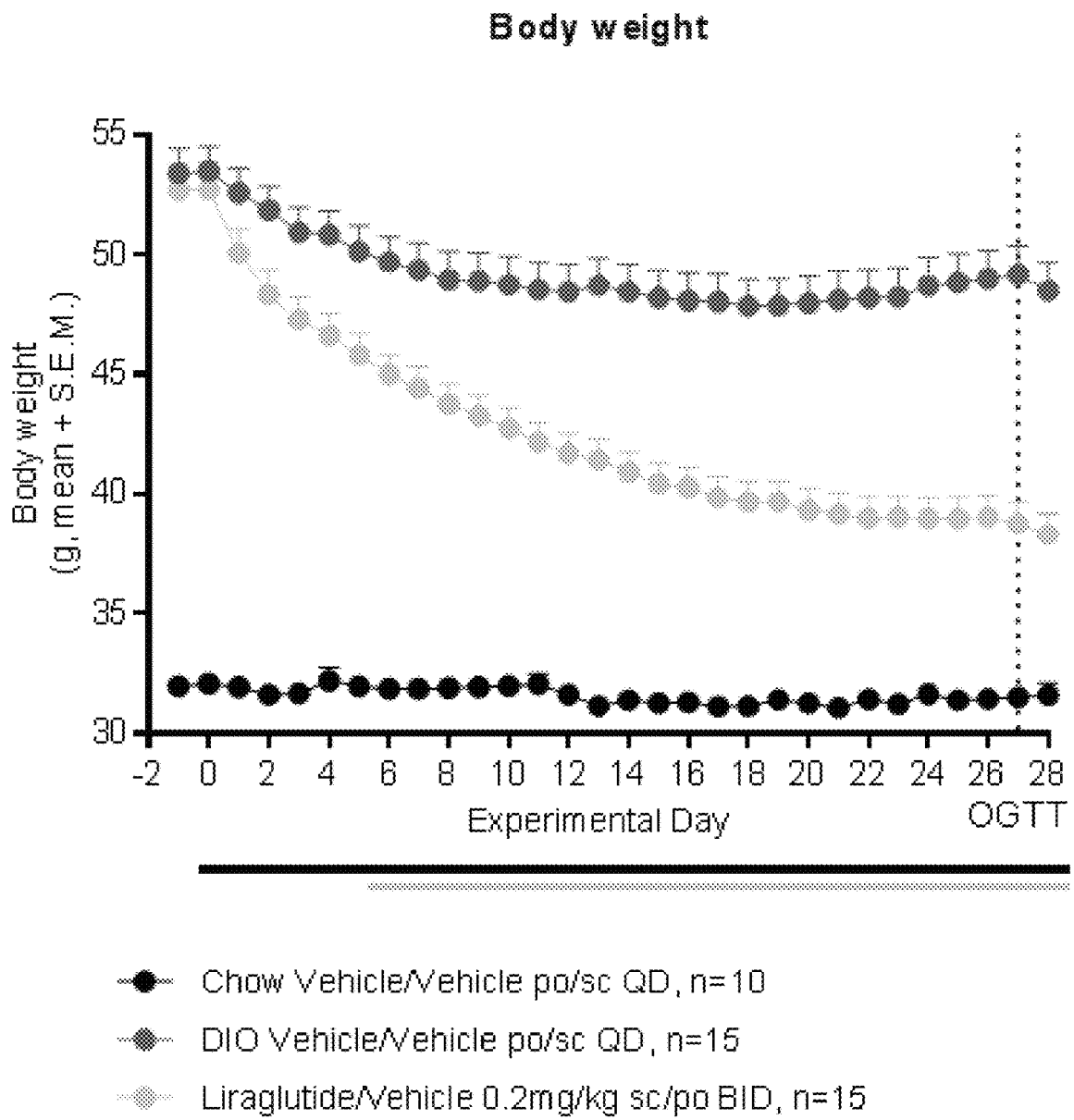
Figure 32B:
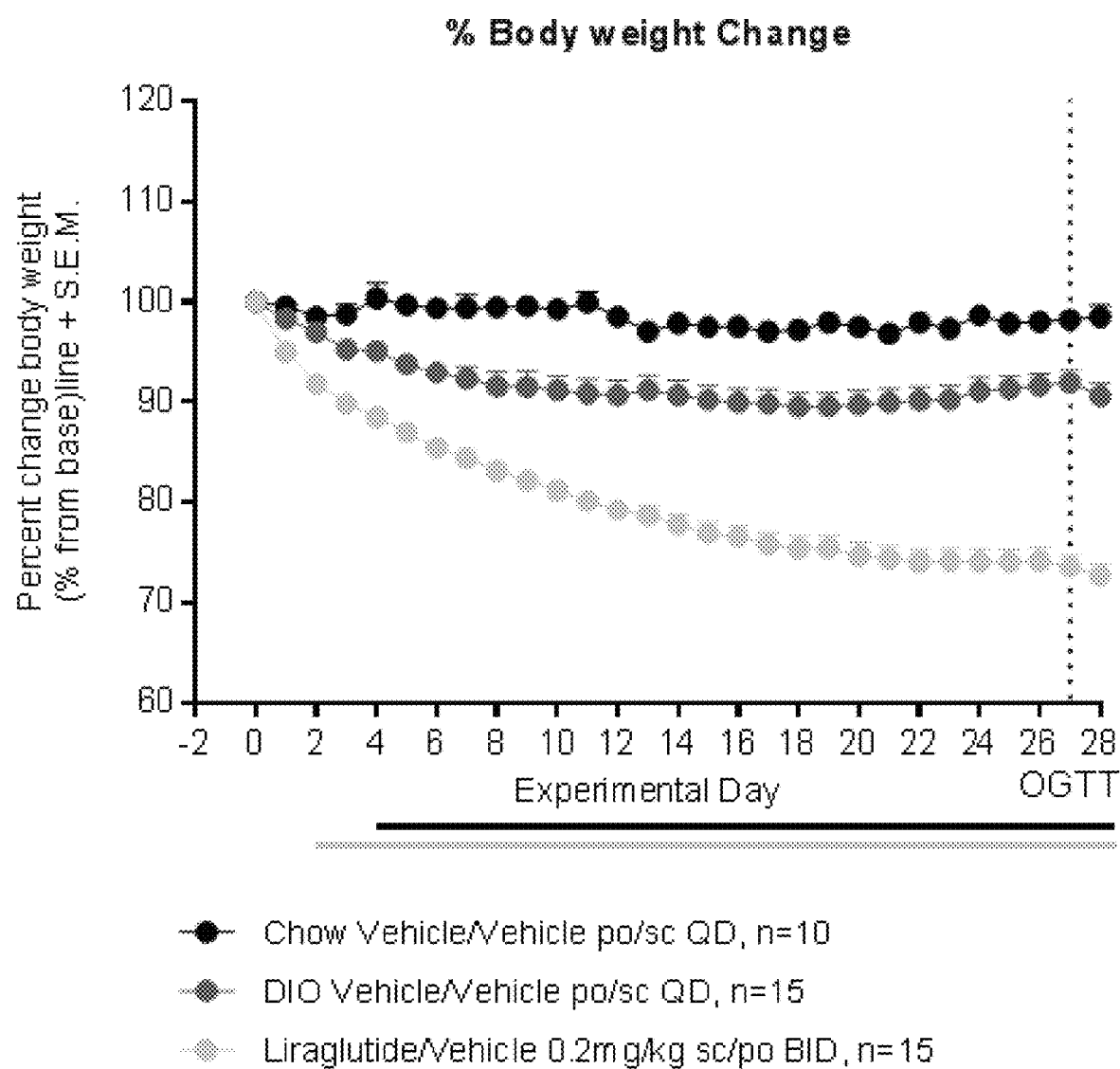

FIG. 32. Weight loss in gram and as a % of body weight during 4 week's treatment with HFD plus a GLP-1 analog following 38 weeks on a HFD.

Figure 33:
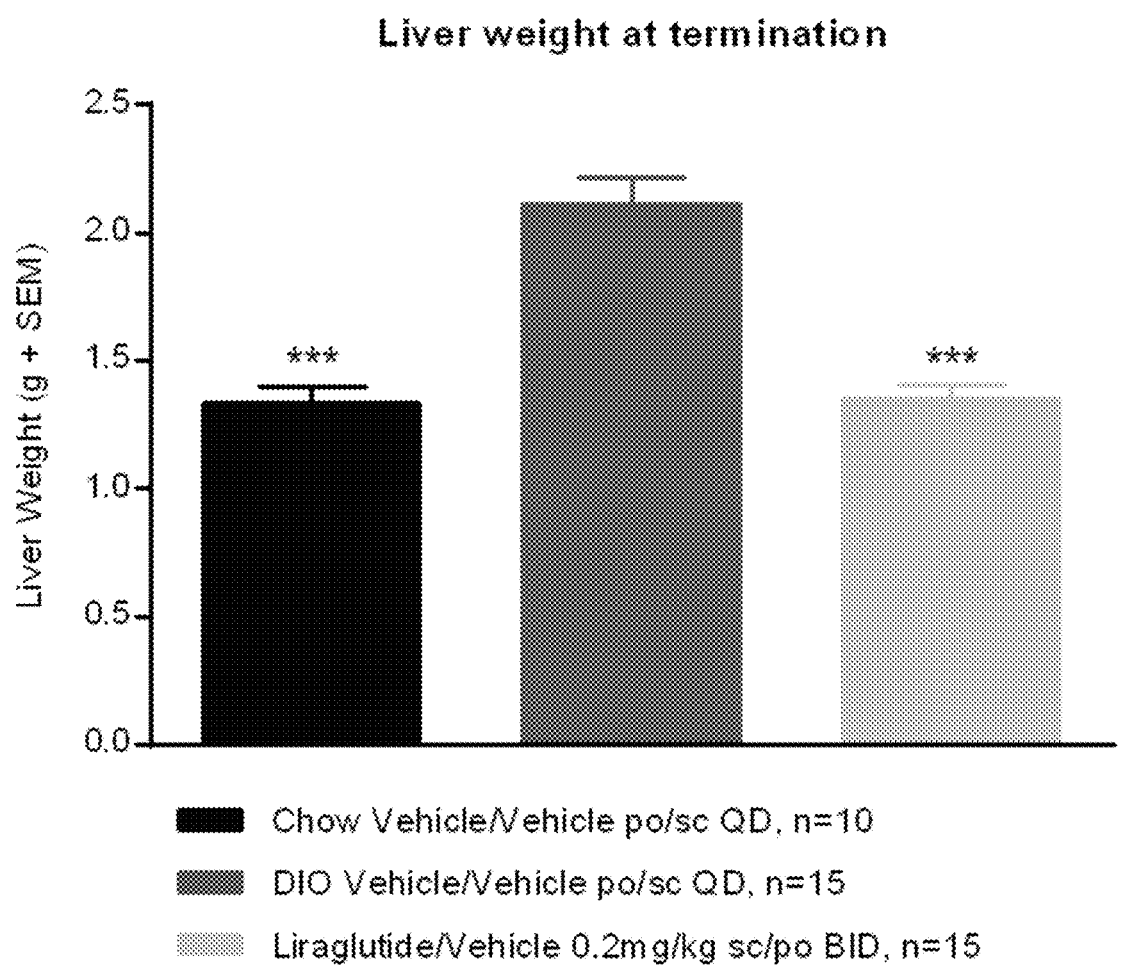

FIG. 33. Liver weight in gram at termination following 38 weeks on a HFD and 4 weeks on a HFD plus a GLP-1 analog.

Figure 34:
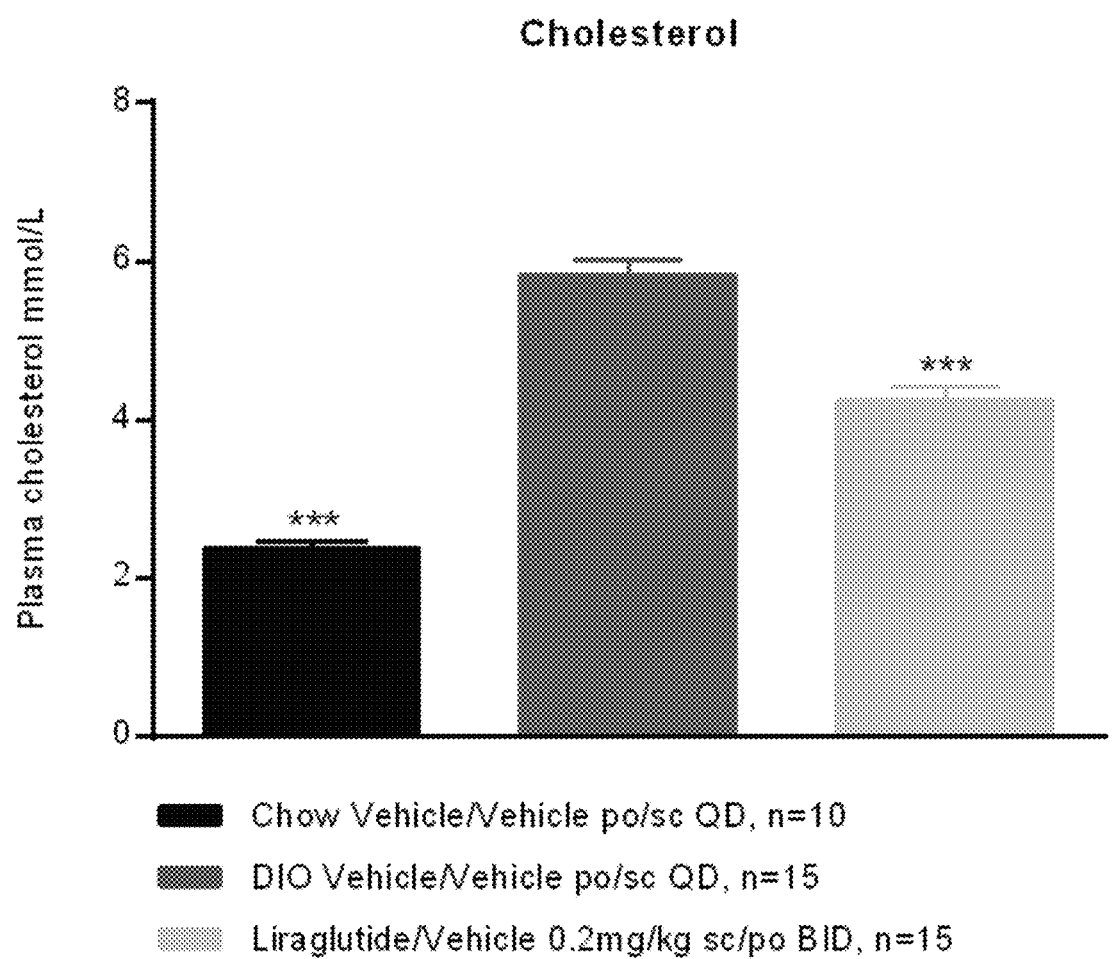

FIG. 34. Plasma cholesterol concentrations at termination following 38 weeks on a HFD and 4 weeks on a HFD plus a GLP-1 analog.

Figure 35:
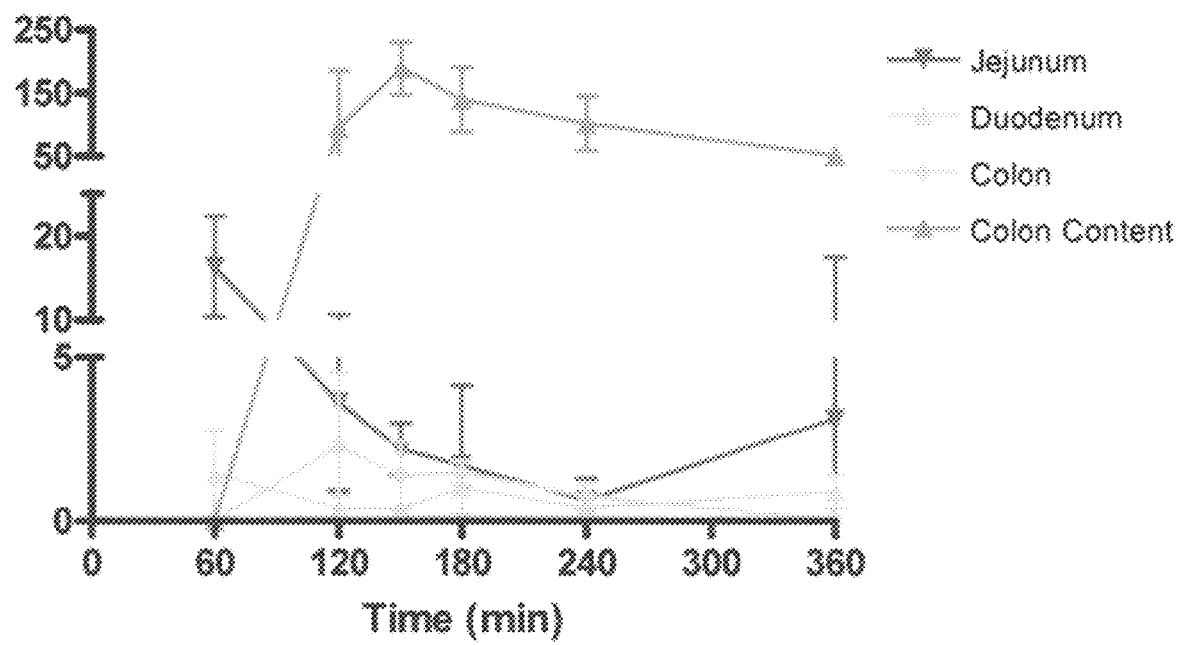

FIG. 35. Pharmacokinetic data following oral administration of 4 mg/kg hBD-2 to female NMRI mice. The Y-axis shows hBD-2 in μg/g tissue. The results are given as group mean+/−SEM.

Figure 36:
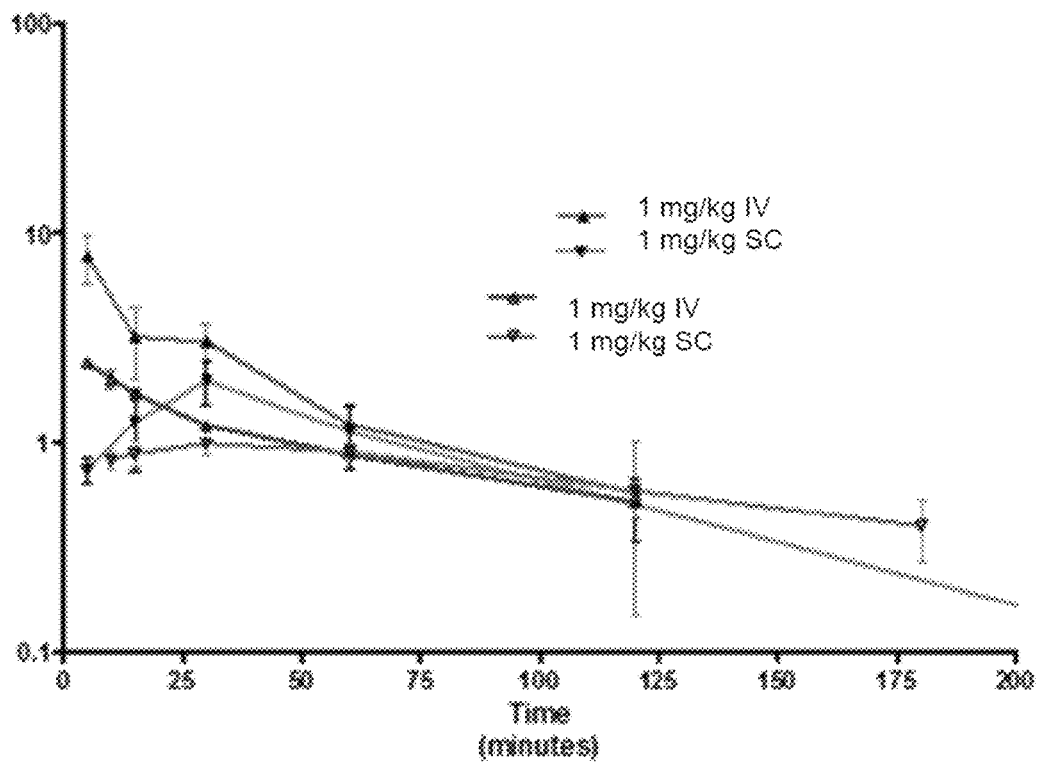

FIG. 36. Pharmacokinetic data for hBD-2 following subcutaneous (SC) and intravenous (IV) administration of 1 mg/kg respectively. The Y-axis shows hBD-2 in μg/mL. The different curves represent different experiments and detection methods (HPLC and ELISA).

Figure 37:
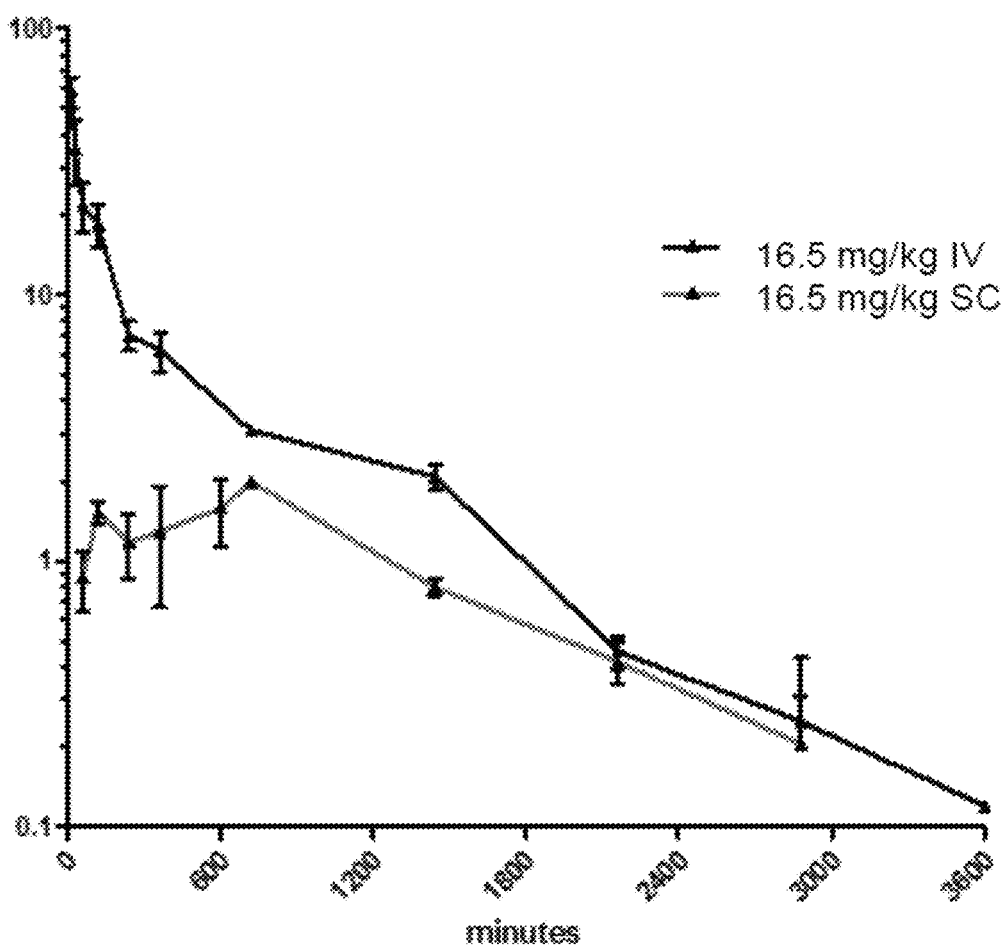

FIG. 37. Pharmacokinetic data for "hBD-2-albumin fusion N-terminal" following subcutaneous and intravenous administration of 16.5 mg/kg respectively. The Y-axis shows the concentration of the fusion protein in μg/mL. The results are the mean of 4 mice/sampling time+/−SD.

Figure 38:
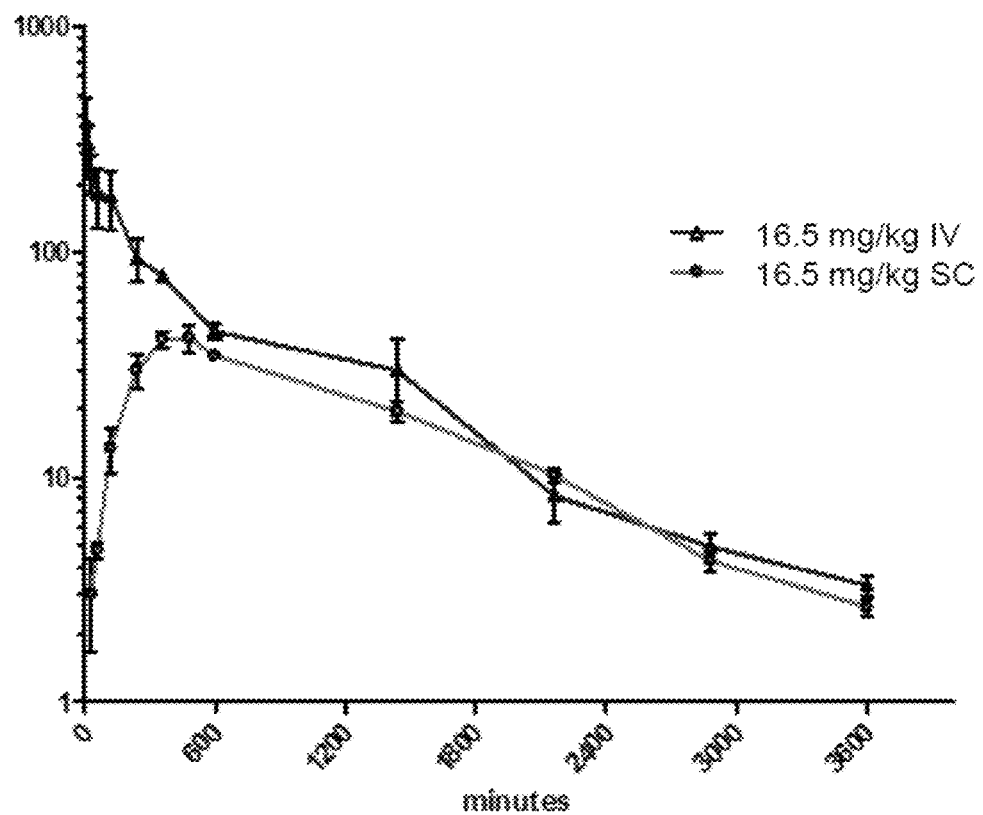

FIG. 38. Pharmacokinetic data for "hBD-2-albumin fusion C-terminal" following subcutaneous and intravenous administration of 16.5 mg/kg respectively. The Y-axis shows the concentration of the fusion protein in μg/mL. The results are the mean of 4 mice/sampling time+/−SD.

DETAILED DESCRIPTION

The invention is as defined in the claims.

Definitions

Cathelicidin: The term refers to cathelicidin-related antimicrobial peptides, which are a family of polypeptides found in lysosomes of macrophages and polymorphonuclear leukocytes PMNs, and keratinocytes. Cathelicidins serve a critical role in mammalian innate immune defense against invasive bacterial infection. The cathelicidin family of peptides are classified as antimicrobial peptides, a family which also includes the defensins. Members of the cathelicidin family of antimicrobial polypeptides are characterized by a highly conserved region (cathelin domain) and a highly variable cathelicidin peptide domain. An example of cathelicidin is the human cathelicidin, from which LL-37 (SEQ ID NO: 16) is derived.

Defensin: The term "defensin" as used herein refers to polypeptides recognized by a person skilled in the art as belonging to the defensin class of antimicrobial peptides. The defensins belong to the alpha defensin class or to the beta defensin class. Examples of defensins include human intestinal alpha defensin 5 (HD5; SEQ ID NO. 8); human alpha defensin 6 (HD6; SEQ ID NO. 9); human neutrophil peptide 1 (HNP-1; SEQ ID NO. 20); human neutrophil peptide 2 (HNP-2; SEQ ID NO. 18); human neutrophil peptide 3 (HNP-3; SEQ ID NO. 19), all belonging to the alpha defensin class; and also human beta defensin 1 (hBD1; SEQ ID NO. 4); human beta defensin 2 (hBD-2; SEQ ID NO. 5); human beta defensin 3 (hBD3; SEQ ID NO. 6); human beta defensin 4 (hBD4; SEQ ID NO. 7), chimpanzee beta defensin 2 (SEQ ID NO: 10), macaque beta defensin 2 (SEQ ID NO: 11), orangutan beta defensin 2 (SEQ ID NO: 3), mouse beta defensin 3 (SEQ ID NO: 12), horse beta defensin 2 (SEQ ID NO: 13), porcine beta defensin 1 (SEQ ID NO: 14), goat beta defensin 2 (SEQ ID NO: 15), bovine beta defensin 2 (SEQ ID NO: 1), chicken beta defensin 2 (SEQ ID NO: 2) belonging to the beta defensin class.

Defensins are expressed as precursors and are processed by cleavage of the signal peptide and in some cases propeptides as well before secretion into the extracellular space. The above-identified sequences represent the predicted mature bioactive defensins. It will be understood by one of skill in the art that processing may differ from cell to cell and that the resulting secreted mature peptide may differ by one or two C- or N-terminal amino acids from the predicted sequences and still retain their bioactivity. Gut:

The gut is a tube used by animals to transfer food to the digestion organs and it includes the digestion organs themselves. Human gut as used herein refers to a digestive system composed of mouth, oesophagus, stomach, duodenum, jejunum, ileum, cecum, colon, rectum, and anal canal.

Glucagon-like peptide-1 (GLP-1). GLP-1 is a neuropeptide and an incretin derived from the transcription product of the proglucagon gene. The major source of GLP-1 in the periphery is the intestinal L cell, that secretes GLP-1 as a gut hormone. The biologically active forms of GLP-1 are: GLP-1-(7-37) and GLP-1-(7-36)NH2. These peptides result from selective cleavage of the proglucagon molecule.

GLP-1 secretion by ileal L cells is dependent on the presence of nutrients in the lumen of the small intestine. The secretagogues (agents that cause or stimulate secretion) of this hormone include major nutrients like carbohydrates, proteins and lipids. Once in the circulation, GLP-1 has a half-life of less than 2 minutes, due to rapid degradation by the enzyme dipeptidyl peptidase-4.

GLP-1 is a potent antihyperglycemic hormone, inducing the beta cells of the pancreas to release the hormone insulin in response to rising glucose, while suppressing glucagon secretion. Such glucose-dependent action is particularly attractive because an unregulated release of insulin, when the plasma glucose concentration is in the normal fasting range, or poorly-timed insulin injections, can cause a dangerous fall in blood glucose—hypoglycemia. This does not happen as a result of GLP-1 because GLP-1 no longer stimulates the β-cells to release more insulin when blood glucose levels are in the fasting range. In addition, GLP-1 inhibits gastric secretion and motility. This delays and protracts carbohydrate absorption and contributes to a satiating effect.

Liraglutide (NN2211) is a long-acting glucagon-like peptide-1 receptor agonist, binding to the same receptors as does the endogenous metabolic hormone GLP-1 that stimulates insulin secretion.

Other GLP-1 analogs include exenatide, lixisenatide, albiglutide, and dulaglutide.

Identity: The relatedness between two amino acid sequences or between two nucleotide sequences is described by the parameter "identity".

The degree of identity between two amino acid sequences is determined using the Needleman-Wunsch algorithm (Needleman and Wunsch, 1970, *J. Mol. Biol.* 48: 443-453) as implemented in the Needle program of the EMBOSS package (Rice et al., 2000, emboss.org), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment−
Total Number of Gaps in Alignment).

Treatment: The terms "treatment" and "treating" as used herein refer to the management and care of a patient for the purpose of combating a condition, disease or disorder. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering, reducing or delaying the development of the condition, disease or disorder, and includes the administration of the active compounds to prevent or reduce the risk of the onset of symptoms or complications. The patient to be treated is preferably a mammalian, in particular a human being. The patients to be treated can be of various ages.

Subject, patient: A subject is an individual of one of the species of mammals disclosed herein. A patient is a subject, which has been diagnosed with a particular disorder.

Mammalian Alpha and Beta Defensins

This disclosure relates to uses of mammalian alpha and/or beta defensins and/or cathelicidin, such as bovine, porcine, sheep, goat, mouse, monkey, horse, or human beta defensins, more preferably Hominidae defensins, more preferably human alpha and/or beta defensin and/or human cathelicidin in the treatment of liver, pancreatic or biliary tract disorders and certain metabolic disorders. In another embodiment, the disclosure relates to uses of GLP-1 analogs, such as liraglutide, in the treatment of liver, pancreatic or biliary tract disorders and certain metabolic disorders.

In an embodiment, the mammalian alpha and/or beta defensins and/or cathelicidin have a degree of identity of at least 80%, preferably at least 85%, more preferably at least 90%, and most preferably at least 95% to any of the amino acid sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO: 14, SEQ ID NO: 15, SEQ ID NO: 16 and/or SEQ ID NO:17. In another embodiment, a defensin differs from one of the SEQ ID NO:1-15 or 17 by less than 10, such as less than 8, for example less than 5, such as less than 4, for example less than 3, such as less than 2 amino acids.

In a preferred embodiment, the human alpha defensins consist of alpha defensin 5 (SEQ ID NO: 8) and/or alpha defensin 6 (SEQ ID NO:9). In a preferred embodiment, the mammalian beta defensins consist of human beta defensin 1 (SEQ ID NO:4), human beta defensin 2 (SEQ ID NO:5), human beta defensin 3 (SEQ ID NO:6), human beta defensin 4 (SEQ ID NO:7) and/or truncated human beta defensin 2 (SEQ ID NO: 17). In another preferred embodiment, the cathelicidin consists of human cathelicidin or human LL37 (SEQ ID NO: 16) derived from cathelicidin. In a preferred embodiment, the GLP-1 analog is liraglutide.

In a preferred embodiment, a human alpha defensin has a degree of identity of at least 80%, preferably at least 85%, more preferably at least 90%, and most preferably at least 95% to the amino acid sequence of SEQ ID NO: 8. In a preferred embodiment, the human mammalian alpha defensins consist of alpha defensin 5 (SEQ ID NO: 8). In a preferred embodiment, the human beta defensin has a degree of identity of at least 80%, preferably at least 85%, more preferably at least 90%, and most preferably at least 95% to the amino acid sequence of SEQ ID NO: 5. In a preferred embodiment, the human beta defensin consists of human beta defensin 2 (SEQ ID NO: 5). In a preferred embodiment, the human cathelicidin has a degree of identity of at least 80%, preferably at least 85%, more preferably at least 90%, and most preferably at least 95% to the amino acid sequence of SEQ ID NO: 16. In a preferred embodiment, the human cathelicidin consists of human LL37 (SEQ ID NO: 16).

For species other than human beings, the subjects are preferably treated with a defensin or a cathelicidin originating from the same or a related species or a defensin or a cathelicidin sharing at least 80%, preferably at least 85%, more preferably at least 90%, and most preferably at least 95% to the amino acid sequence of a defensin or a cathelicidin from that same species (for example the defensin having an amino acid sequence selected from SEQ ID NO: 1-3, 10-15).

In yet another embodiment, the mammalian alpha defensins comprise of human alpha defensins and/or mouse alpha defensins, and functionally equivalent variants thereof. Preferably, the mammalian alpha defensin consist of human alpha defensin 5, human alpha defensin 6 and functionally equivalent variants thereof. More preferably, the mammalian alpha defensins consist of human alpha defensin 5, and functionally equivalent variants or orthologues thereof.

In yet a further embodiment, the mammalian beta defensins consist of human beta defensins and/or mouse beta defensins, and functionally equivalent variants thereof. Preferably, the mammalian beta defensins consist of human beta defensin 1, human beta defensin 2, human beta defensin 3, human beta defensin 4, Chimpanzee beta defensin 2, Macaque beta defensin 2, and mouse beta defensin 3, orangutan beta defensin 2, horse beta defensin 2, porcine beta defensin 1, goat beta defensin 2, bovine beta defensin 2, or truncated human beta defensin 2 and functionally equivalent variants thereof. More preferably, the mammalian beta defensins comprise of human beta defensin 1, human beta defensin 2, human beta defensin 3, human beta defensin 4, truncated human beta defensin 2 and functionally equivalent variants thereof. Even more preferably, the mammalian beta defensins consist of human beta defensin 2, and functionally equivalent variants or orthologues thereof.

In yet a further embodiment, the mammalian cathelicidin consists of human cathelicidin, and functionally equivalent variants thereof. Preferably, the mammalian cathelicidin consists of human LL37.

In one embodiment, the methods comprise administration of an effective amount of at least one mammalian α-defensin to a subject in need of such treatment. In other embodiments, the provided methods comprise administration of an effective amount of at least one mammalian β-defensin to a subject in need of such treatment. In a further embodiment, the provided methods comprise administration of an effective amount of at least one mammalian α-defensin and at least one mammalian β-defensin to a subject in need of such treatment. A preferred embodiment provides administration of the mammalian alpha defensin HD5 and/or the mammalian beta defensin hBD-2.

In other embodiments, the provided methods comprise administration of an effective amount of at least one mammalian cathelicidin to a subject in need of such treatment. In some embodiments, the methods comprise administration of an effective amount of human LL37 to a subject in need of such treatment.

In other embodiments, the provided methods comprise administration of an effective amount of at least one GLP-1 analog to a subject in need of such treatment. In a particular embodiment the GLP-1 analog is liraglutide.

In further embodiments, the provided methods comprise administration of an effective amount of at least one mammalian α-defensin and at least one mammalian cathelicidin to a subject in need of such treatment. A preferred embodiment provides administration of the mammalian alpha defensin HD5 and/or the mammalian cathelicidin. In a further embodiment, the provided methods comprise administration of an effective amount of at least one mammalian β-defensin and at least one mammalian cathelicidin to a subject in need of such treatment. A preferred embodiment provides administration of the mammalian beta defensin hBD-2 and/or the mammalian cathelicidin. In some embodiments, the methods further comprise administration of a GLP-1 analog such as liraglutide.

A "functionally equivalent variant" of a mammalian (e.g. human) alpha or beta defensin or cathelicidin is a modified mammalian (e.g. human) alpha or beta defensin or cathelicidin exhibiting approximately the same effect on inflammation of the liver, biliary tract or pancreas as the parent mammalian (e.g. human) alpha and/or beta defensins and/or cathelicidin. A functionally equivalent variant of a mammalian (e.g. human) defensin or cathelicidin may comprise 1-5 amino acid modifications, preferably 1-4 amino acid modifications, more preferably 1-3 amino acid modifications, most preferably 1-2 amino acid modification(s), and in particular one amino acid modification, as compared to the mammalian (e.g. human) defensin or cathelicidin amino acid sequence. Preferably, for beta mammalian defensins, compared to human beta defensin 2, having SEQ ID NO: 5. Preferably, for alpha mammalian defensins, compared to HD5, having SEQ ID NO: 8. Preferably, for mammalian cathelicidin, compared to human LL37, having SEQ ID NO: 16.

The present methods may also comprise administration of functional equivalents of GLP-1 analogs or modified forms thereof, such as functional equivalents of liraglutide.

The term "modification" means herein any chemical modification of a mammalian (e.g. human) defensin, a mammalian cathelicidin or a GLP-1 analog such as liraglutide. The modification(s) can be substitution(s), deletion(s) and/or insertions(s) of the amino acid(s) as well as replacement(s) of amino acid side chain(s); or use of unnatural amino acids with similar characteristics in the amino acid sequence. In particular the modification(s) can be amidations, such as amidation of the C-terminus.

Preferably, amino acid modifications are of a minor nature, that is conservative amino acid substitutions or insertions that do not significantly affect the folding and/or activity of the polypeptide; single deletions; small amino- or carboxyl-terminal extensions; or a small extension that facilitates purification by changing net charge or another function, such as a poly-histidine tag, an antigenic epitope or a binding domain. In one embodiment the small extension, such as a poly-histidine tag, an antigenic epitope or a binding domain is attached to the mammalian (e.g. human) alpha or beta defensin through a small linker peptide of up to about 20-25 residues and said linker may contain a restriction enzyme cleavage site. The Clustal W alignments in FIGS. 3 to 6 can be used to predict which amino acid residues can be substituted without substantially affecting the biological activity of the protein. The sequences were aligned using Clustal W 2.1 (www.genome.jp/tools/clustalw/) and the following settings: Gap Open Penalty: 10, Gap Extension Penalty: 0.05, Weight Transition: NO, Hydrophilic Residues for Proteins: GPSNDQE, Hydrophilic Gaps: YES, Weight Matrix: BLOSUM (for PROTEIN).

Substitutions within the following group (Clustal W, 'strong' conservation group) are to be regarded as conservative substitutions:

S,T,A; N,E,Q,K; N,H,Q,K; N,D,E,Q; Q,H,R,K; M,I,L,V; M,I,L,F; H,Y; F,Y,W.

Substitutions within the following group (Clustal W, 'weak' conservation group) are to be regarded as semi-conservative substitutions:

C,S,A; A,T,V; S,A,G; S,T,N,K; S,T,P,A; S,G,N,D; S,N,D,E,Q,K; N,D,E,Q,H,K; N,E,Q,H,R,K; V,L,I,M; H,F,Y.

Examples of conservative substitutions are substitutions made within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by Neurath and Hill (1979). The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Essential amino acids in a mammalian alpha and/or beta defensin and/or cathelicidin and/or in a GLP-1 analog or its peptide backbone can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., activity against an inflammatory bowel disease and/or suppression of TNF-alpha activity) to identify amino acid residues that are critical to the activity of the molecule. See also, Hilton et al., 1996, *J. Biol. Chem.* 271: 4699-4708. The identities of essential amino acids can also be inferred from analysis of identities with polypeptides which are related to mammalian alpha and/or beta defensins and/or cathelicidin and/or the peptide backbone of GLP-1 analogs (see Clustal W alignments in FIGS. 3 to 6).

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30:10832-10837; U.S. Pat. No. 5,223,409; WO 92/06204), and region-directed mutagenesis (Derbyshire et al., 1986, *Gene* 46:145; Ner et al., 1988, *DNA* 7:127).

When the result of a given substitution cannot be predicted with certainty, the derivatives may be readily assayed according to the methods described herein above to determine the presence or absence of biological activity.

Long-Acting Compounds

The half-life of an α- or β-defensin or cathelicidin may be extended by fusing or conjugating the α- or β-defensin or cathelicidin with another molecule i.e. constructing a long acting biologically active α- or β-defensin or cathelicidin linked to a pharmaceutically acceptable molecule providing an in vivo plasma half-life of the α- or β-defensin or cathelicidin, which is increased substantially compared to the in vivo plasma half-life of the α- or β-defensin or cathelicidin administered in the same manner as the α- or β-defensin or cathelicidin.

A long acting biologically active α- or β-defensin or cathelicidin comprising a mammal α-defensin or analog thereof or a mammal β-defensin or analog thereof or a human cathelicidin or analog thereof linked to a pharmaceutically acceptable molecule selected from a molecule having binding to a mammal neonatal Fc receptor, transferrin or a CH3(CH2)nCO—, wherein n is 8 to 22 or a polymer.

The α- or β-defensin or cathelicidin agonist may also be of non-mammalian origin, and may be selected from small organic molecules, peptides, polypeptides and proteins. The α- or β-defensin or cathelicidin agonist may be linked to the pharmaceutically acceptable molecule in various ways as described in the prior art literature, such as without limitation chemical coupling through a bifunctional linker, gene technologically by coupling the N-terminal or C-terminal end of the defensin, such as α-defensin or β-defensin or cathelicidin, to the pharmaceutically acceptable molecule, such as albumin or albumin analog. In particular, the N-terminal end of albumin or an albumin analog, e.g. human albumin, can be coupled to the C-terminal end of an α-defensin or β-defensin or cathelicidin, or the N-terminal end of an α- or β-defensin or cathelicidin; or the C-terminal end of albumin, e.g. human albumin, can be coupled to the C-terminal end of an α-defensin or β-defensin or cathelicidin, or the N-terminal end of α- or β-defensin or cathelicidin. A linker sequence can be inserted between the albumin and the α- or β-defensin or cathelicidin chain.

The α- or β-defensin or cathelicidin agonist may be linked to the pharmaceutically acceptable molecule through a stable linker or a more labile linker. Several linkers are known in the art, including bifunctional PEG molecules (e.g. see Paige et al. Pharmaceutical Research, vol. 12, no. 12, 1995), hydrolysable linkers (Shechter et al. Bioconjugate Chem. 2005, 16: 913-920 and International Journal of Peptide Research and Therapeutics, Vol. 13, Nos. 1-2, June 2007 and WO2009095479), PDPH and EMCH see e.g. in WO2010092135. In the special case where chemical conjugation (linking of two or more molecules) of the α- or β-defensin or cathelicidin agonist, to the pharmaceutically acceptable molecule, strongly reduce the functional α- or β-defensin or cathelicidin activity, it may be preferable to use a more labile linker that can release the functional α- or β-defensin or cathelicidin agonist.

Half-life extension may also be accomplished through acylation of the peptide backbone with a spacer e.g. γ-L-glutamyl spacer and a C-18 fatty di-acid chain to Lysine. The fatty di-acid site chain and the spacer mediate a strong but reversible binding to albumin, slowing release from the injection site and reducing renal clearance.

Likewise, the half-life of a GLP-1 analog such as liraglutide may be extended by methods known in the art, including the above-mentioned methods.

In some embodiments, the alpha-defensin, the beta-defensin, the cathelicidin or the GLP-1 analog further comprises at least one further moiety selected from a group consisting of a cell penetrating peptide (CPP), an Albumin Binding Moiety (ABM), a detectable moiety (Z), and a half-life extending peptide.

In other embodiments, the alpha-defensin, the beta-defensin, the cathelicidin or the GLP-1 analog does not comprise any of a cell penetrating peptide (CPP), an Albumin Binding Moiety (ABM), a detectable moiety (Z), and a half-life extending peptide.

Methods and Uses

As demonstrated in example 5, administration of Liraglutid, a GLP-1 analog was found to have a weight lowering effect in mice fed a high fat diet. The GLP-1 analog also decreased fat accumulation in the liver and plasma cholesterol levels. Therefore, the inventors contemplate treatment of a liver, biliary tract, pancreatic or metabolic disease or disorder, or of liver cancer, cholangiocarcinoma or pancreatic cancer and other uses as described herein by administration of GLP-1 or a GLP-1 analog.

Preferably, GLP-1 or GLP-1 analogs are administered parenterally through either subcutaneous or intramuscular administration. The GLP-1 analog may be selected from exenatide, liraglutide, lixisenatide, albiglutide, and dulaglutide.

Human alpha defensin 5 and human beta defensin 2 alone or in combination and/or cathelicidin and/or a GLP-1 analog are found to be able to prevent or treat weight gain, lipid accumulation and inflammation in mice being fed a high fat/sugar diet ('Western diet'). Mice fed this high fat/sugar diet rapidly gain weight and accumulate epididymal or visceral fat and/or fat in the liver in the absence of any treatment. Accumulation of fat in the liver amounts to non-alcoholic fatty liver disease, which in later stages can lead to liver steatosis, —fibrosis, —cirrhosis, hepatic encephalopathy and ultimately liver cancer. By reducing the accumulation of abdominal fat e.g. in the liver it is possible to reduce or prevent the occurrence of NAFLD, NASH and related disorders.

If weight gain can be prevented or reduced, the accumulation of epididymal or visceral fat and/or fat in the liver can also be prevented or reduced, thus showing activity as a potential medicament for treatment or prevention of liver disease, including liver cancer and hepatic encephalopathy, biliary tract and pancreas disorders and certain metabolic disorders. Therefore, one aspect provides methods for treatment or prevention of liver, biliary tract and pancreas disorders as well as metabolic disorders as defined herein.

Examples of liver disorders include alcoholic (IDC10: K70) and non-alcoholic liver disease, toxic liver disease (IDC 10: K71) e.g. fatty liver, hepatitis (IDC 10: K73 and K75), cirrhosis (IDC 10: K74), hepatic failure (IDC 10: K72), fibrosis (IDC 10: K74) and sclerosis of the liver and most importantly non-alcoholic steato hepatitis NASH— (IDC 10: K75.8) and non-alcoholic fatty liver disease (NAFLD) (IDC 10: K76.0). In a particular embodiment the liver disease is NASH or NAFLD.

Non-alcoholic fatty liver disease (NAFLD) is the most common liver disease in the World with increasing prevalence due to the close association with the epidemic growth of obesity. Steatosis, which is an abnormal retention of lipids in a cell, often occurs in the liver but may occur in other organs such as the kidneys, heart and muscle. Steatosis in the liver can give rise to fatty liver disease (FLD), which can be further categorised as alcoholic or non-alcoholic fatty liver disease (NAFLD), depending on the contribution of alcohol consumption.

Simple steatosis is not linked to increased risk of liver-related morbidity or mortality; however, non-alcoholic steatohepatitis (NASH) may progress to advanced liver fibrosis and cirrhosis, and is also associated with increased liver cancer risk. Subjects suffering from NASH have an increased risk (5-10%) of developing cancer such as hepatocellular carcinoma, comparable to the risk in subjects who develop cirrhosis because of hepatitis C. It is estimated that about 1 million US citizens suffer from NASH, although it is difficult to quantify since NASH does not always cause symptoms. NASH is however diagnosed in 7-9% of people in the US who have a liver biopsy and is the primary indication for a liver transplantation in US citizens under the age of 25.

NASH is often seen in people with BMI (body mass index) greater than 30, with diabetes and/or with insulin resistance. At present, NASH is most often discovered during routine laboratory testing. Additional tests help confirm the presence of NASH and rule out other types of liver disease. Imaging tests (such as ultrasound, CT scan, or magnetic resonance imaging) may reveal fat accumulation in the liver but cannot differentiate NASH from other causes of liver disease that have a similar appearance. A liver biopsy is required to confirm NASH. No specific therapies other than liver transplantation exist for treating NASH at present, but lifestyle management can help reduce its severity.

Elevated levels of liver enzymes such as AST and ALT can be used as part of a diagnostic procedure to identify patients with NAFLD and NASH. ALT levels are usually higher than AST levels in NAFLD patients; however, an AST/ALT ratio greater than 1 is suggestive of an advanced fibrotic form of the disease. This ratio is the simplest predictive model for advanced fibrosis, and it can be calculated using readily available liver function tests. Despite its simplicity, this ratio has a good negative predictive value and can be used to rule out the presence of advanced fibrosis.

Examples of biliary tract and pancreatic disorders include: cholangitis (IDC: K 83.0) and in particular primary sclerosing cholangitis, cholecystitis (IDC10: K81.0), cholangiocarcinoma (IDC10: C22.1) and pancreatitis (IDC10: K85.0).

Examples of metabolic disorders include: disorders of lipoprotein metabolism (IDC10: E78); hypercholesterolaemia (IDC10: E78.0); hyperglyceridaemia (IDC10: E78.1); hyperlipidaemia (IDC10: E78.2 and E78.4); hyperchylomicronaemia (IDC10: E78.3); glycogen storage disease (IDC10: E74); sphingolipid metabolism and lipid storage disorders (IDC10: E75); lipid storage disorders (IDC10: E75.6); gangliosidosis (IDC10: E75) and sphingolipidosis (IDC10: E 75.2).

Common for these disorders is that they are a result of gene mutations or caused or exacerbated by a western lifestyle inducing metabolic syndrome with obesity, dyslipidemia, glucose intolerance and insulin resistance as well as accumulation of abdominal/visceral or liver fat.

The methods disclosed in preferred embodiments can, via administration of at least a mammalian alpha defensin and/or at least a mammalian beta defensin and/or cathelicidin and/or a GLP-1 analog such as liraglutide to treat a liver, biliary tract, pancreatic or metabolic disorder as described above.

The subject in need of the treatment provided by the disclosed methods is affected by a liver, biliary tract, pancreatic or metabolic disorder as described above.

The subject in need of the treatment provided by the disclosed methods may present one or more of the following symptoms:

Elevated blood pressure: 140/90 mmHg;
Dyslipidemia: triglycerides (TG): ≥1.695 mmol/L and high-density lipoprotein cholesterol (HDL-C)≤0.9 mmol/L (male), ≤1.0 mmol/L (female);
Fasting glucose >6.1 mmol/L;
AST/ALT >1;
Central obesity: waist:hip ratio >0.90 (male); >0.85 (female), or body mass index >30 kg/m$^2$; and
Microalbuminuria: urinary albumin excretion ratio 20 µg/min or albumin:creatinine ratio ≥30 mg/g.

In one embodiment, the administration of at least one mammalian α-defensin and/or at least one mammalian β-defensin, according to the disclosed methods, is generally oral.

Mammalian alpha and beta defensins and/or cathelicidins and/or GLP-1 analogs can be employed therapeutically in compositions formulated for administration by any conventional route. In one embodiment, mammalian alpha and/or beta defensins and/or cathelicidin and/or GLP-1 analogs are administered orally. In other embodiments, the administration is parenteral such as intravenous, intramuscular, subcutaneous, intraperitoneal or pulmonary.

Within some embodiments, compositions, of preferred embodiments may be formulated as a lyophilizate, utilizing appropriate excipients that provide stability as a lyophilizate, and subsequent to rehydration.

Pharmaceutical compositions containing a mammalian alpha defensin and/or a mammalian beta defensin and/or a cathelicidin and/or a GLP-1 analog, such as a human alpha defensin and/or a human beta defensin and/or a human cathelicidin and/or liraglutide, can be manufactured according to conventional methods, e.g., by mixing, granulating, coating, dissolving or lyophilizing processes. In a preferred embodiment, pharmaceutical compositions containing a mammalian alpha defensin and/or a mammalian beta defensin are formulated as a sterile and isotonic solution.

The provided pharmaceutical compositions comprise, in one embodiment, at least one mammalian alpha defensin. Examples of mammalian alpha defensins are HD5 and HD6. In a preferred embodiment, the compositions comprise the mammalian alpha defensin HD5. The pharmaceutical compositions comprise, in another embodiment, at least one mammalian beta defensin. Examples of mammalian beta defensins are hBD1, hBD-2, truncated hBD-2, hBD3 and hBD4. In a preferred embodiment, the compositions comprise the mammalian beta defensin hBD-2. The pharmaceutical compositions comprise, in a further embodiment, at least one mammalian alpha defensin and at least one mammalian beta defensin. Examples of mammalian alpha defensins are HD5 and HD6. An example of mammalian beta defensin is hBD-2. In a preferred embodiment, the compositions comprise the mammalian alpha defensin HD5 and the mammalian beta defensin hBD-2. In other embodiments the compositions or feed compositions comprise one or more non-human defensins selected from defensins having an amino acid sequence selected from SEQ ID NO: 1-3 and 10-15 as well as sequence variants as herein defined. In another embodiment, the pharmaceutical compositions comprise at least one cathelicidin, for example human cathelicidin, for example human LL37 of SEQ ID NO: 16. In another embodiment, the pharmaceutical compositions comprise at least one GLP-1 analog, for example liraglutide.

Pharmaceutical compositions of preferred embodiments comprise a mammalian alpha defensin and/or a mammalian beta defensin, such as a human alpha defensin and a human beta defensin, and/or a cathelicidin such as a human cathelicidin and/or a GLP-1 analog such as liraglutide and a pharmaceutically acceptable carrier and/or diluent.

Pharmaceutically acceptable carriers and/or diluents are familiar to those skilled in the art. For compositions formulated as liquid solutions, acceptable carriers and/or diluents include saline and sterile water, and may optionally include antioxidants, buffers, bacteriostats, and other common additives.

The disclosed compound may be formulated in a wide variety of formulations for oral administration. Solid form preparations may include powders, tablets, drops, capsules, cachets, lozenges, and dispersible granules. Other forms suitable for oral administration may include liquid form preparations including emulsions, syrups, elixirs, aqueous solutions, aqueous suspensions, toothpaste, gel dentrifrice, chewing gum, or solid form preparations which are intended to be converted shortly before use to liquid form preparations, such as solutions, suspensions, and emulsions.

The formulation can contain (in addition to a mammalian alpha defensin and/or a mammalian beta defensin and/or cathelicidin, and other optional active ingredients) carriers, fillers, disintegrators, flow conditioners, sugars and sweeteners, fragrances, preservatives, stabilizers, wetting agents, emulsifiers, solubilizers, salts for regulating osmotic pressure, buffers, diluents, dispersing and surface-active agents, binders, lubricants, and/or other pharmaceutical excipients as are known in the art.

One skilled in this art may further formulate mammalian alpha defensin and mammalian beta defensins and/or cathelicidin in an appropriate manner, and in accordance with accepted practices, such as those described in Remington's Pharmaceutical Sciences, Gennaro (1990).

A mammalian alpha defensin and a mammalian beta defensin, such as a human alpha defensin and a human beta defensin, can be used alone, or in combination therapies with one, two, or more other pharmaceutical compounds or drug substances, for example with insulin or insulin analogs, glucagon like peptide-1 (GLP-1) or GLP-1 analogs, or dipeptidyl peptidase-IV (DDP-IV) inhibitors, and/or with one or more pharmaceutically acceptable excipient(s).

A mammalian alpha defensin and/or a mammalian beta defensin and/or a cathelicidin, such as a human alpha defensin, a human beta defensin and/or human cathelicidin, can be used alone, or in combination therapies with one, two, or more other pharmaceutical compounds or drug substances, for example with antibiotics; insulin or insulin analogs; glucagon like peptide-1 (GLP-1) or GLP-1 analogs; glucagon like peptide-2 (GLP2) or GLP-2 analogs; dipeptidyl peptidase-IV (DDP-IV) inhibitors; metformin; sodium glucose transporter-2 (SGLT-2) inhibitors; glucagon receptor antagonists and/or a transient receptor potential cation channel subfamily V member 1 (TRPV1) antagonist and/or with one or more pharmaceutically acceptable excipient(s).

A mammalian alpha defensin and/or a mammalian beta defensin and/or cathelicidin, such as a human alpha defensin, a human beta defensin and human cathelicidin, may also be used in combination therapies with either chemotherapy, immunotherapy, radiotherapy or a combination of these.

Likewise, a GLP-1 analog may be used alone, or in combination therapies with one, two, or more other pharmaceutical compounds or drug substances, for example with antibiotics; insulin or insulin analogs; glucagon like peptide-1 (GLP-1) or a further GLP-1 analog; glucagon like peptide-2 (GLP2) or GLP-2 analogs; dipeptidyl peptidase-IV (DDP-IV) inhibitors; metformin; sodium glucose transporter-2 (SGLT-2) inhibitors; glucagon receptor antagonists and/or a transient receptor potential cation channel subfamily V member 1 (TRPV1) antagonist and/or with one or more pharmaceutically acceptable excipient(s).

A GLP-1 analog such as liraglutide, may also be used in combination therapies with either chemotherapy, immunotherapy, radiotherapy or a combination of these.

In Vitro Synthesis

Mammalian alpha defensins, mammalian beta defensins, cathelicidin and/or GLP-1 analogs may be prepared by in vitro synthesis, using conventional methods as known in the art. Various commercial synthetic apparatuses are available, for example automated synthesizers by Applied Biosystems Inc., Beckman, etc. By using synthesizers, naturally occurring amino acids may be substituted with unnatural amino acids, particularly D-isomers (or D-forms) e.g. D-alanine and D-isoleucine, diastereoisomers, side chains having different lengths or functionalities, and the like. The particular sequence and the manner of preparation will be determined by convenience, economics, purity required, and the like.

Chemical linking may be provided to various peptides or proteins comprising convenient functionalities for bonding, such as amino groups for amide or substituted amine formation, e.g. reductive amination, thiol groups for thioether or disulphide formation, carboxyl groups for amide formation, and the like.

If desired, various groups may be introduced into the peptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Mammalian alpha defensins and mammalian beta defensins, cathelicidin and/or GLP-1 analogs or functional equivalents thereof, may also be isolated and purified in accordance with conventional methods of recombinant synthesis. Recombinant synthesis may be performed using appropriate expression vectors and a eukaryotic expression system. A solution may be prepared of the expression host and the media and the defensins present purified using HPLC, exclusion chromatography, gel electrophoresis, affinity chromatography, or other purification technique. Methods for recombinant expression of human beta defensin 2 in *E. coli* are disclosed in WO 2010/007166 (Novozymes).

Dosages

A mammalian alpha defensin, a mammalian beta defensin, cathelicidin and/or a GLP-1 analog, such as a human alpha defensin, a human beta defensin, cathelicidin and/or a GLP-1 analog such as liraglutide, are preferably employed in pharmaceutical compositions in an amount which is effective to treat liver disease, biliary tract or pancreatic disorders or metabolic disorders preferably with acceptable toxicity to the patient. A mammalian alpha defensin, a mammalian beta defensin, a mammalian cathelicidin and/or a GLP-1 analog such as a human alpha defensin, a human beta defensin, a human cathelicidin and/or a GLP-1 analog, are also preferably employed in pharmaceutical compositions in an amount which is effective to treat inflammation of the liver, biliary tract or pancreas, preferably with acceptable toxicity to the patient or the animal in need of the treatment.

For such treatments, the appropriate dosage will, of course, vary depending upon, for example, the chemical nature and the pharmacokinetic data of a compound used, the individual host, the mode of administration and the nature and severity of the conditions being treated.

In general, in mammals, for example humans, an indicated daily dosage of a human alpha defensin is preferably from about 0.1 mg HD5/kg body weight to about 10 mg HD5/kg body weight, more preferably from about 0.5 mg HD5/kg body weight to about 10 mg HD5/kg body weight; such as 1 mg HD5/kg body weight to 10 mg HD5/kg body weight, more preferably from about 1.2 mg HD5/kg body weight to about 10 mg HD5/kg body weight, preferably from about 1.2 mg HD5/kg body weight to about 5 mg HD5/kg body weight, even more preferably 1.2 mg HD5/kg body weight, for example, administered in divided doses up to one, two or three times a day. Similar dosages can be used for other alpha-defensins. In some embodiments, the alpha-defensin is administered at least twice a day, such as three times a day.

In one embodiment an indicated daily dosage of a human beta defensin is preferably from about 0.1 mg hBD-2/kg body weight to about 10 mg hBD-2/kg body weight, more preferably from about 0.5 mg hBD-2/kg body weight to about 10 mg hBD-2/kg body weight; such as 1 mg hBD-2/kg body weight to 10 mg hBD-2/kg body weight, more preferably from about 1.2 mg hBD-2/kg body weight to about 10 mg hBD-2/kg body weight, preferably from about 1.2 mg hBD-2/kg body weight to about 5 mg hBD-2/kg body weight, even more preferably 1.2 mg hBD-2/kg body weight, for example, administered in divided doses up to one, two or three times a day. Similar dosages can be used for other beta-defensins. In some embodiments, the beta-defensin is administered at least twice a day, such as three times a day. In preferred embodiments, the administration is oral.

In one embodiment an indicated daily dosage of a human cathelicidin is preferably from about 0.1 mg cathelicidin/kg body weight to about 10 mg cathelicidin/kg body weight, for example, administered in divided doses up to one, two or three times a day. In some embodiments, the cathelicidin is administered at least twice a day, such as three times a day. In preferred embodiments, the administration is oral.

In one embodiment an indicated daily dosage of a GLP-1 analog such as liraglutide is preferably from about 0.6 mg GLP-1 analog to about 3 mg GLP-1 analog daily. For example, a dosage regimen for liraglutide can be 0.6 mg a day for one week, followed by 1.2 mg a day for one week, followed by 1.8 mg a day for one week, followed by 2.4 mg a day for one week, followed by 3 mg a day for one week or more, such as two weeks, such as three weeks, such as four weeks, or more. In a preferred embodiment, the GLP-1 analog is administered intravenously, intramuscularly or subcutaneously.

An indicated daily dosage of a human alpha defensin together with a human beta defensin or human cathelicidin is preferably from about 0.1 mg defensin or cathelicidin/kg body weight to about 10 mg defensin/kg body weight, more preferably from about 0.5 mg defensin or cathelicidin/kg body weight to about 10 mg defensin/kg body weight; such as 1 mg defensin or cathelicidin/kg body weight to 10 mg defensin or cathelicidin/kg body weight, more preferably from about 1.2 mg defensin or cathelicidin/kg body weight to about 10 mg defensin/kg body weight, preferably from about 1.2 mg defensin or cathelicidin/kg body weight to about 5 mg defensin/kg body weight, even more preferably 1.2 mg defensin or cathelicidin/kg body weight, for example, administered in divided doses up to one, two or three times a day. When two different defensins are administered in one dosage, the dosage may comprise equal or approximately equal amounts of the two defensins determined on a weight basis or on a molar basis. The ratio may also differ so that the ratio of alpha defensin to beta-defensin varies from 10:1 to 1:10, such as 5:1 to 1:5, for example 2:1 to 1:2 determined on a weight or molar basis.

The daily dosage could correspond to 0.6 mg HD5/kg body weight plus 0.6 mg hBD-2/kg body weight.

In certain embodiments, the pharmaceutical compositions of preferred embodiments can include a mammalian alpha defensin and/or a mammalian beta defensin and/or a mammalian cathelicidin, such as a human alpha defensin and/or a human beta defensin and/or a human cathelicidin, in an amount of about 0.1 mg or less to about 1500 mg or more per unit dosage form, such as 0.5 mg or less to about 1500 mg or more per unit dosage form, preferably from about 0.1, 0.2, 0.3, 0.4, 0.5, 0.6, 0.7, 0.8, or 0.9 mg to about 150, 200, 250, 300, 350, 400, 450, 500, 600, 700, 800, 900, or 1000 mg, and more preferably from about 1, 2, 3, 4, 5, 6, 7, 8, 9, 10, 15, 20, or 25 mg to about 30, 35, 40, 45, 50, 55, 60, 65, 70, 75, 80, 85, 90, 95, or 100 mg. In certain embodiments, however, lower or higher dosages than those mentioned above may be preferred. Appropriate concentrations and dosages can be readily determined by one skilled in the art. In certain embodiments, the pharmaceutical compositions of preferred embodiments include a mammalian alpha defensin, such as a human alpha defensin.

In other embodiments, the pharmaceutical compositions of preferred embodiments include a mammalian beta defensin, such as a human beta defensin. In further embodiments, the pharmaceutical compositions of preferred embodiments include a mammalian alpha defensin and a mammalian beta defensin, such as a human alpha defensin and a human beta defensin, wherein the alpha and the beta defensins are present in equal amounts on a molarity basis or on a mg/mL basis.

In one embodiment, the mammalian alpha and/or beta defensin and/or cathelicidin is administered at least once daily, such as at least twice daily, for example at least 3 times daily. In one embodiment, the GLP-1 analog is administered at least once daily, such as at least twice daily, for example at least 3 times daily. In one embodiment, the GLP-1 analog is administered subcutaneously, intravenously or intramuscularly.

In another embodiment, the mammalian alpha and/or beta defensin and/or cathelicidin is administered as a food or drink supplement.

The disclosure is further described by the following examples that should not be construed as limiting the scope of the invention.

EXAMPLES

Example 1. Prevention of Weight Gain and Improvement of the Muscle/Fat Ratio as Well as Prevention of Fat Accumulation in the Liver by Defensins Materials and Methods Mice:
Mice were housed in trios, 4 cages per group. Feed intake was registered daily just before lights were turned off (6 pm). Individual mice were subjected to experimental procedures in altered order both group and cage wise. Mice were kept at room temperature under a 12-hour light/dark cycle at SPF standard conditions.
Diets:
For dosing, the average weight was estimated to be 25 grams per mouse. They eat approximately 3 grams of feed per mouse per day.
Treatment Regime:
Mice were fed either a high fat diet (HFD) or a low fat (LF) control diet. The HFD contains 4 subgroups; 1 hBD-2, 1 HD5, 1 hBD-2/HD5 and 1 standard HFD without supplementation of defensins. Defensin concentration is 1.2 mg hBD-2 per kg mouse per day. HD5 is given in equimolar concentration to hBD-2. The combinatory group is given 50% hBD-2+50% HD5, hence a total amount of defensins equivalent to the remaining test groups.
Tests:
Insulin tolerance test (ITT), glucose-stimulated insulin secretion (GSIS) test, oral glucose tolerance test (OGTT) and five hours fasting insulin test were performed over two days, with 50% of the mice per group per day, hence avoiding day to day variation as a confounding factor.

Microbial analyses are carried out to study the microbiota of the intestine. Longitudinal 16S characterization is conducted on 4 paired samples from 60 mice, 240 samples in total. Each mouse is sampled prior to diet change, 1 week post diet change, 4 weeks post diet change and at termination, thus ensuring a thorough characterization of the faecal microbiota as a result of defensin treatment. Additionally, the content of the small intestine is analysed at termination (via 16S or deep sequencing), hence providing valuable insight to possible alterations at the key site of nutrient uptake. Lastly, a full metabolomic profile of the cecal content is conducted to allow translation of microbial alterations into whole-body metabolism. A detailed histological and immunohistochemical analysis of the liver, duodenum, jejunum, ileum and colon is also performed.

Example 2. Prevention of Weight Gain and Improvement of the Muscle/Fat Ratio as Well as Prevention of Fat Accumulation in the Liver by Defensins Materials and Methods Mice:
Mice were housed in trios, 4 cages per group. Feed intake was registered daily just before lights were turned off (6 pm). Individual mice were subjected to experimental procedures in altered order both group and cage wise. Mice were kept at room temperature under a 12-hour light/dark cycle at SPF standard conditions.
Diets:
For dosing, the average weight was estimated to be 25 grams per mouse. Mice eat approximately 3 grams of feed per mouse per day.
Treatment Regime:
Mice were fed either a high fat diet (HFD) or a low fat (LF) control diet. The HFD contained 3 subgroups; 1 hBD-2, 1 HD5 and 1 standard HFD without supplementation of defensins. Defensin concentration was 1.2 mg hBD-2 per kg mouse per day. HD5 was given in equimolar concentration to hBD-2. Tests: Insulin tolerance test (ITT), glucose-stimulated insulin secretion (GSIS) test, oral glucose tolerance test (OGTT) and five hours fasting insulin test were performed over two days, with 50% of the mice per group per day, hence avoiding day to day variation as a confounding factor.
Results (Examples 1 and 2)
In the HFD groups, at termination, mice treated with alpha, beta and alpha and beta defensins show less weight gain, a higher muscle/fat ratio as well as less fat accumulation in the liver than mice that were not treated.
Weight Change.
While the food intake was similar in all three experimental diet groups, both High Fat Diet (HFD) groups gained significantly more weight than the Low Fat Diet (LFD) reference group over the 10 week study period (*$p<0.0001$, 2-way ANOVA, Tukey Post Test). The HFD plus hBD-2 group, however, gained significantly less weight than the HFD reference group (*$p=0.0028$) (FIGS. 7 and 10A).
Lean/Fat Mass Development.
The lean/fat mass was equally distributed between the three experimental groups at study outset. At the end of the study both HFD groups had gained the same amount of lean mass, which was significantly higher than the LFD group (*$p<0.0001$, One-way ANOVA, Tukey Post Test), probably due to increased body mass. At the end of the study, the HFD plus hBD-2 group trended towards increased fat mass compared to the LFD group. However this was not statistically significant (*$p=0.25$). The HFD group had gained almost four times the amount of fat mass compared with the LFD group and 2 times the amount of fat mass compared to the HFD plus hBD-2 group (*$p<0.0001$ and *$p=0.005$, respectively) (FIG. 8A).

Insulin Tolerance Test.

Figure 9A:
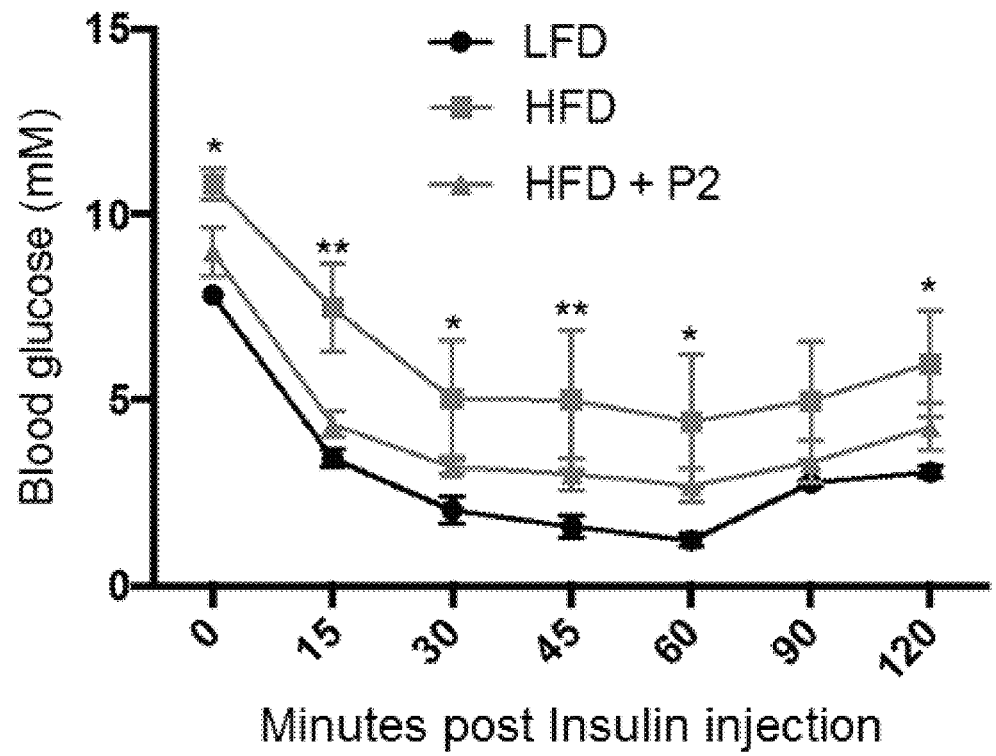
Figure 13A:
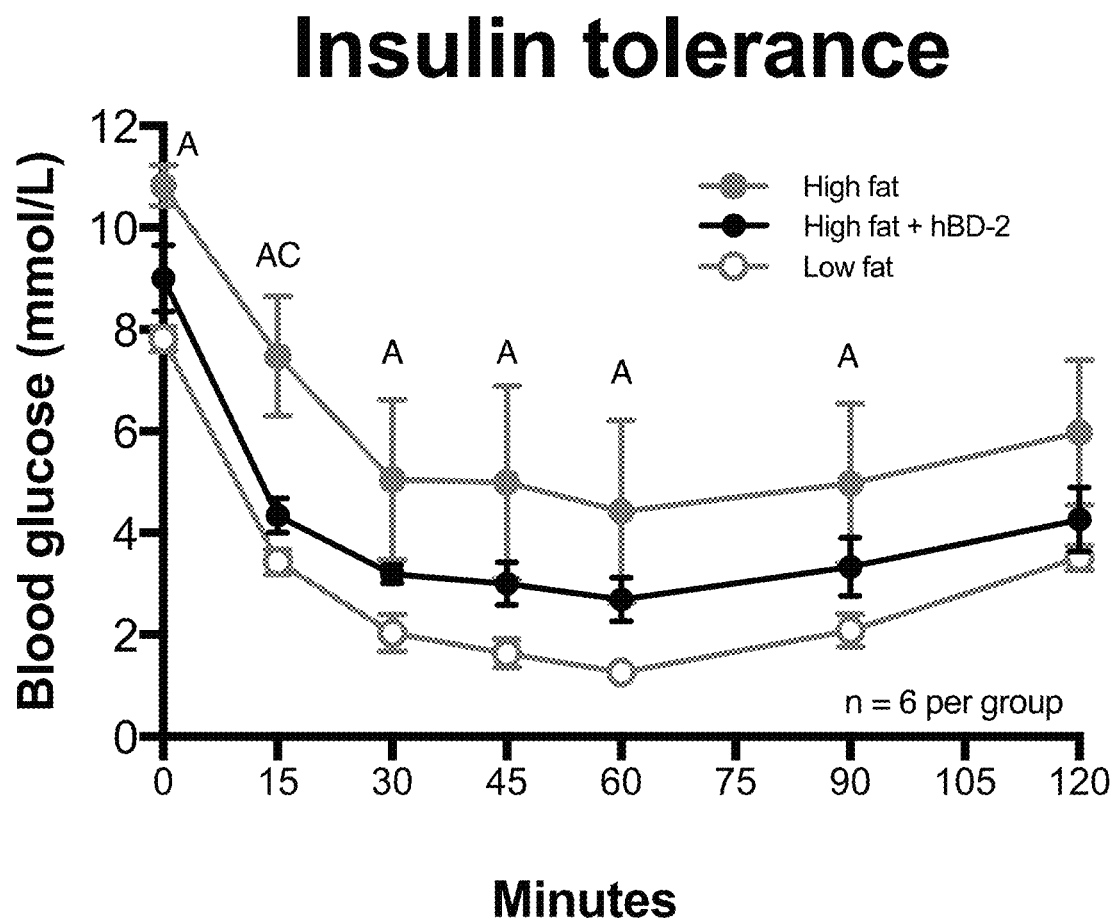

Both the LFD group and the HFD plus hBD-2 group were significantly more sensitive to insulin than the HFD group (p<0.05) (FIGS. 9A and 13A).

Glucose Tolerance Test.

Figure 9B:
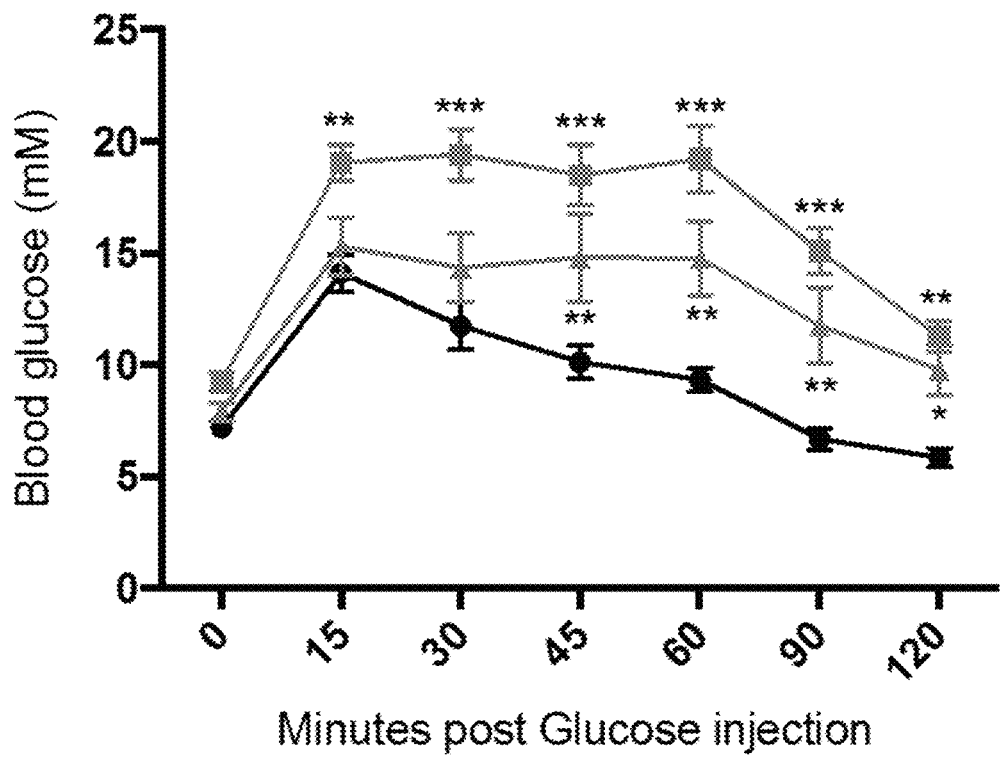
Figure 9C:
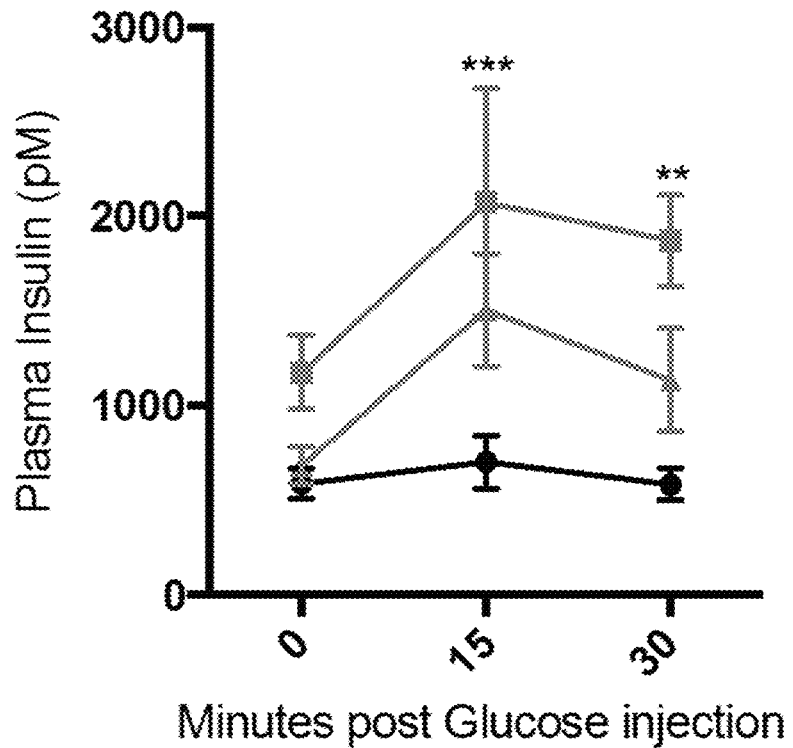
Figure 12A:
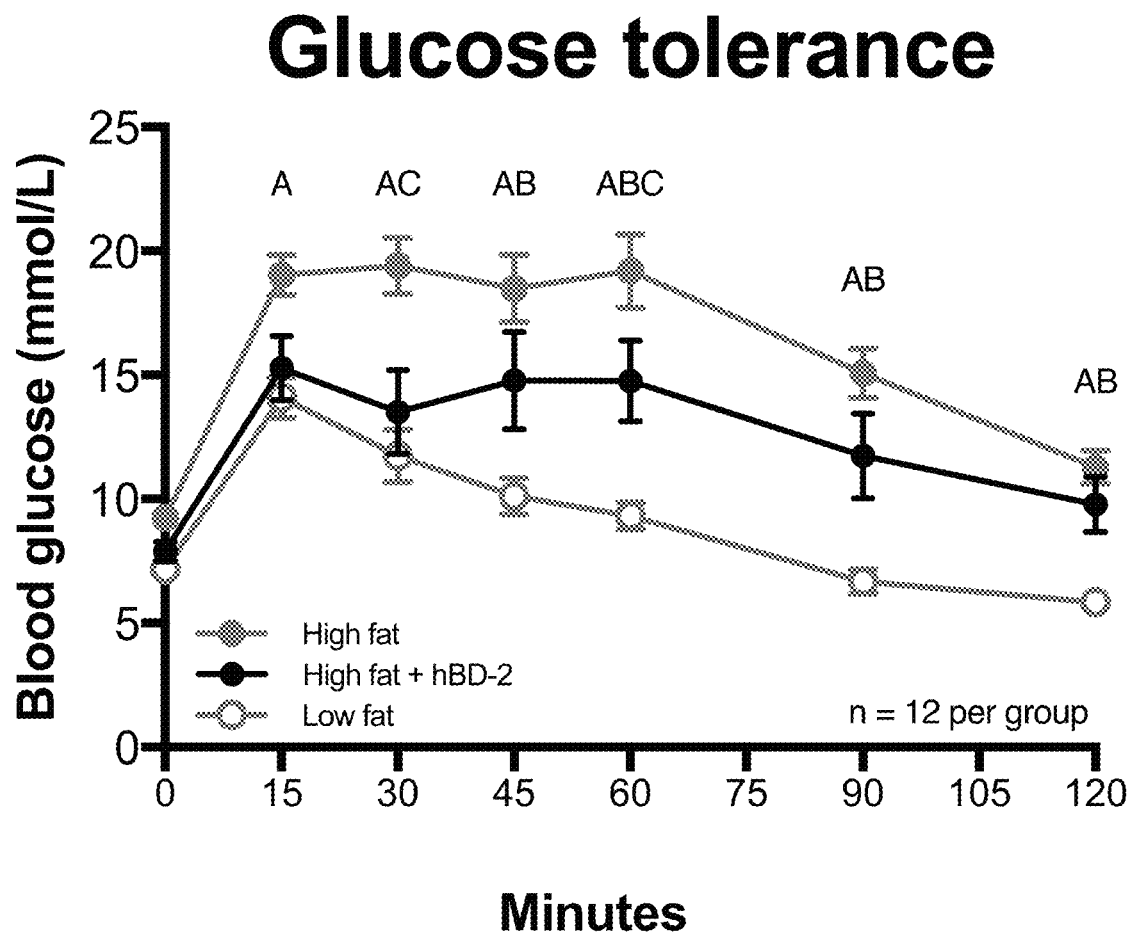

The HFD group was glucose intolerant with a prolonged clearance of glucose from peak at 15 min to semi-clearance at 120 min. The LFD group had a rapid clearance of glucose from peak at 15 min. The HFD plus hBD-2 group had a slightly prolonged glucose clearance but reached significantly lower glucose levels than the HFD group (p<0.05) (FIGS. 9B and 12A).

Glucose Stimulated Insulin Secretion.

Figure 12B:
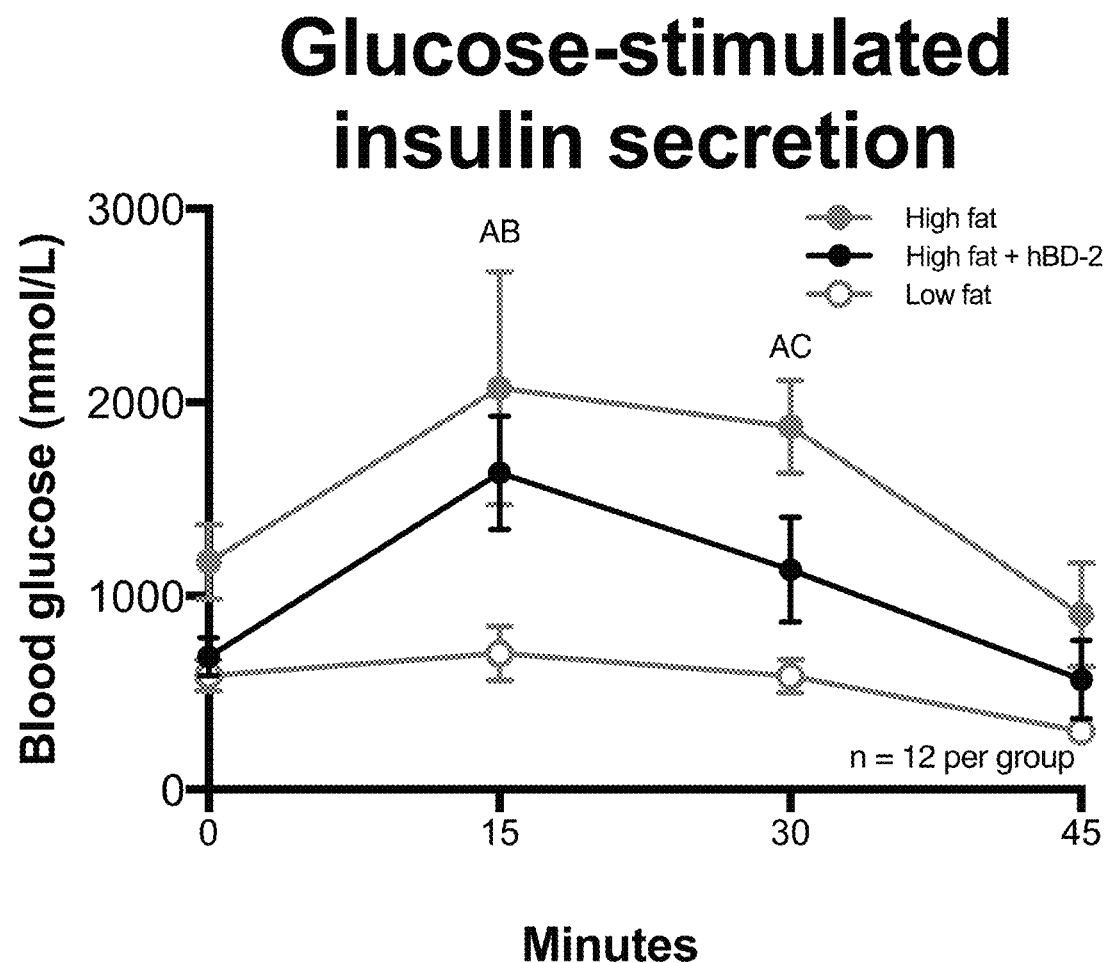

The HFD group had impaired glucose homeostasis with a significantly higher and sustained insulin concentration following glucose administration (p<0.05). The LFD group had almost no increase in insulin concentration following glucose stimulation. The HFD plus hBD-2 group had a higher but not significantly different insulin concentration than the LFD group (FIGS. 12B and 9B).

Five Hour Fasting Insulin.

Figure 9D:
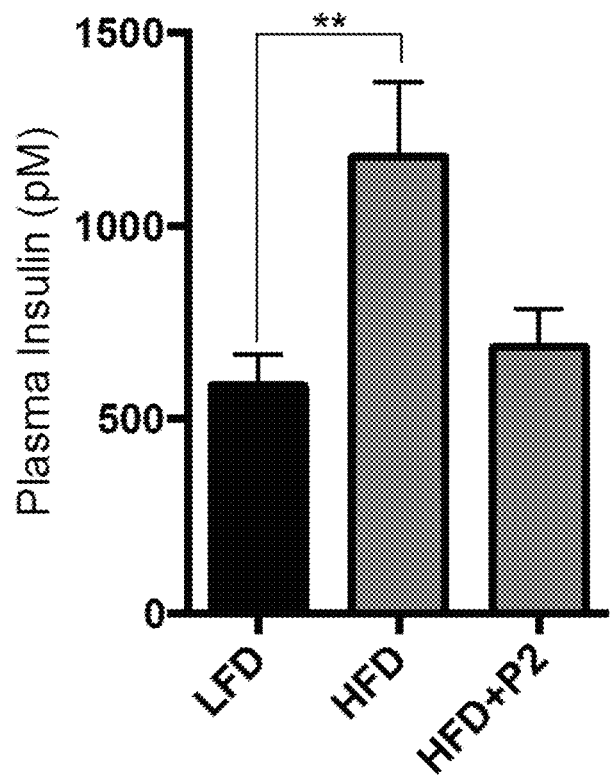

The HFD group were profoundly diabetic with a significantly higher fasting insulin level than the LFD (*p=0.0004) and a borderline significantly higher fasting insulin than the HFD plus hBD-2 group (*p=0.057). There was no significant difference between the LFD and HFD plus hBD-2 groups (*p=0.17) (FIG. 9D).

*Tukey post test, otherwise Dunnett post hoc test.

Figure 13B:
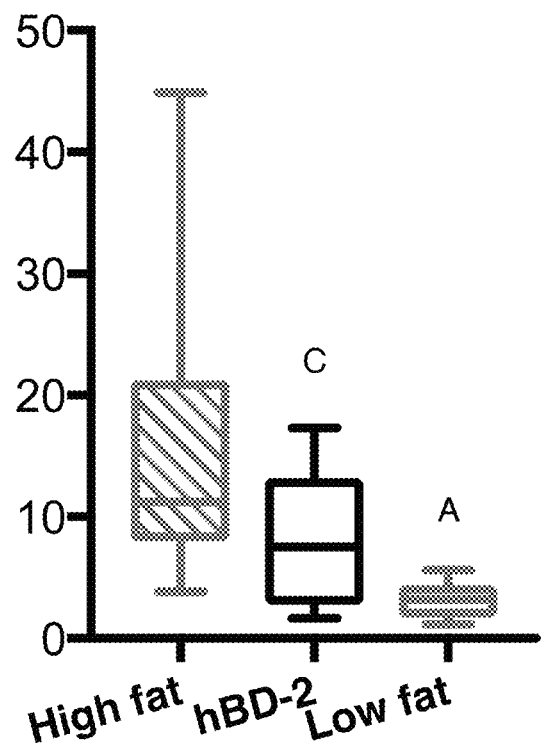

Homeostatic Model Assessment (HOMA-IR) for the assessment of β-cell function and insulin resistance. The HOMA-IR for the HFD plus hBD-2 group was significantly lower than the HFD group indicating a preserved β-cell function and limited insulin resistance (FIG. 13B).

Liver metabolism. Peroxisome proliferator activated receptor gamma 2 (PPARγ2) expression in the liver induces hepatic steatosis, and was found to be upregulated in the HFD fed control group (*p<0.001). The HFD plus hBD-2 resulted in significantly lower expression of PPARγ2 (*p=0.03), which is expected to correlate with reduced fat accumulation, thereby potentially protecting against hepatic steatosis (FIG. 14A). There was no significant difference in liver mass between the HFD plus hBD-2 group and the HFD group; both groups had significantly increased liver mass compared to LFD mice (FIG. 11B). However, eWAT in the HFD plus hBD-2 group was significantly lower than in the HFD group (FIG. 11O).

Conclusions of hBD-2 as Prevention Against Development of Weight Gain, Obesity and Fat Accumulation in the Liver in High Fat Diet Fed Mice:

50% of the HFD-hBD-2-fed mice had a Body Fat Percent resembling LFD reference mice, despite being fed 60% HFD. A few mice had an even lower fat % than the lowest LFD reference mice.

Surprisingly the best protected hBD-2-fed mice had the same or smaller visceral fat mass than LFD reference mice, which is highly unusual on a 60% HFD.

Improved insulin sensitivity. hBD-2 fed mice were not significantly different from the LFD reference mice. Both insulin tolerance test and HOMA-IR indicated improved insulin signaling.

Glucose tolerance was markedly improved compared to HFD control mice. Importantly, both glucose tolerance and the glucose stimulated insulin response during the glucose challenge was improved. The hBD-2-fed mice thus required less insulin to handle the glucose bolus better than did the HFD control mice.

Epididymal fat was reduced in the HFD plus hBD-2 mice compared to the HFD control mice. The HFD plus hBD-2 resulted in significantly lower expression of PPARγ2, indicating reduced fat accumulation.

HD-5 for Prevention of Weight Gain, and Improvement of the Muscle/Fat Ratio as Well as Prevention of Fat Accumulation in the Liver:

Weight Change.

All HFD fed groups had the same food intake during the study period and equal weight gain during the run-in period of 13 weeks (FIG. 20A).

Glucose Tolerance Test.

Figure 22A:
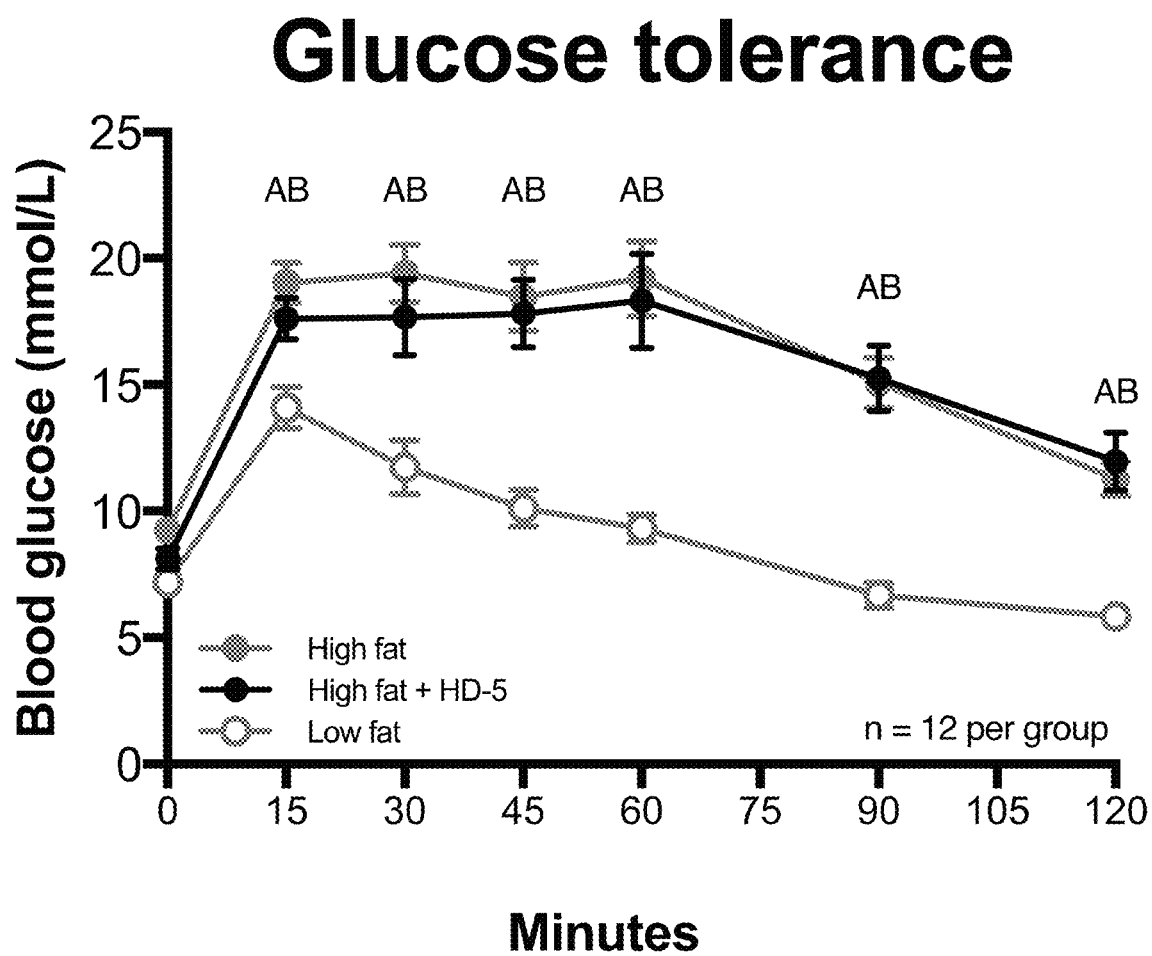

The glucose tolerance for the HFD+HD5 treated animals and for the HFD mice was higher than for the LFD mice (FIG. 22A).

Insulin Tolerance Test.

Figure 23A:
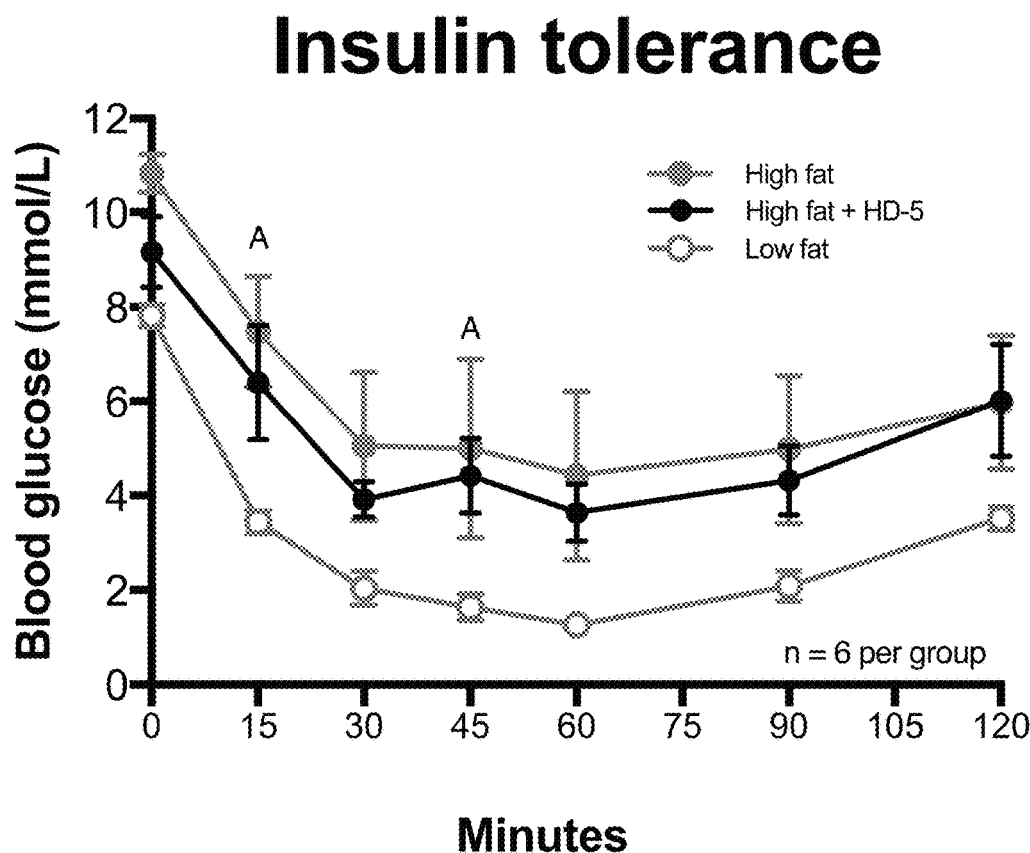

The LFD group was significantly more insulin sensitive than the HFD fed groups (FIG. 23A).

Glucose Stimulated Insulin Secretion.

Figure 22B:
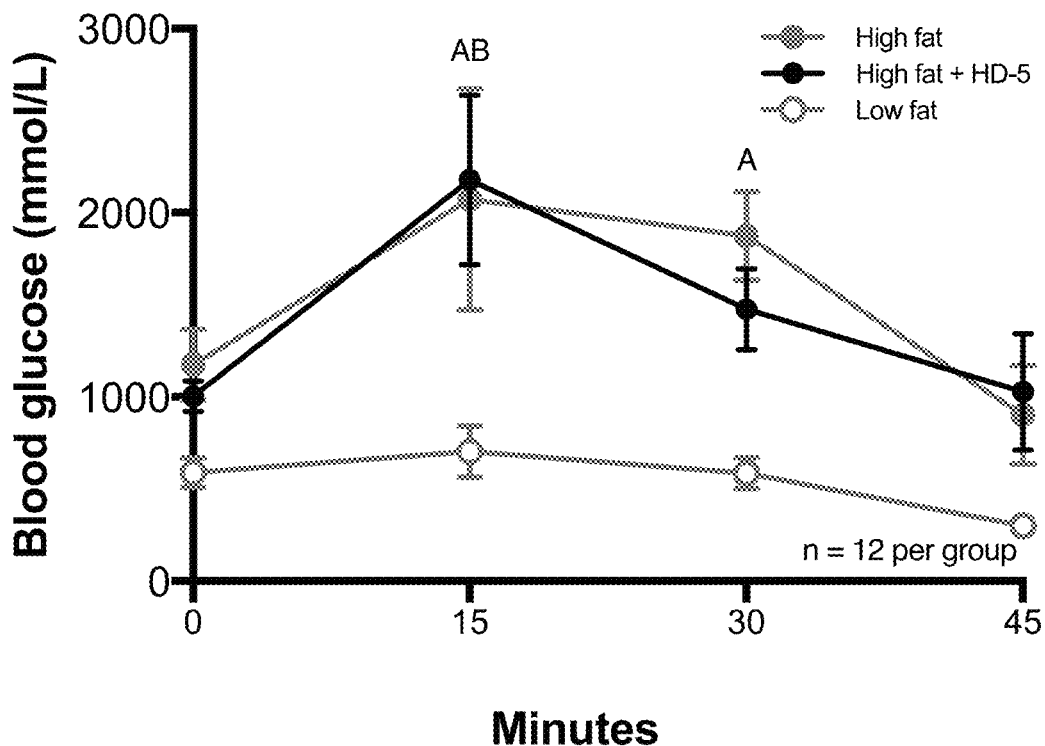

The HFD groups had impaired glucose homeostasis with a significantly higher and sustained insulin concentration following glucose administration (p<0.05). The LFD group had almost no increase in insulin concentration following glucose stimulation (FIG. 22B).

Figure 23B:
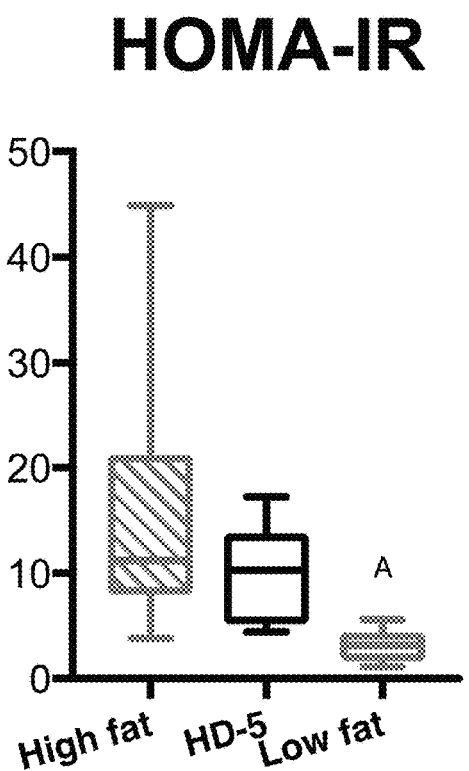

Homeostatic Model Assessment (HOMA-IR) for the assessment of β-cell function and insulin resistance. The HOMA-IR for the HFD plus HD-5 group was not significantly lower than the HFD group (FIG. 23B).

Figure 24A:
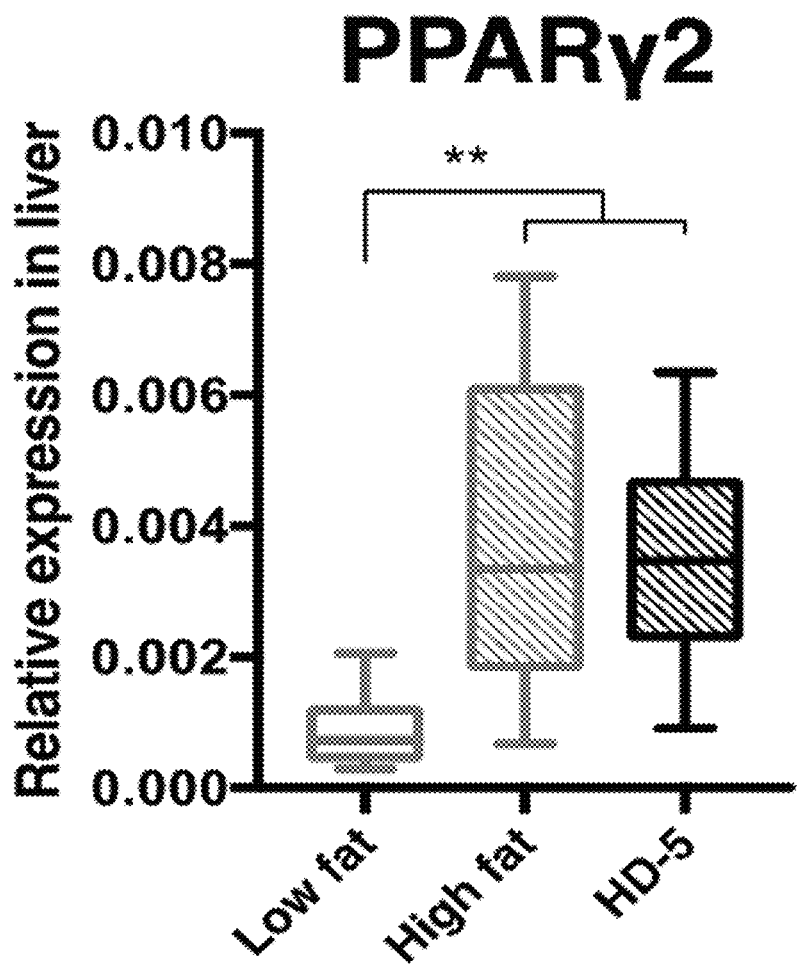
Figure 24B:
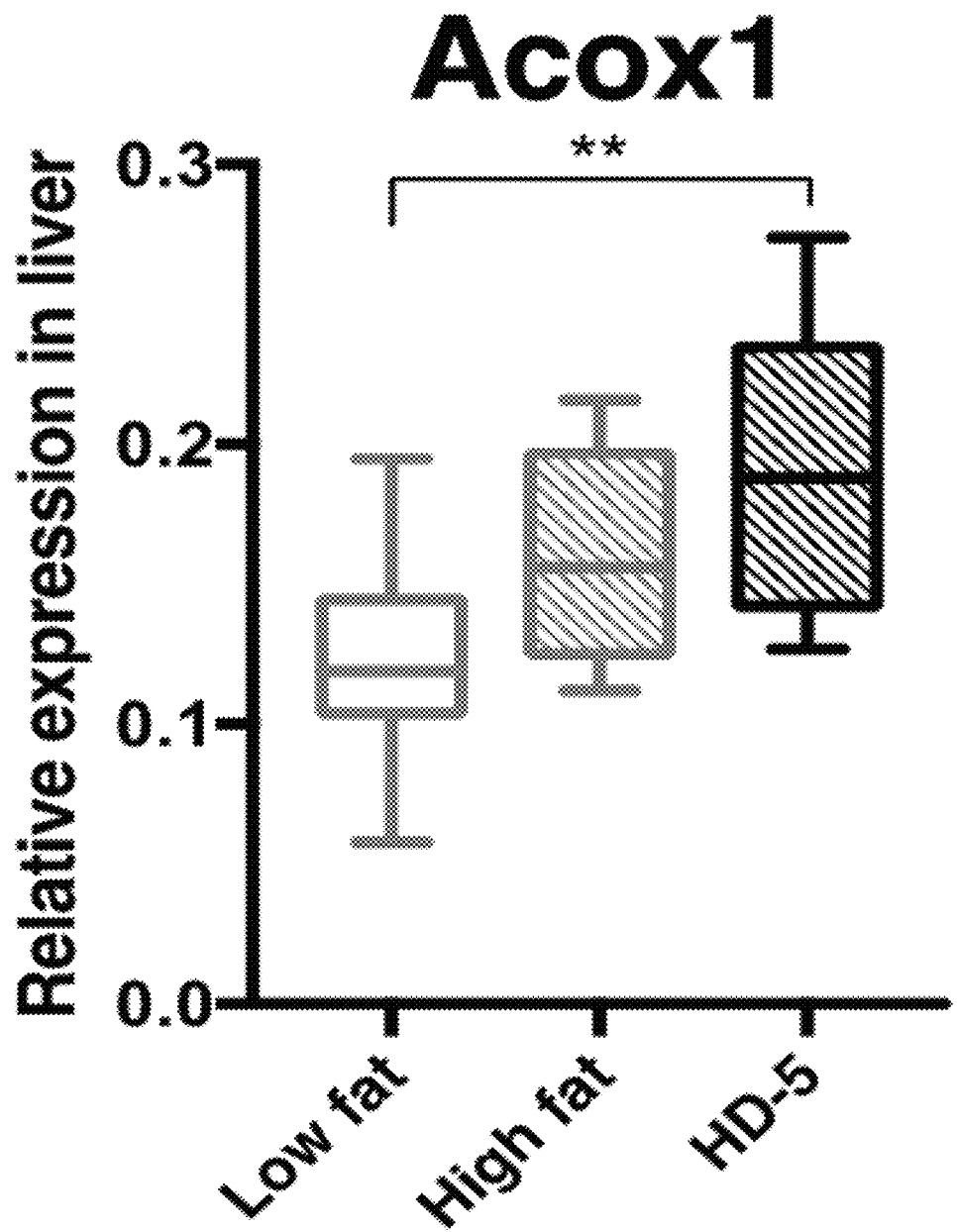

Liver metabolism. Peroxisome proliferator activated receptor gamma 2 (PPARγ2) expression in the liver is increased in HFD fed groups compared to the LFD control (*p<0.001) with no protective effect of HD-5 on HFD (FIG. 24A). Expression of peroxisomal acyl-coenzyme A oxidase 1 (Acox1) in the liver is significantly increased in the HFD plus HD-5 group compared to the LFD control group (*p=0.0009) and a borderline significant difference between HFD control and the HFD plus HD-5 group is observed (*p=0.07, one-way Anova) indicating a higher level of fatty acid oxidation by HD-5 (FIG. 24B).

Conclusions of HD5 as Prevention Against Development of Weight Gain, Obesity and Fat Accumulation in the Liver in High Fat Diet Fed Mice:

HD5-fed mice had borderline less visceral fat than did HFD-fed control mice. There was no improvement in glucose tolerance, suggesting discrepancies in mode of action between hBD-2 and HD5.

Liver metabolism. Whereas hBD-2 significantly lowered the expression of PPARγ2 thus protecting against hepatic steatosis HD5 significantly increased the expression of Acox1 and thus fatty acid metabolism. These changes in liver enzyme expression are different and potentially synergistic as both are potentially preventive against fat accumulation in the liver.

Example 3. Treatment of Fat Accumulation in the Liver Steatohepatitis by Defensins Materials and Methods Mice:

Mice are housed in trios, 4 cages per group. Feed intake is registered 3 times per week. Individual mice are subjected to experimental procedures in altered order both group and cage wise. Mice are kept at room temperature under SPF standard conditions.

Diets:

For dosing, the average weight is estimated to be 25 grams per mouse. They eat approximately 3 grams of feed per mouse per day.

Treatment Regime:

Mice are fed a high fat diet (HFD) for twelve weeks. The mice double their weight over these twelve weeks to approximately 50 gram. The mice are divided into four subgroups; 1 hBD-2, 1 HD5, 1 hBD-2/HD5 and 1 standard HFD without supplementation of defensins. Defensin concentration is 1.2 mg hBD-2 per kg mouse per day. HD5 is given in equimolar concentration to hBD-2. The combinatory group is given 50% hBD-2+50% HD5, hence a total amount of defensins equivalent to the remaining test groups.

Tests:

Insulin tolerance test (ITT), glucose-stimulated insulin secretion (GSIS) test and oral glucose tolerance test (OGTT) is performed over two days, with 50% of the mice per group per day, hence avoiding day to day variation as a confounding factor. Microbial analyses are carried out to study the microbiota of the intestine. Longitudinal 16S characterization is conducted on 4 paired samples from 60 mice, 240 samples in total. Each mouse is sampled prior to defensin treatment, 1 week defensin treatment initiation, 4 weeks post defensin treatment initiation and at termination, thus ensuring a thorough characterization of the faecal microbiota as a result of defensin treatment. Additionally, the content of the small intestine is analysed at termination (via 16S or deep sequencing), hence providing valuable insight to possible alterations at the key site of nutrient uptake. Lastly, a full metabolomic profile of the cecal content is conducted to allow translation of microbial alterations into whole-body metabolism. A detailed histological and immune histochemical analysis of the liver, duodenum, jejunum, ileum and colon is also performed.

Results

In the defensin treated groups, at termination, mice treated with alpha, beta, and alpha and beta defensins show normalization of fat accumulation in the liver, weight loss, improved muscle/fat ratio and normalized metabolic parameters such as Insulin tolerance test (ITT), glucose-stimulated insulin secretion (GSIS) test and oral glucose tolerance test (OGTT) compared with the untreated HFD mice.

Example 4. Treatment of Weight Gain, Obesity and Fat Accumulation in the Liver Steatohepatitis by Defensins Materials and Methods Mice:

Mice were housed in trios, 4 cages per group. Feed intake was registered 3 times per week. Individual mice were subjected to experimental procedures in altered order both group and cage wise. Mice were kept at room temperature under SPF standard conditions.

Diets:

For dosing, the average weight was estimated to be 25 grams per mouse. Mice eat approximately 3 grams of feed per mouse per day.

Treatment Regime:

Mice were fed a high fat diet (HFD) for twelve weeks. The mice doubled their weight over these twelve weeks to approximately 50 gram. The mice were divided into three subgroups; 1 hBD-2, 1 HD5 and 1 standard HFD without supplementation of defensins. Defensin concentration was 1.2 mg hBD-2 per kg mouse per day. HD5 was given in equimolar concentration to hBD-2.

Tests:

Insulin tolerance test (ITT), glucose-stimulated insulin secretion (GSIS) test and oral glucose tolerance test (OGTT) was performed over two days, with 50% of the mice per group per day, hence avoiding day to day variation as a confounding factor.

Results

Weight Change.

Figure 15A:
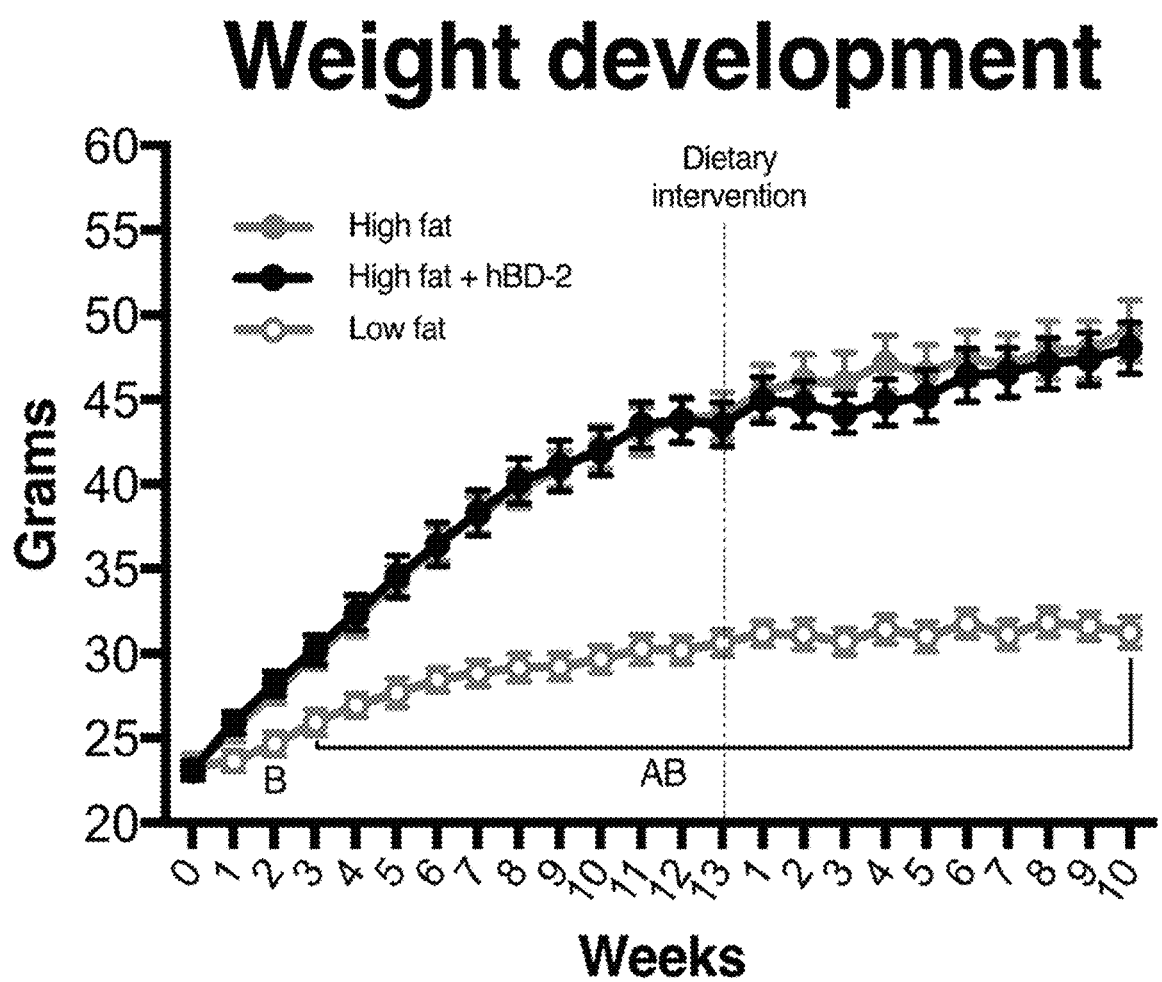
Figure 15B:
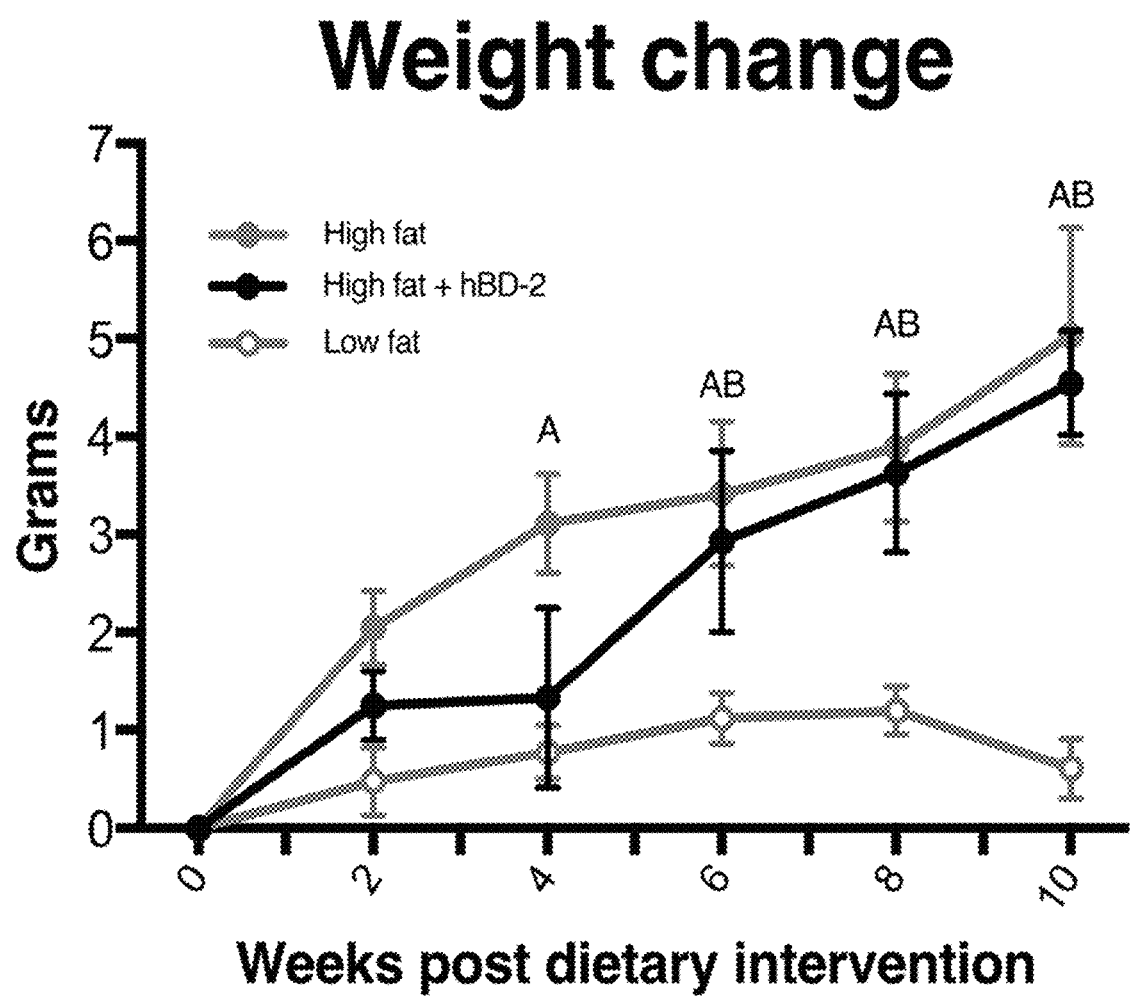

The standard high fat diet (HFD) fed groups had an equal food intake throughout the entire study period and had the same weight development with equal fat and lean mass the first 13 weeks, thus having the same starting point prior to the dietary intervention. The weight gain was significantly larger than in the low fat diet fed (LFD) group (*p<0.05 2-way ANOVA) (FIG. 15A). After the dietary intervention the HFD groups continued to increase in weight, however the HFD plus hBD-2 group tended to gain less weight the first 4 weeks post dietary intervention, although not significantly (*p=0.07 2-way ANOVA). From week 4 to the end of the study period the HFD plus hBD-2 group gained similar weight as the standard HFD group (*p=0.82 2-way ANOVA) (FIG. 15B).

Fat Percentage.

Figure 17A:
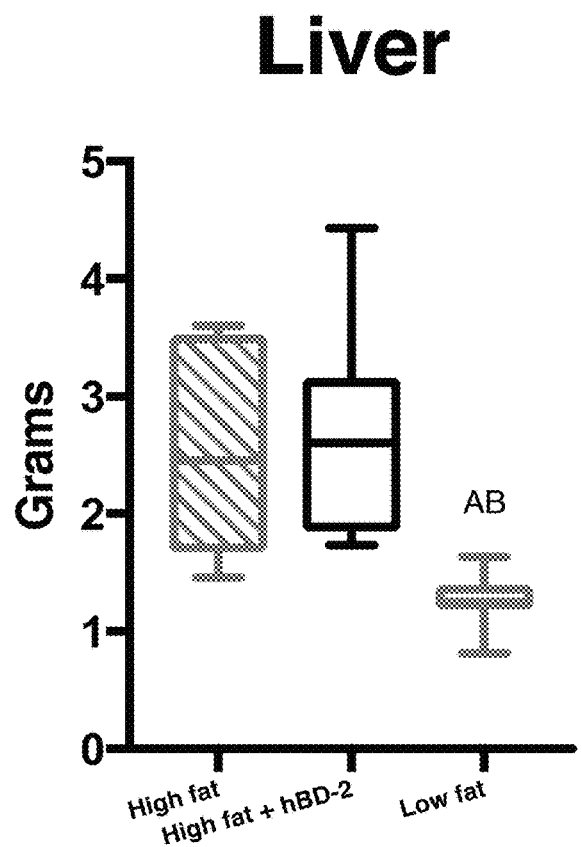
Figure 17B:
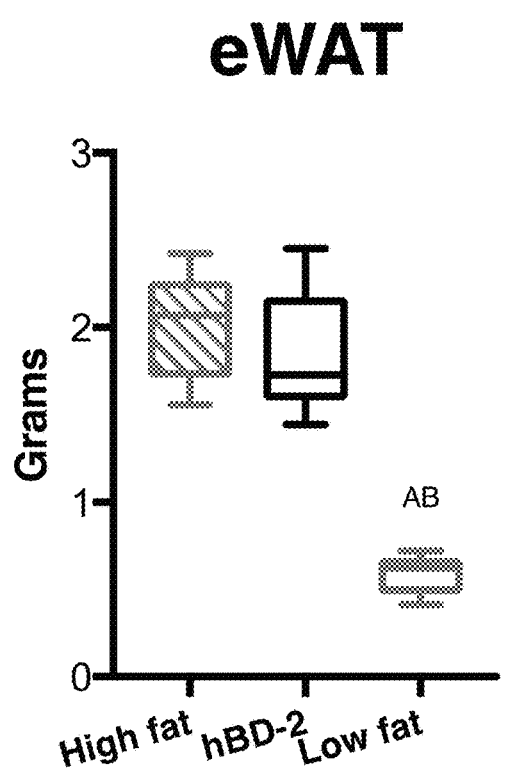

The fat percentage of total body weight was similar between the three experimental groups at onset of the study period. At the point of dietary intervention the fat percentage of the two HFD fed groups was the same and both were significantly larger than the LFD fed group, which was consistent throughout the 10 weeks post dietary intervention (*p<0.05 2-way ANOVA) (FIG. 16A). At weeks 4 post dietary intervention ~75% of the HFD plus hBD-2 group had a smaller fat percentage than before the intervention, dramatically contrasting the standard HFD group, where all mice had increased fat percentages. (FIG. 16B) The change in fat percentage was significantly smaller in the HFD plus hBD-2 group than the standard HFD group at this time point. (*p=0.003 2-way ANOVA). The weight of the liver at termination was significantly larger in the HFD fed groups compared to the LFD group (*p<0.05 One-way ANOVA) (FIG. 17A). The amount of visceral fat (eWAT) at termination was also higher in the HFD groups compared to the LFD (*p<0.05 One-way ANOVA). There was no significant difference in visceral fat (eWAT) between the HFD fed groups (FIG. 17B).

Glucose Tolerance Test.

Figure 18A:
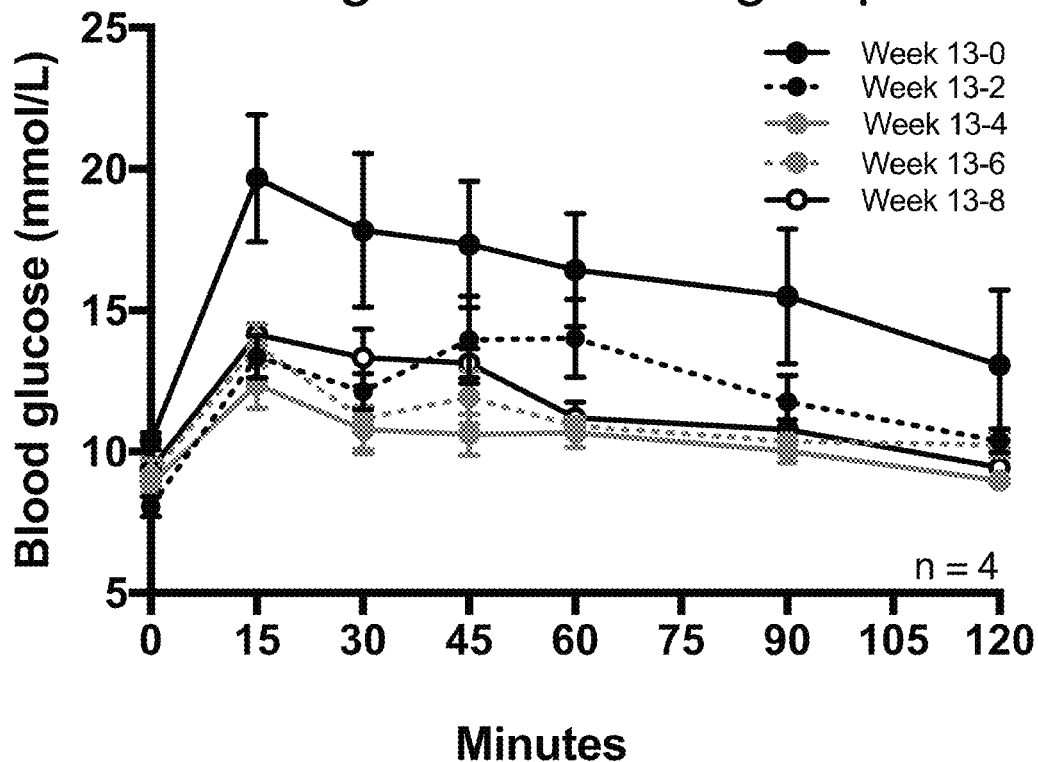
Figure 18B:
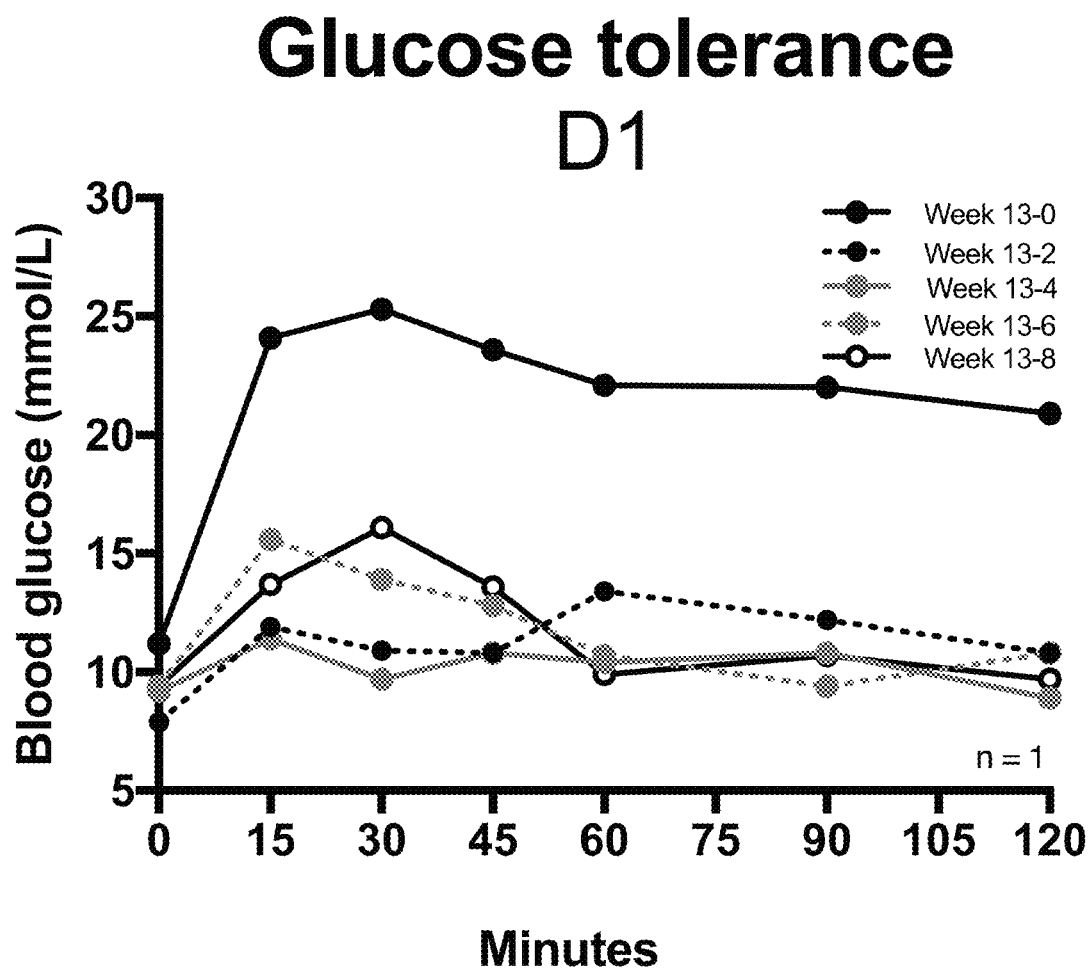

The glucose tolerance improved rapidly from the point of dietary intervention in the HFD plus hBD-2 group, which showed a smaller peak in blood glucose as well as a faster clearance of glucose already after 2 weeks (FIG. 18A). The most glucose intolerant mouse in the study was observed to improve drastically the first two weeks after being switched from a standard HFD to HFD plus hBD-2 (FIG. 18B).

Insulin Tolerance Test.

Figure 18C:
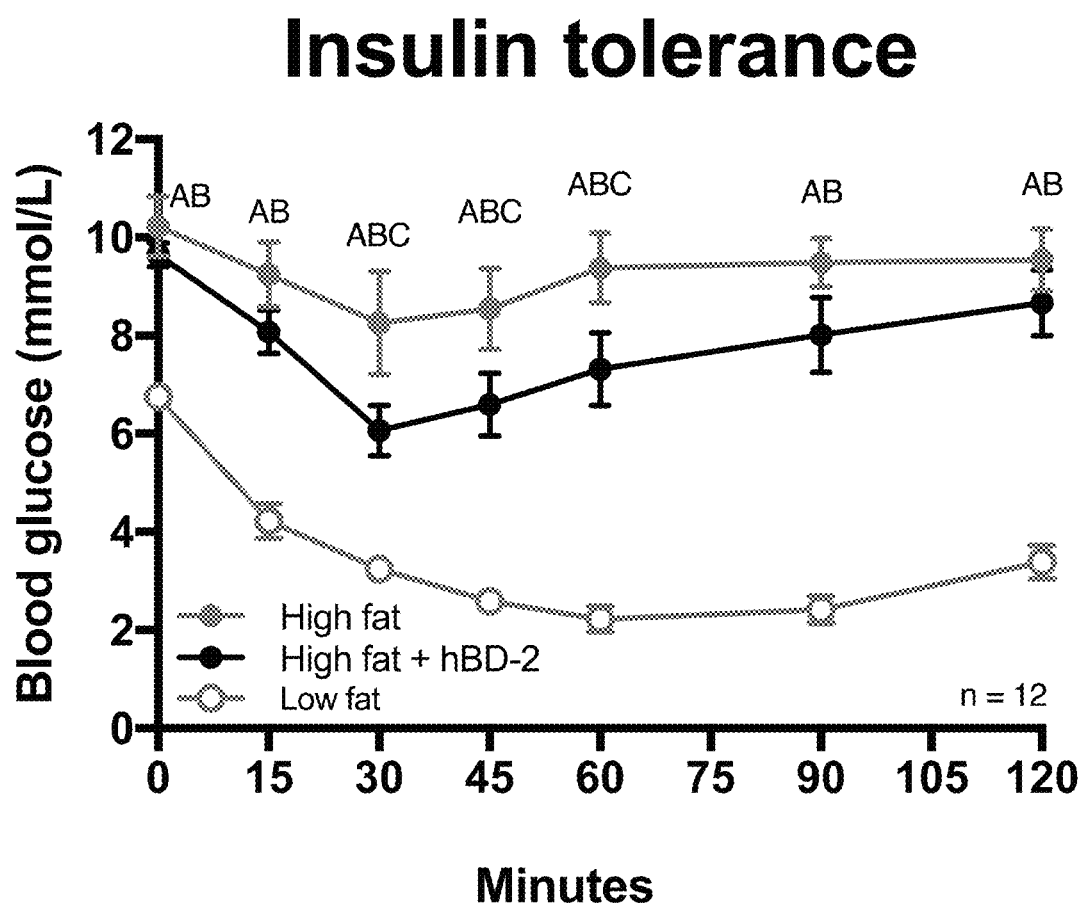

The LFD group was significantly more sensitive to insulin than both HFD groups (*p<0.05 2-way ANOVA). The HFD plus hBD-2 group was simultaneously more insulin sensitive compared to the HFD control group, implying an improvement in insulin tolerance since the dietary intervention (*p<0.05 2-way ANOVA) (FIG. 18C).

Liver Metabolism.

Expression of peroxisomal acyl-coenzyme A oxidase 1 (Acox1) in the liver was significantly increased in the HFD plus hBD-2 group compared to the LFD control group (*p=0.0027) indicating a higher level of fatty acid oxidation by dietary intervention of hBD-2 (FIG. 19). Liver weight and eWAT weight were not significantly different between the control HFD group and the HFD plus hBD-2 group (FIG. 17).

Conclusions of hBD-2 as Treatment of Weight Gain, Obesity and Fat Accumulation in the Liver in High Fat Diet Fed Mice:

Overall, hBD-2-fed mice gained less weight the first 4 weeks of intervention than did HFD control mice (FIG. 15A).

7/8 obese and glucose intolerant mice significantly improved their glucose tolerance following only 2 weeks of intervention (FIG. 18A). A single mouse was the most glucose intolerant mouse at baseline with a fat mass of approximately 20 gram out of 50 grams body weight. Despite this severely unhealthy phenotype, the mouse was completely rescued in terms of glucose intolerance by 2 weeks of intervention (FIG. 18B).

On a whole-body level, hBD-2-fed mice were less insulin resistant than HFD control mice (FIG. 18C). This is a key point as severe systemic insulin resistance is extraordinarily difficult to reverse and a main limitation in treatment of human diseases (e.g. Diabetes, CVDs, certain cancers among others)

hBD-2 fed mice had an increased fatty acid oxidation in the liver (FIG. 19).

HD-5 as Treatment of Weight Gain, Obesity and Fat Accumulation in the Liver in High Fat Diet Fed Mice:

Weight Change.

Figure 25A:
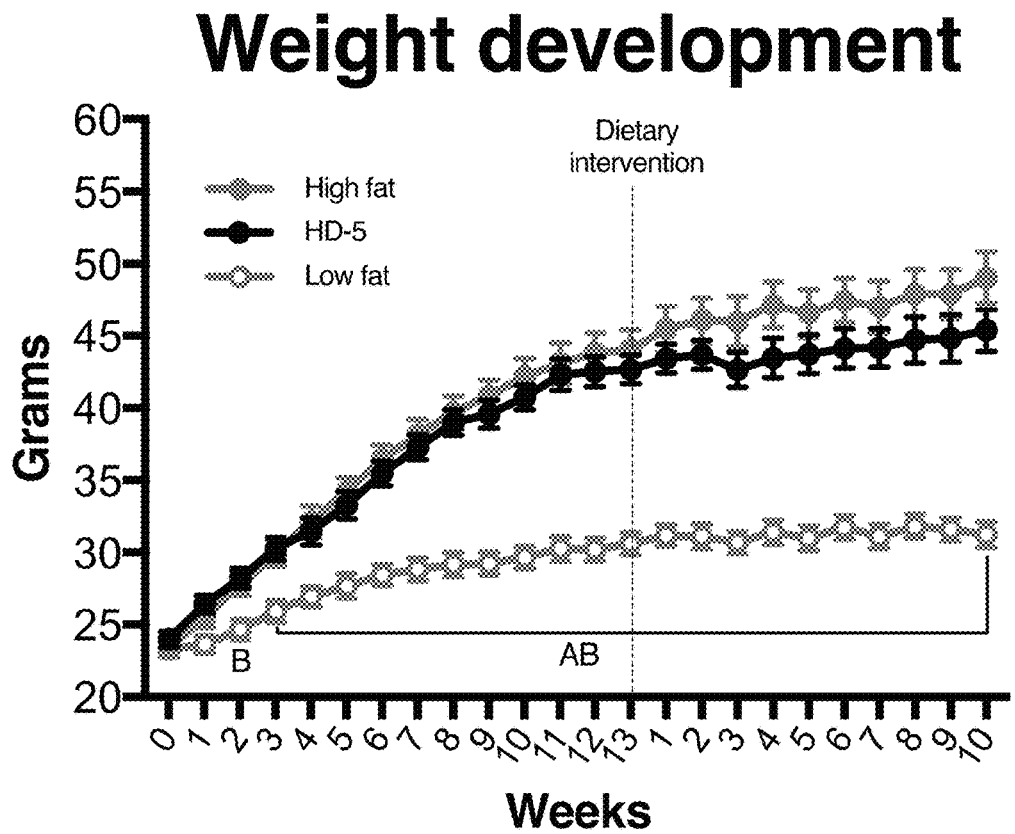
Figure 25B:
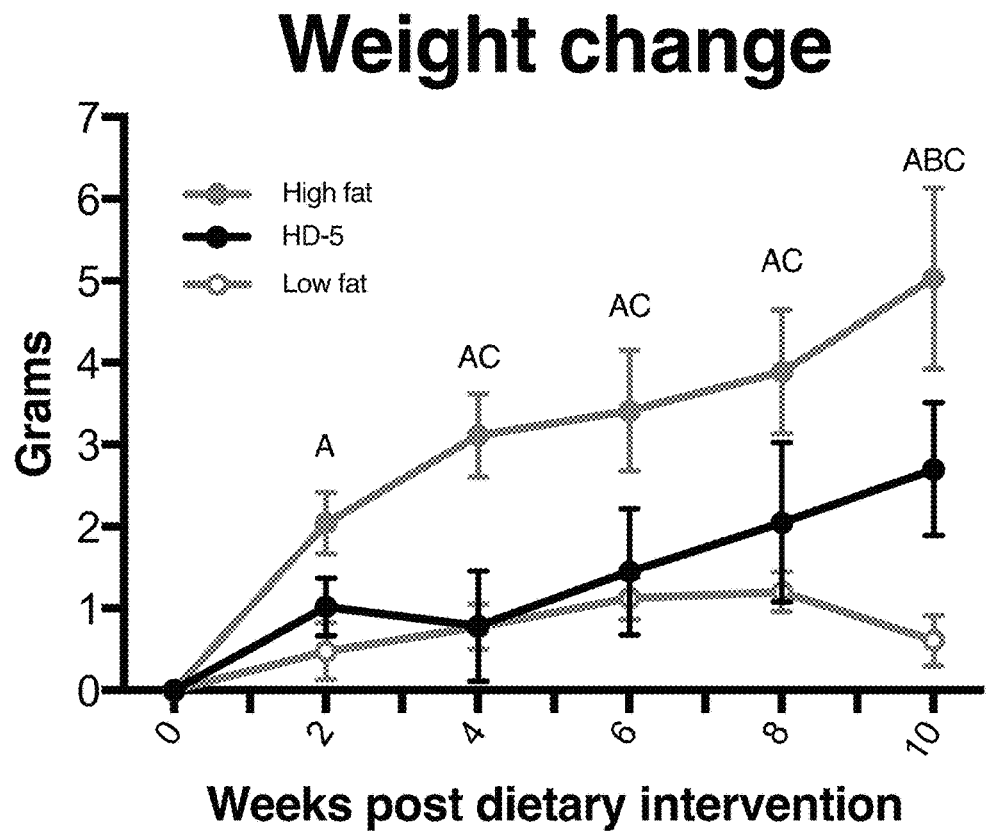

All HFD fed groups had the same food intake during the study period and equal weight gain during the run-in period of 13 weeks (FIG. 25A). After dietary intervention the group fed HFD plus HD-5 gained significantly less weight than the HFD control (*p<0.05 2-way ANOVA) (FIG. 25B). In addition, a tendency of decreasing fat percentage in the HFD plus HD-5 group was observed (FIG. 26A), and a significantly lower fat percentage in the HFD plus HD-5 was measured 4 weeks after dietary change in comparison to the HFD control (*p=0.009 2-way ANOVA) (FIG. 26B). The weight of the liver at termination tended to be decreased in the HFD plus HD-5 fed group compared to the HFD control. Specifically, ~50% of the standard HFD fed mice scored higher than the highest HFD plus HD-5 fed mouse (FIG. 27A). The weight of visceral fat was larger in the HFD fed groups than the LFD fed group. (*p<0.05 One-way ANOVA) (FIG. 27B).

Glucose Tolerance Test.

Figure 28A:
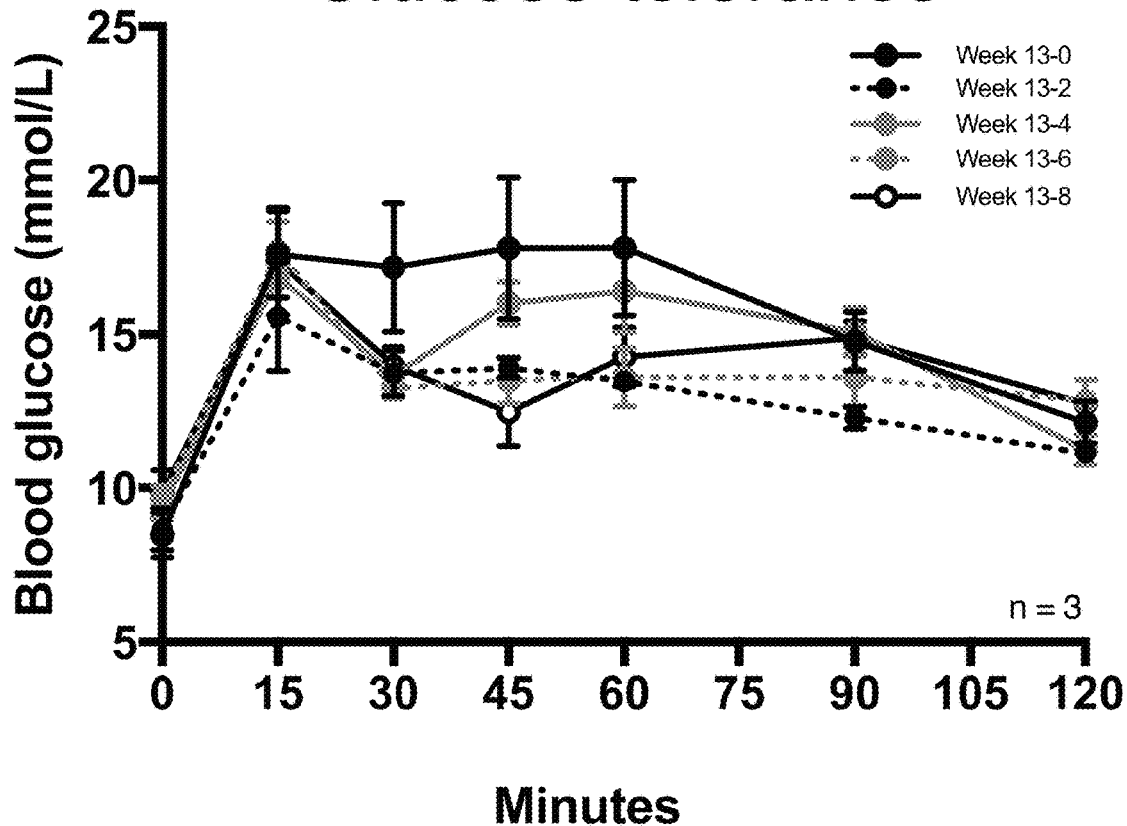

The glucose tolerance for the HFD+HD5 treated animals in a representative cage, Cage 2, improved over time from the start of the intervention (week 13-0) until week 13.8 (FIG. 28A)

Insulin Tolerance Test.

Figure 28B:
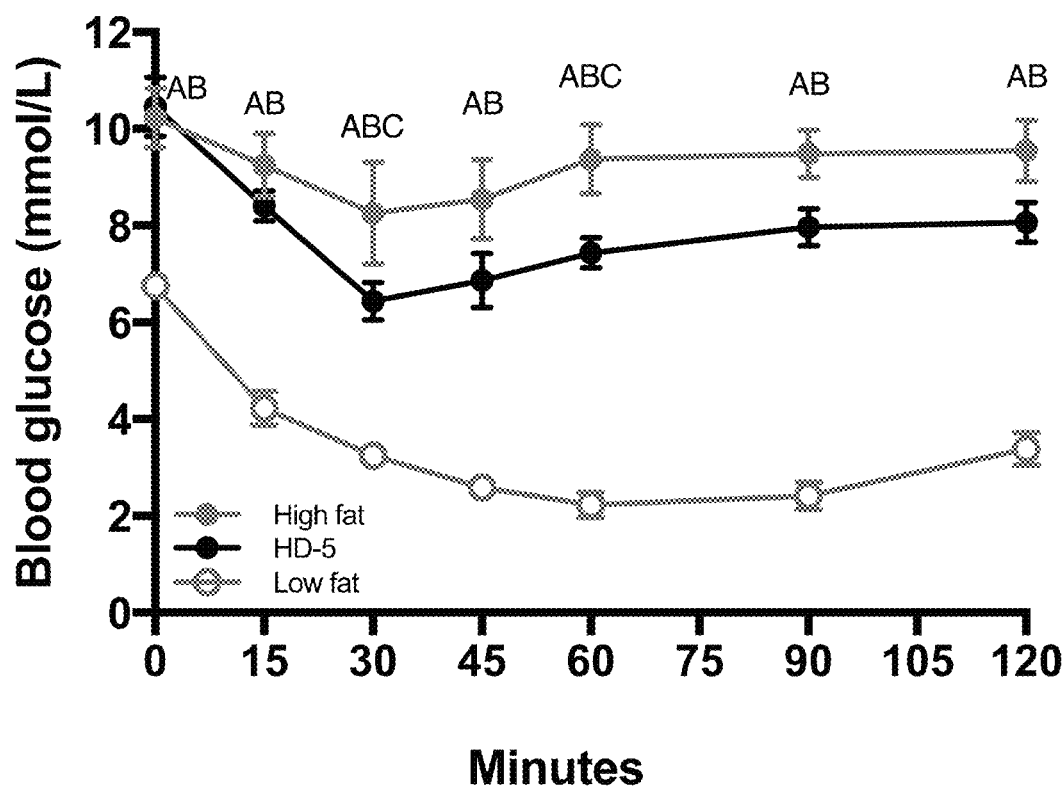

The LFD group was significantly more insulin sensitive than the HFD fed groups (*p<0.05 2-way ANOVA). The HFD plus HD-5 group was more insulin sensitive than the HFD control, implying an improvement in insulin tolerance since the dietary intervention. (*p<0.05 2-way ANOVA) (FIG. 28B).

Liver Metabolism.

Figure 29A:
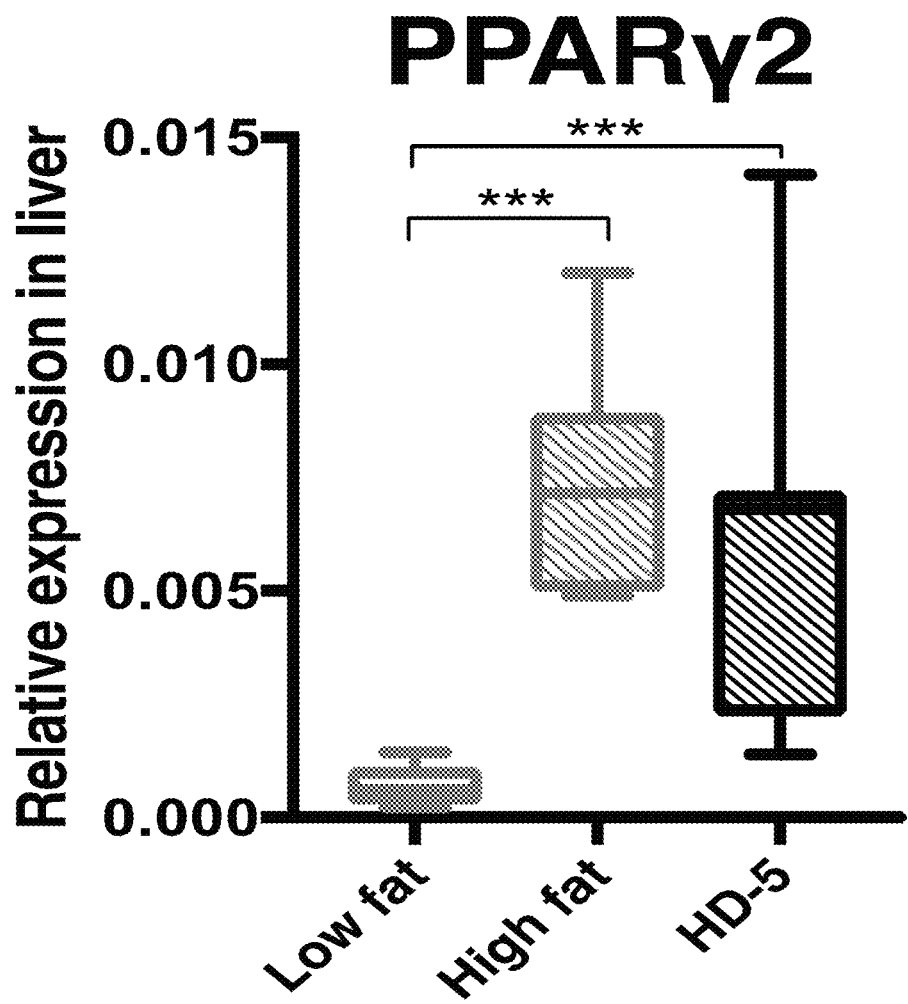
Figure 29B:
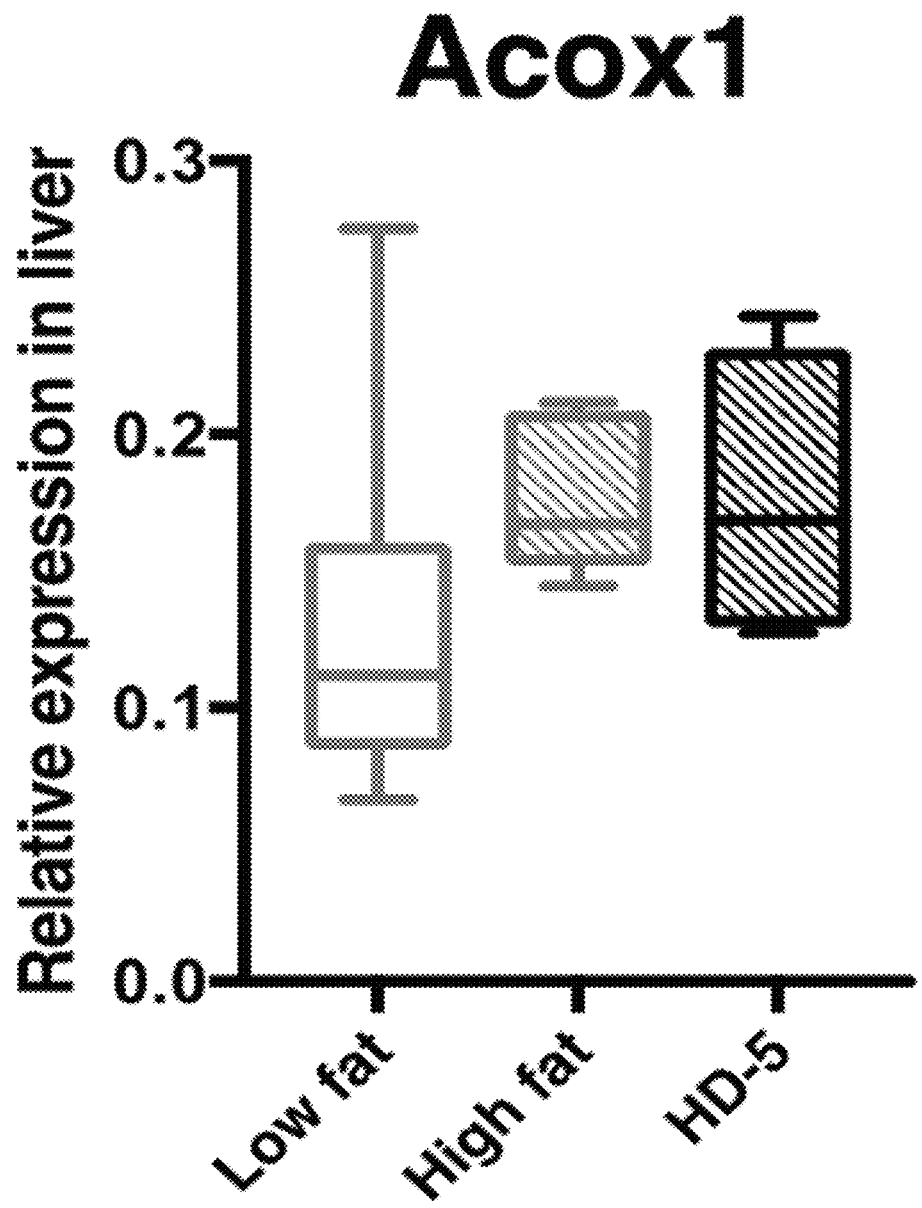

Expression of peroxisomal acyl-coenzyme A oxidase 1 (Acox1) in the liver was substantially the same in all three groups (FIG. 29B), while expression of PPARγ2 was significantly higher in both HFD groups compared to the LFD group (FIG. 29A).

Conclusions of HD5 as Treatment of Weight Gain, Obesity and Fat Accumulation in the Liver in High Fat Diet Fed Mice:

HD5-fed mice had significantly decreased weight change compared with HFD-fed control mice (FIG. 25B).

Figure 26A:
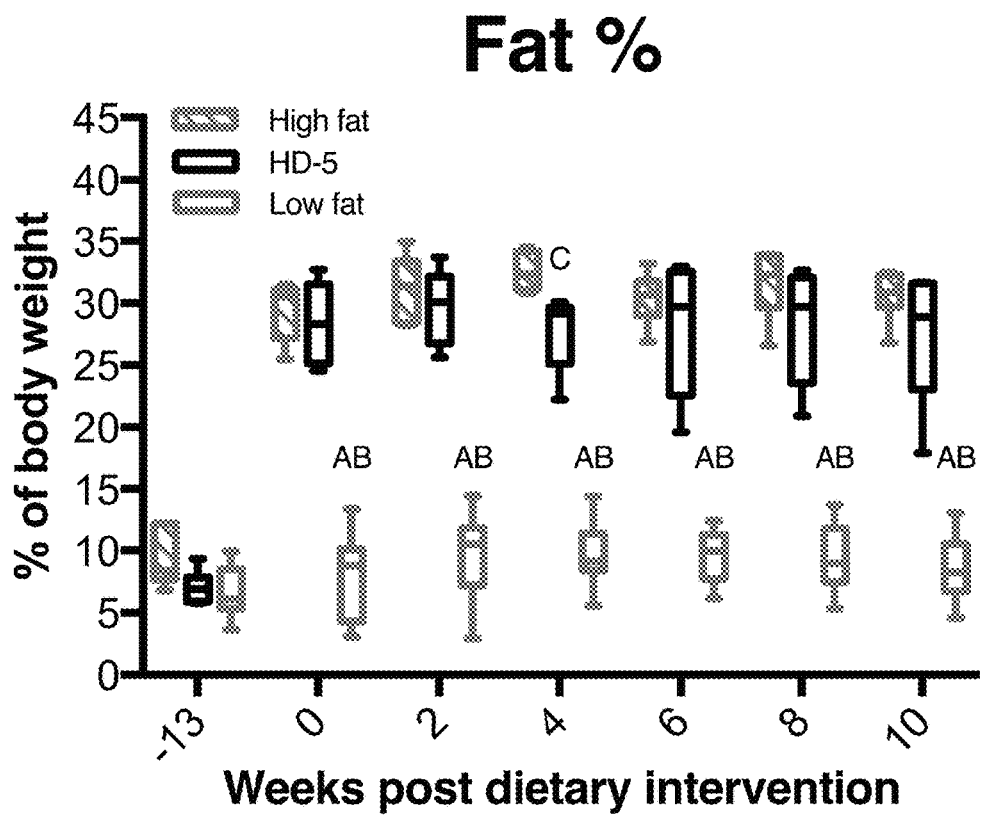
Figure 26B:
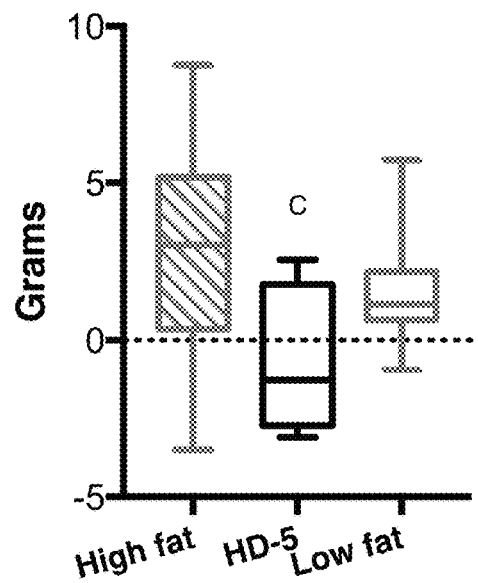
Figure 27A:
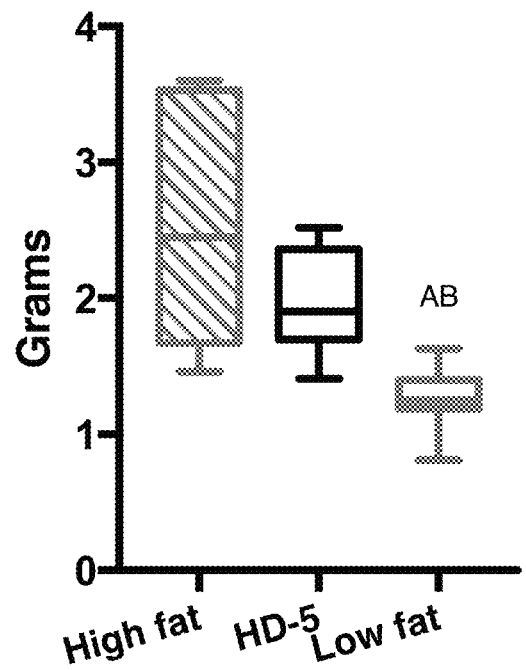
Figure 27B:
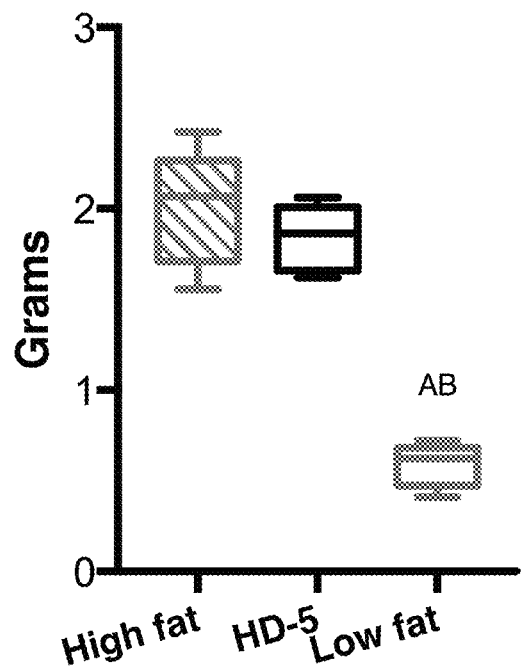

There was a general tendency to decreased fat mass of obese HFD-HD5-fed mice (FIGS. 26A and B).

Liver mass tended to be decreased in HD5-fed mice as compared to HFD-fed control mice (FIG. 27A). Since the visceral and subcutaneous depots were not significantly different (FIG. 27B), this observation suggests that the modestly decreased fat % in HD5 mice is restricted to hepatic lipolysis/lipid oxidation.

Glucose tolerance improved over time in the HD5 fed mice (FIG. 28A),

HD5 fed mice were less insulin resistant than HFD-fed control mice (FIG. 28b).

Figure 30B:
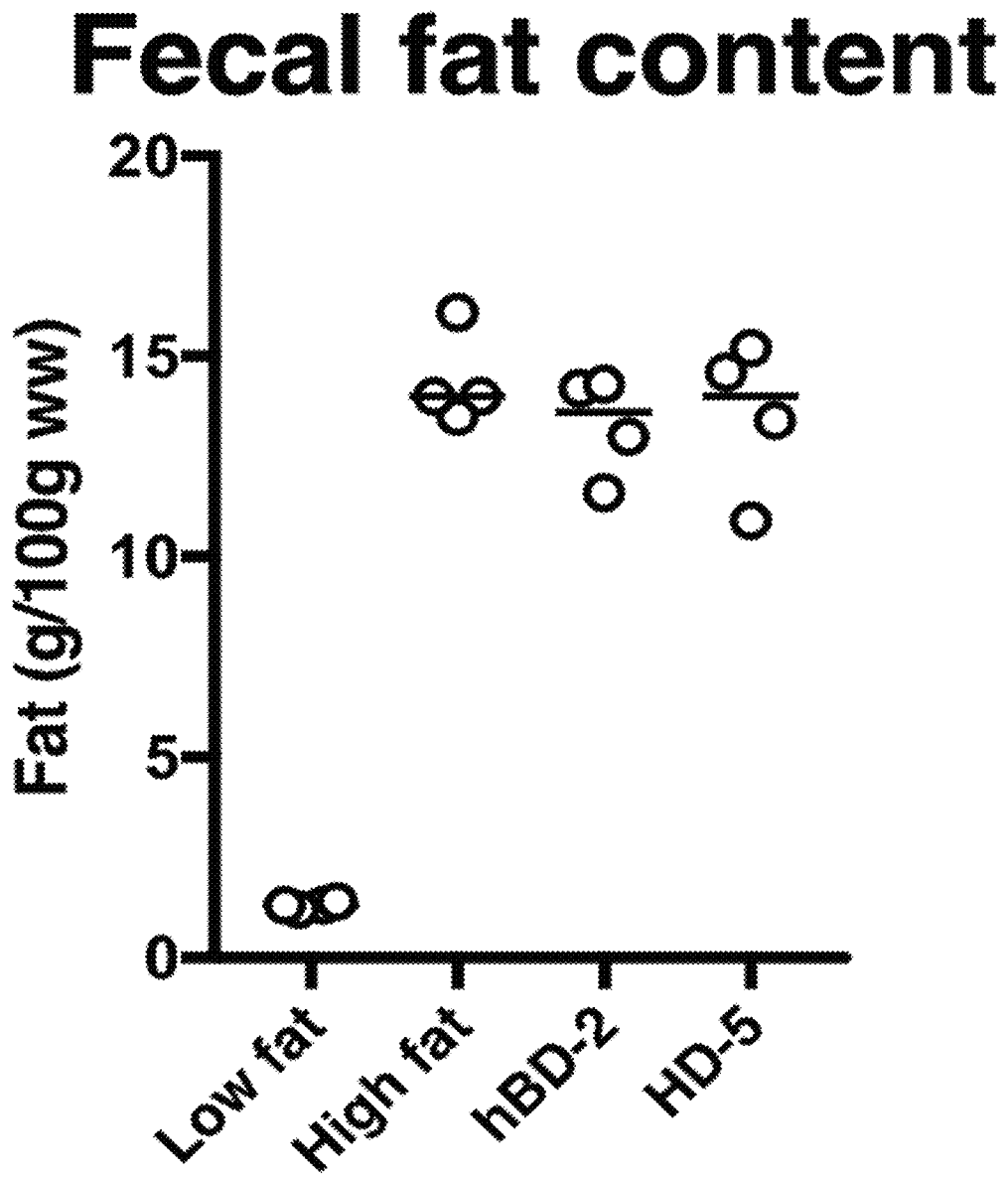

Importantly, uptake of dietary fat was not significantly different between HFD mice, HFD plus hBD-2 mice and HFD plus HD-5 mice (FIG. 30A), which is consistent with the observation that the fecal fat contents were also essentially similar in all three groups (FIG. 30B).

Example 5. Treatment of Weight Gain, Obesity and Fat Accumulation in the Liver in High Fat Diet Fed Mice with a Glucagon Like Peptide-1 (GLP-1) Analog (Liraglutide)

Materials and Methods.

Mice:

4 weeks old C57Bl/6J DIO male mice were fed a high fat diet (HFD 60% fat, SSNIFF (Diet #D12492)) or purina chow for 36 weeks. The HFD fed group had reached an average weight of approximately 55 grams by start of intervention. The mice were group housed 10 per cage until week −2. From week −2 the mice were single housed throughout the study. Feed intake was registered daily just before lights were turned off at 3 pm. Individual mice were subjected to experimental procedures in altered order both group and cage wise. Mice were kept at room temperature under a 12-hour light/dark cycle at SPF standard conditions.

Treatment Regime:

Mice were fed either a high fat diet (HFD) or a low fat (LF) control diet. The HFD contained 2 subgroups; 1 GLP-1 analog and 1 standard HFD without supplementation of GLP-1 analog. The GLP-1 analog liraglutide was dissolved in PBS and 0.1% BSA was added. The GLP-1 analog was administered at 0.2 mg/kg BID subcutaneously.

Results.

The GLP-1 analog was found to have a weight lowering effect as the mice treated with the GLP-1 analog lost 25-30% body weight or an average of 15 gram compared to the untreated HFD reference group of mice (FIG. 32).

The GLP-1 analog also seemed to decrease fat accumulation in the liver as the liver weight in gram at termination in the GLP-1 analog treated group of mice was not statistically significantly different (p<0.001) from the liver weight of the group of chow fed mice (FIG. 33).

In correspondence with these effects the plasma cholesterol level was statistically significantly lower in the GLP-1 analog treated group of mice (p<0.01) compared with the HFD reference group of mice (FIG. 34).

Example 6. Pharmacokinetic Study to Determine Oral Bioavailability and Establish Pharmacokinetic Profile of hBD-2 Following Single Oral Gavage of 4 mg/kg Administration to NMRI Mice Materials and Methods Treatment Regimen:

21 female NMRI mice were dosed by oral gavage 5 ml/kg using a gavage tube and a 1 ml syringe according to the individual body weight obtained on the day of dosing. Urine was strived sampled at random time points by gently massaging the inguinal area of the abdomen. The first blood sample was taken using a submandibular sampling method. The second blood sample was collected from Isoflurane anaesthetised mice. Intestinal samples were taken after euthanasia. The abdomen of each mouse was opened and three sections of the intestines were sampled.

Results hBD-2 does not seem to be absorbed from the healthy intestine as hBD-2 could not be detected by HPLC in any of the serum or urine samples as all values were below the detection level of <10 pg/ml. This indicates that hBD-2 is not systemically available after oral dosing of 4 mg/kg in mice (FIG. 35).

Example 7. Pharmacokinetic Profiles of hBD-2 Fused to the C-Terminal (Molecular Weight 71.336 Da) or N-Terminal (Molecular Weight 71.666 Da) of Human Serum Albumin Following Subcutaneous or Intravenous Administration of a Molar Equivalent to 1 mg/kg hBD-2 (Molecular Weight 66437 Da) to NMRI Female Mice Material and Methods Treatment Regimen:

The animals were dosed 10 ml/kg of stock concentration of 1.65 mg/ml according to the individual body weight (300 µL for a 30 gram mouse). First blood sample was taken using a submandibular sampling method and the second following Isoflurane anaesthesia and euthanasia.

Results hBD-2 showed a half-life of 1 hour and the two fused proteins a half-life of 12 hours. AUC was changed dramatically. Renal clearances were also changed from 10 ml/min for hBD-2 to 0.5-2.2 ml/min for the two fused molecules (FIGS. 36, 37 and 38).

The example demonstrates that the half-life of hBD-2 can be extended markedly by C- or N-terminal conjugation to albumin.

Example 8. Anti-Inflammatory Effect of "hBD-2-Albumin Fusion N-Terminal" in an Acute 10-Day Dextran Sodium Sulphate (DSS) Induced Colitis Model in Mice Material and Methods Treatment Regimen:

"hBD-2-albumin N-terminal" was administered intravenously via the tail vein or subcutaneously with the use of a sterile 25 G needle in a dosing volume of 10 ml/kg body weight. The animals received 1 dose daily for 10 executive days. The active control Dexamethasone (DEX) was given subcutaneously at a dose of 1 mg/kg in a dosing volume of 10 ml/kg body weight OD.

Results

Treatment with "hBD-2-albumin N-terminal" resulted in a significant inhibition of the disease activity index (DAI) when administered daily at a dose of 1.65 mg/kg via the intravenous route (p<0.05). Additionally, on day 10 a significant inhibition of the DAI score was also observed when the "hBD-2-albumin N-terminal" was administered daily at a dose of 1.65 mg/kg and at a dose of 125 mg/kg subcutaneously respectively (p<0.05).

Administration of dextran sodium sulphate resulted in a significant inflammation and injury of the colonic tissue as evidenced after histological examination. Treatment with "hBD-2-albumin N-terminal" did not result in any statistically significant reduction of this histological damage, but similarly the active control DEX failed to significantly reduce histological injury.

The results further showed a significant increase in body weight on day 7 in the animals treated with "hBD-2-albumin N-terminal" despite a transient fall in body weight on days 2 and 3 indicating that "hBD-2-albumin N-terminal" has a pronounced weight preserving effect in the murine DSS model, which is usually associated with dramatic weight loss. In contrast the DEX treated animals displayed a very significant decrease in body weight from day 5 onwards (p<0.01).

The example demonstrates the hBD-2-albumin fusion N-terminal is biologically active in an animal model of an inflammatory condition (FIG. 39).

Example 9. Anti-Inflammatory Effect of "hBD-2-Albumin Fusion C-Terminal" in an Acute 10-Day Dextran Sodium Sulphate (DSS) Induced Colitis Model in Mice Material and Methods Treatment Regimen:

"hBD-2-albumin C-terminal" was administered intravenously via the tail vein or subcutaneously with the use of a sterile 25 G needle in a dosing volume of 10 ml/kg body weight. The animals received 1 dose daily for 10 executive days. The active control Prednisolone (Pred) was given orally by gavage at a dose of 1 mg/kg in a dosing volume of 10 ml/kg body weight OD.

Results

Treatment with "hBD-2-albumin C-terminal" resulted in a significant inhibition of the DAI when administered daily at a dose of 1.6 mg/kg via the intravenous route (p<0.05). Additionally "hBD-2-albumin C-terminal" resulted in a significant inhibition of the DAI when administered on alternative days 0, 2, 4, 6, 8 and 10 at a dose of 1.6 mg/kg via the intravenous route (p<0.05). Daily treatment with Pred resulted in a significant inhibition of the DAI on day 9 (p<0.05).

Administration of dextran sodium sulphate resulted in a significant inflammation and injury of the colonic tissue as evidenced after histological examination. Treatment with "hBD-2-albumin C-terminal" at a dose of 1.6 mg/kg resulted in a statistically significant reduction of this histological damage (p<0.05). Similarly, daily treatment with "hBD-2-albumin C-terminal" at a dose of 1.6 mg/kg and of 16.5 mg/kg on days 0, 2, 4, 6, 8, and 10 resulted in a significant reduction of the histological damage to the colon (p<0.01). Treatment with the active control Pred failed to significantly reduce histological injury in the proximal part of the colon but did reduce the injury in the distal colon (p<0.01).

The results further showed a significant increase in body weight in the animals treated with "hBD-2-albumin C-terminal" (p<0.05) indicating a weight preserving effect of "hBD-2-albumin C-terminal".

The example demonstrates the hBD-2-albumin fusion C-terminal is biologically active in an animal model of an inflammatory condition.

Example 10. Sequences

| SEQ ID NO. | Name | Sequence |
|---|---|---|
| 1 | Bovine beta defensin 2 | GVGNPVSCVRNKGICVPIRCPGSMKQIGTCVGRAVKCCRK |
| 2 | Chicken beta defensin 2 | LFCKGGSCHFGGCPSHLIKVGSCFRSCCKWPWNA |
| 3 | Orangutan beta defensin 2 | VFGDISNPVTCLRSGAICHPGFCPRRYKHIGTCGLSVIKCCKKP |
| 4 | hBD1 | DHYNCVSSGGQCLYSACPIFTKIQGTCYRGKAKCCK |
| 5 | hBD2 | GIGDPVTCLKSGAICHPVFCPRRYKQIGTCGLPGTKCCKKP |
| 6 | hBD3 | GIINTLQKYYCRVRGGRCAVLSCLPKEEQIGKCSTRGRKCCRRKK |
| 7 | hBD4 | ELDRICGYGTARCRKKCRSQEYRIGRCPNTYACCLRK |
| 8 | HD5 | ATCYCRTGRCATRESLSGVCEISGRLYRLCCR |
| 9 | HD6 | AFTCHCRRSCYSTEYSYGTCTVMGINHRFCCL |
| 10 | Chimpanzee beta defensin 2 | GISDPVTCLKSGAICHPVFCPRRYKQIGTCGLPGTKCCKKP |
| 11 | Macaque beta defensin 2 | GIGDPVTCLKNGAICHPVFCPRRYKQIGTCGLPGTKCCKKP |
| 12 | Mouse beta defensin 3 | KINNPVSCLRKGGRCWNRCIGNTRQIGSCGVPFLKCCKRK |
| 13 | Horse beta defensin 2 | GIGNPISCARNRGVCIPIGCLPGMKQIGTCGLPGTKCCRK |
| 14 | Porcine beta defensin 1 | NIGNSVSCLRNKGVCMPGKCAPKMKQIGTCGMPQVKCCKR |
| 15 | Goat beta defensin 2 | GIINHRSCYRNKGVCAPARCPRNMRQIGTCHGPPVKCCRK |
| 16 | human LL37 | LLGDFFRKSKEKIGKEFKRIVQRIKDFLRNLVPRTES |
| 17 | truncated hBD2 | PVTCLKSGAICHPVFCPRRYKQIGTCGLPGTKCCKKP |

REFERENCES

Ajslev T A, et al, 2014. Trends in parent-child correlations of childhood body mass index during the development of the obesity epidemic. PLoS One 9(10).

Angelakis E and Raoult D, 2010. The increase of *Lactobacillus* species in the gut flora of newborn broiler chicks and ducks is associated with weight gain. PLoS One 5(5).

Angelakis E., et al 2012. An evaluation of the effects of *Lactobacillus ingluviei* on body weight, the intestinal microbiome and metabolism in mice. Microb Pathog 52(1):61-8.

Armogida S A, et al, 2004. Identification and quantification of innate immune system mediators in human breast milk. Allergy Asthma Proc. 25(5):297-304.

Bäckhed F, et al, 2007. Mechanisms underlying the resistance to diet-induced obesity in germ-free mice. Proc Natl Acad Sci USA 104(3):979-84.

Belkaid W and Hand T W, 2014. Role of the microbiota in immunity and inflammation. Cell 157(1):121-41.

Bowie J U and Sauer R T, 1989. Identifying determinants of folding and activity for a protein of unknown structure. *Proc. Natl. Acad. Sci. USA* 86: 2152-2156;

Chassaing B, et al, 2015. Dietary emulsifiers impact the mouse gut microbiota promoting colitis and metabolic syndrome. Nature 519(7541):92-6.

Cunningham B C and Wells J A, 1989. High-resolution epitope mapping of hGH-receptor interactions by alanine-scanning mutagenesis. *Science* 244: 1081-1085.

Derbyshire K M, Salvo J J and Grindley N D, 1986. A simple and efficient procedure for saturation mutagenesis using mixed oligodeoxynucleotides. *Gene* 46:145-152.

Everard A and Cani P D, 2013. Diabetes, obesity and gut microbiota. Best Pract Res Clin Gastroenterol 27(1):73-83.

Faulds M H and Dahlman-Wright K, 2012. Metabolic diseases and cancer risk. Curr Opin Oncol. 24(1):58-61.

Favre-Godal Q, et al, 2014. Comprehensive approach for the detection of antifungal compounds using a susceptible strain of *Candida albicans* and confirmation of in vivo activity with the *Galleria mellonella* model. Phytochemistry. 105: 68-78.

Feng Q, et al, 2015. Gut microbiome development along the colorectal adenoma-carcinoma sequence. Nat Commun 6:6528.

Giannouli M, et al. Use of larvae of the wax moth *Galleria mellonella* as an in vivo model to study the virulence of *Helicobacter pylori*. 2014. BMC Microbiol 14: 228.

Hilton D J, et al, 1996. Saturation mutagenesis of the WSXWS motif of the erythropoietin receptor. J. Biol. Chem. 271: 4699-4708.

Harada K, et al, 2004. Peptide antibiotic human beta-defensin-1 and -2 contribute to antimicrobial defense of the intrahepatic biliary tree. Hepatology, vol 40: 925-932.

Khan M, et al, 2007. Growth-promoting effects of single-dose intragastrically administered probiotics in chickens. Br Poult Sci 48(6):732-5.

Koren O, et al, 2012. Host remodeling of the gut microbiome and metabolic changes during pregnancy. Cell 150 (3):470-80.

Le Chatelier E et al. 2013. Richness of human gut microbiome correlates with metabolic markers. Nature 500 (7464):541-6.

Leviten M, 2016. The Finnish connection. Biocentury Innovations, June 16.

Liu hY et al, 2008. Suppression of hepatic glucose production by human neutrophil α-defensin through a signaling pathway distinct from insulin. The Journal of Biological Chemistry 283(18):12056-12063.

Lowman H B, Bass S H, Simpson N and Wells J A, 1991. Selecting high-affinity binding proteins by monovalent phage display. *Biochem* 30:10832-10837.

Mowat A M and Agace W W, 2014. Regional specialization within the intestinal immune system. Nat Rev Immunol. 14(10):667-85.

Needleman S B and Wunsch C D, 1970. A general method applicable to the search for similarities in the amino acid sequence of two proteins. J. Mol. Biol. 48: 443-453.

Ner S S, Goodin D B and Smith M, 1988. A simple and efficient procedure for generating random point mutations and for codon replacements using mixed oligodeoxynucleotides. *DNA* 7:127-134.

Neurath H and Hill R L, 1979. The Proteins. Academic Press, New York.

Paige et al. Pharmaceutical Research, vol. 12, no. 12, 1995. Prolonged circulation of recombinant human granulocyte-colony stimulating factor by covalent linkage to albumin through a heterobifunctional polyethylene glycol.

Qin J, et al 2012. A metagenome-wide association study of gut microbiota in type 2 diabetes. Nature 490(7418):55-60.

Reidhaar-Olson J F and Sauer R T, 1988. Combinatorial cassette mutagenesis as a probe of the informational content of protein sequences. Science 241:53-57;

Gennaro A R, 1990. Remington's Pharmaceutical Sciences. Ed. Mack Publishing Co., Easton, PA Rice P, Longden I and Bleasby A, 2000. EMBOSS: the European Molecular Biology Open Software Suite. Trends in Genetics 16: 276-277.

Ridaura V K, et al, 2013. Gut microbiota from twins discordant for obesity modulate metabolism in mice. Science 341(6150):1241214.

Salzman N H, Underwood M A and Bevins C L, 2007. Paneth cells, defensins, and the commensal microbiota: a hypothesis on intimate interplay at the intestinal mucosa. Semin Immunol 19(2):70-83.

Shechter et al. Bioconjugate Chem. 2005, 16: 913-920

Shechter et al. International Journal of Peptide Research and Therapeutics, Vol. 13, Nos. 1-2, June 2007

Suez J, et al, 2014. Artificial sweeteners induce glucose intolerance by altering the gut microbiota. Nature 514 (7521):181-6.

Trasande L, Blustein J, Liu M, Corwin E, Cox L M and Blaser M J, 2012. Infant antibiotic exposures and early-life body mass. Int J Obes (Lond) 37(1):16-23.

Turnbaugh P J, Ley R E, Mahowald M A, Magrini V, Mardis E R and Gordon J I, 2006. An obesity-associated gut microbiome with increased capacity for energy harvest. Nature. 2006 Dec. 21; 444(7122):1027-31.

Turnbaugh P J, Bäckhed F, Fulton L and Gordon J I, 2008. Diet-induced obesity is linked to marked but reversible alterations in the mouse distal gut microbiome. Cell Host Microbe 3(4):213-23.

Vrieze A, et al 2012. Transfer of intestinal microbiota from lean donors increases insulin sensitivity in individuals with metabolic syndrome. Gastroent 143(4):913-6.

Walter, 2015. Murine gut microbiota-diet trumps genes. Cell Host Microbe 17(1):3-5.

Wehkamp J, et al, 2002. Innate immunity and colonic inflammation: enhanced expression of epithelial alpha-defensins. Dig Dis Sci. 47(6):1349-55.

Wertenbruch S, et al, 2015. The anti-microbial peptide LL-37/CRAMP is elevated in patients with liver diseases and acts as a protective factor during mouse liver injury. Digestion, 91:307-317.

Zhang X, et al, 2015. The oral and gut microbiomes are perturbed in rheumatoid arthritis and partly normalized after treatment. Nat Med 21(8):895-905.

And following patents and patent applications:
WO 2010/007166
WO 92/06204
WO 95/17413
WO 95/22625
U.S. Pat. No. 5,223,409
CN104971343

The invention claimed is:

1. A method for alleviating or relieving symptom of a liver disorder selected from the group consisting of toxic liver disease, alcoholic or non-alcoholic fatty liver disease (NAFLD), hepatitis, liver cirrhosis, hepatic failure, liver fibrosis, liver sclerosis, hepatic encephalopathy, and non-alcoholic steatohepatitis (NASH);
   a biliary tract disorder selected from cholangitis, primary sclerosing cholangitis, cholecystitis;
   pancreatitis; or
   a metabolic disease selected from the group consisting of: hypercholesterolaemia, hyperglyceridaemia, hyperlipidaemia, hyperchylomicronaemia, glycogen storage disease, gangliosidosis, and sphingolipidosis, said method comprising administration of an effective amount of a mammalian β-defensin selected from the group consisting of hBD1, hBD2, N-terminally truncated hBD2, hBD3, and hBD4 to a subject in need thereof.

2. The method according to claim 1, wherein the defensin is administered to the subject in need thereof at a daily dosage between 0.1 mg/kg and 10 mg/kg.

3. The method according to claim 1, wherein said defensin further comprises at least one further moiety selected from a group consisting of a cell penetrating peptide (CPP), an Albumin Binding Moiety (ABM), a detectable moiety (Z), and a half-life extending peptide.

4. The method of claim 1, wherein the disease or disorder is a liver disorder selected from toxic liver disease, alcoholic or non-alcoholic fatty liver disease (NAFLD), hepatitis, liver cirrhosis, hepatic failure, liver fibrosis, liver sclerosis, hepatic encephalopathy, and non-alcoholic steatohepatitis (NASH).

5. The method of claim 1, wherein the disease or disorder is a biliary tract disorder selected from cholangitis, primary sclerosing cholangitis, and cholecystitis.

6. The method of claim 1, wherein the disease is pancreatitis.

7. The method of claim 1, wherein the disease is a metabolic disease selected from the group consisting of: hypercholesterolaemia; hyperglyceridaemia; hyperlipidaemia; hyperchylomicronaemia; glycogen storage disease; gangliosidosis; and sphingolipidosis.

8. The method according to claim 1, wherein said method further comprises administering an antibiotic, insulin/insulin analog, glucagon like peptide-1 (GLP-1)/GLP-1 analog, glucagon like peptide-2 (GLP-2)/GLP-2 analog, a dipeptidyl peptidase IV (DPP-IV) inhibitor, metformin, sodium glucose transporter-2 (SGLT-2) inhibitor, glucagon receptor antagonist, or a transient receptor potential cation channel subfamily V member 1 (TRPV1) antagonist, to the subject.

9. The method according to claim 1, wherein the mammalian β-defensin is hBD-2.

10. The method according to claim 1, wherein the subject has:
   i) a BMI of 25 or more;
   ii) a waist/hip ratio of at least 0.80;
   iii) a fasting blood glucose of at least 6.1 mmol/l; or
   iv) a glycated haemoglobin level of at least 42 mmol/mol Hb.

11. The method according to claim 1, wherein the subject has one or more of the following symptoms:
   Elevated blood pressure: ≥140/90 mmHg;
   Dyslipidemia: triglycerides (TG): ≥1.695 mmol/L and high-density lipoprotein cholesterol (HDL-C)≤0.9 mmol/L (male), ≤1.0 mmol/L (female);
   AST/ALT>1;
   Fasting glucose >6.1 mmol/L;
   Central obesity: waist:hip ratio >0.90 (male); >0.85 (female), or body mass index>30 kg/m$^2$; and
   Microalbuminuria: urinary albumin excretion ratio ≥20 μg/min or albumin:creatinine ratio ≥30 mg/g.

12. The method according to claim 1, wherein the defensin is administered to the subject in need thereof once, twice, or three times a week; or once a day, or at least two to three times a day.

13. The method according to claim 1, wherein the defensin is administered as a food or drink supplement.

14. The method according to claim 1, wherein the administration is oral or subcutaneous.

15. The method according to claim 1, wherein the mammalian β-defensin is conjugated to a half-life extending moiety.

16. The method according to claim 1, wherein said method reduces at least one of liver fat, liver steatosis, visceral fat, or increases liver fatty acid metabolism.

17. The method according to claim 1, wherein said method decreases liver PPARγ2 expression or increases liver Acox1 expression.

18. A method for reducing the expression of PPARγ2, said method comprising prophylactic administration of an effective amount of a mammalian β-defensin selected from the group consisting of hBD1, hBD2, N-terminally truncated hBD2, hBD3, and hBD4 to a subject at risk of developing a liver disorder selected from the group consisting of toxic liver disease, alcoholic or non-alcoholic fatty liver disease (NAFLD), hepatitis, liver cirrhosis, hepatic failure, liver fibrosis, liver sclerosis, hepatic encephalopathy, and non-alcoholic steatohepatitis (NASH).

19. A method for increasing the expression of Acox1, said method comprising administration of an effective amount of a mammalian β-defensin selected from the group consisting of hBD1, hBD2, N-terminally truncated hBD2, hBD3, and hBD4 to a subject at risk of developing a liver disorder selected from the group consisting of toxic liver disease, alcoholic or non-alcoholic fatty liver disease (NAFLD), hepatitis, liver cirrhosis, hepatic failure, liver fibrosis, liver sclerosis, hepatic encephalopathy, and non-alcoholic steatohepatitis (NASH).

20. A method for reducing at least one of liver fat, liver steatosis, visceral fat, or increasing liver fatty acid metabolism in a subject at risk of developing a liver disorder selected from the group consisting of toxic liver disease, alcoholic or non-alcoholic fatty liver disease (NAFLD), hepatitis, liver cirrhosis, hepatic failure, liver fibrosis, liver sclerosis, hepatic encephalopathy, and non-alcoholic steatohepatitis (NASH), said method comprising administration to said subject of an effective amount of a mammalian β-defensin selected from the group consisting of hBD1, hBD2, N-terminally truncated hBD2, hBD3, and hBD4.

* * * * *

SEQUENCE LISTING

```
<160> NUMBER OF SEQ ID NOS: 20

<210> SEQ ID NO 1
<211> LENGTH: 40
<212> TYPE: PRT
<213> ORGANISM: Bos taurus

<400> SEQUENCE: 1

Gly Val Gly Asn Pro Val Ser Cys Val Arg Asn Lys Gly Ile Cys Val
1               5                   10                  15

Pro Ile Arg Cys Pro Gly Ser Met Lys Gln Ile Gly Thr Cys Val Gly
            20                  25                  30

Arg Ala Val Lys Cys Cys Arg Lys
        35                  40

<210> SEQ ID NO 2
<211> LENGTH: 34
<212> TYPE: PRT
<213> ORGANISM: Gallus gallus

<400> SEQUENCE: 2

Leu Phe Cys Lys Gly Gly Ser Cys His Phe Gly Gly Cys Pro Ser His
1               5                   10                  15

Leu Ile Lys Val Gly Ser Cys Phe Arg Ser Cys Cys Lys Trp Pro Trp
            20                  25                  30

Asn Ala

<210> SEQ ID NO 3
<211> LENGTH: 44
```

-continued

```
<212> TYPE: PRT
<213> ORGANISM: Pongo pygmaeus

<400> SEQUENCE: 3

Val Phe Gly Asp Ile Ser Asn Pro Val Thr Cys Leu Arg Ser Gly Ala
1               5                   10                  15

Ile Cys His Pro Gly Phe Cys Pro Arg Arg Tyr Lys His Ile Gly Thr
                20                  25                  30

Cys Gly Leu Ser Val Ile Lys Cys Cys Lys Lys Pro
            35                  40

<210> SEQ ID NO 4
<211> LENGTH: 36
<212> TYPE: PRT
<213> ORGANISM: Homo sapiens

<400> SEQUENCE: 4

Asp His Tyr Asn Cys Val Ser Ser Gly Gly Gln Cys Leu Tyr Ser Ala
1               5                   10                  15

Cys Pro Ile Phe Thr Lys Ile Gln Gly Thr Cys Tyr Arg Gly Lys Ala
                20                  25                  30

Lys Cys Cys Lys
            35

<210> SEQ ID NO 5
<211> LENGTH: 41
<212> TYPE: PRT
<213> ORGANISM: Homo sapiens

<400> SEQUENCE: 5

Gly Ile Gly Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
                20                  25                  30

Pro Gly Thr Lys Cys Cys Lys Lys Pro
            35                  40

<210> SEQ ID NO 6
<211> LENGTH: 45
<212> TYPE: PRT
<213> ORGANISM: Homo sapiens

<400> SEQUENCE: 6

Gly Ile Ile Asn Thr Leu Gln Lys Tyr Tyr Cys Arg Val Arg Gly Gly
1               5                   10                  15

Arg Cys Ala Val Leu Ser Cys Leu Pro Lys Glu Glu Gln Ile Gly Lys
                20                  25                  30

Cys Ser Thr Arg Gly Arg Lys Cys Cys Arg Arg Lys Lys
            35                  40                  45

<210> SEQ ID NO 7
<211> LENGTH: 37
<212> TYPE: PRT
<213> ORGANISM: Homo sapiens

<400> SEQUENCE: 7

Glu Leu Asp Arg Ile Cys Gly Tyr Gly Thr Ala Arg Cys Arg Lys Lys
1               5                   10                  15

Cys Arg Ser Gln Glu Tyr Arg Ile Gly Arg Cys Pro Asn Thr Tyr Ala
                20                  25                  30
```

```
Cys Cys Leu Arg Lys
        35
```

<210> SEQ ID NO 8
<211> LENGTH: 32
<212> TYPE: PRT
<213> ORGANISM: Homo sapiens

<400> SEQUENCE: 8

```
Ala Thr Cys Tyr Cys Arg Thr Gly Arg Cys Ala Thr Arg Glu Ser Leu
1               5                   10                  15

Ser Gly Val Cys Glu Ile Ser Gly Arg Leu Tyr Arg Leu Cys Cys Arg
            20                  25                  30
```

<210> SEQ ID NO 9
<211> LENGTH: 32
<212> TYPE: PRT
<213> ORGANISM: Homo sapiens

<400> SEQUENCE: 9

```
Ala Phe Thr Cys His Cys Arg Arg Ser Cys Tyr Ser Thr Glu Tyr Ser
1               5                   10                  15

Tyr Gly Thr Cys Thr Val Met Gly Ile Asn His Arg Phe Cys Cys Leu
            20                  25                  30
```

<210> SEQ ID NO 10
<211> LENGTH: 41
<212> TYPE: PRT
<213> ORGANISM: Pan troglodytes

<400> SEQUENCE: 10

```
Gly Ile Ser Asp Pro Val Thr Cys Leu Lys Ser Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
            35                  40
```

<210> SEQ ID NO 11
<211> LENGTH: 41
<212> TYPE: PRT
<213> ORGANISM: Macaca mulatta

<400> SEQUENCE: 11

```
Gly Ile Gly Asp Pro Val Thr Cys Leu Lys Asn Gly Ala Ile Cys His
1               5                   10                  15

Pro Val Phe Cys Pro Arg Arg Tyr Lys Gln Ile Gly Thr Cys Gly Leu
            20                  25                  30

Pro Gly Thr Lys Cys Cys Lys Lys Pro
            35                  40
```

<210> SEQ ID NO 12
<211> LENGTH: 40
<212> TYPE: PRT
<213> ORGANISM: Mus musculus

<400> SEQUENCE: 12

```
Lys Ile Asn Asn Pro Val Ser Cys Leu Arg Lys Gly Gly Arg Cys Trp
1               5                   10                  15

Asn Arg Cys Ile Gly Asn Thr Arg Gln Ile Gly Ser Cys Gly Val Pro
            20                  25                  30
```

-continued

Phe Leu Lys Cys Cys Lys Arg Lys
            35                  40

<210> SEQ ID NO 13
<211> LENGTH: 40
<212> TYPE: PRT
<213> ORGANISM: Equus caballus

<400> SEQUENCE: 13

Gly Ile Gly Asn Pro Ile Ser Cys Ala Arg Asn Arg Gly Val Cys Ile
1               5                   10                  15

Pro Ile Gly Cys Leu Pro Gly Met Lys Gln Ile Gly Thr Cys Gly Leu
            20                  25                  30

Pro Gly Thr Lys Cys Cys Arg Lys
            35                  40

<210> SEQ ID NO 14
<211> LENGTH: 40
<212> TYPE: PRT
<213> ORGANISM: Sus scrofa

<400> SEQUENCE: 14

Asn Ile Gly Asn Ser Val Ser Cys Leu Arg Asn Lys Gly Val Cys Met
1               5                   10                  15

Pro Gly Lys Cys Ala Pro Lys Met Lys Gln Ile Gly Thr Cys Gly Met
            20                  25                  30

Pro Gln Val Lys Cys Cys Lys Arg
            35                  40

<210> SEQ ID NO 15
<211> LENGTH: 40
<212> TYPE: PRT
<213> ORGANISM: Capra aegagrus

<400> SEQUENCE: 15

Gly Ile Ile Asn His Arg Ser Cys Tyr Arg Asn Lys Gly Val Cys Ala
1               5                   10                  15

Pro Ala Arg Cys Pro Arg Asn Met Arg Gln Ile Gly Thr Cys His Gly
            20                  25                  30

Pro Pro Val Lys Cys Cys Arg Lys
            35                  40

<210> SEQ ID NO 16
<211> LENGTH: 37
<212> TYPE: PRT
<213> ORGANISM: Homo sapiens

<400> SEQUENCE: 16

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
            35

<210> SEQ ID NO 17
<211> LENGTH: 37
<212> TYPE: PRT
<213> ORGANISM: Homo sapiens

<400> SEQUENCE: 17

```
Pro Val Thr Cys Leu Lys Ser Gly Ala Ile Cys His Pro Val Phe Cys
1               5                   10                  15

Pro Arg Arg Tyr Lys Gln Ile Gly Thr Cys Gly Leu Pro Gly Thr Lys
                20                  25                  30

Cys Cys Lys Lys Pro
            35

<210> SEQ ID NO 18
<211> LENGTH: 29
<212> TYPE: PRT
<213> ORGANISM: Homo sapiens

<400> SEQUENCE: 18

Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
                20                  25

<210> SEQ ID NO 19
<211> LENGTH: 30
<212> TYPE: PRT
<213> ORGANISM: Homo sapiens

<400> SEQUENCE: 19

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30

<210> SEQ ID NO 20
<211> LENGTH: 30
<212> TYPE: PRT
<213> ORGANISM: Homo sapiens

<400> SEQUENCE: 20

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
                20                  25                  30
```